United States Patent
Ikemizu et al.

(10) Patent No.: US 9,331,289 B2
(45) Date of Patent: May 3, 2016

(54) ORGANIC ELECTROLUMINESCENT MATERIAL, ORGANIC ELECTROLUMINESCENT ELEMENT, DISPLAY DEVICE AND LIGHTING DEVICE

(75) Inventors: Dai Ikemizu, Tokyo (JP); Hiroshi Kita, Tokyo (JP); Tomohiro Oshiyama, Tokyo (JP); Shinya Otsu, Tokyo (JP); Rie Katakura, Tokyo (JP); Hidekane Ozeki, Tokyo (JP)

(73) Assignee: KONICA MINOLTA HOLDINGS, INC., Tokyo (JP)

( * ) Notice: Subject to any disclaimer, the term of this patent is extended or adjusted under 35 U.S.C. 154(b) by 546 days.

(21) Appl. No.: 13/703,246

(22) PCT Filed: Apr. 8, 2011

(86) PCT No.: PCT/JP2011/058871
§ 371 (c)(1),
(2), (4) Date: Dec. 10, 2012

(87) PCT Pub. No.: WO2011/158544
PCT Pub. Date: Dec. 22, 2011

(65) Prior Publication Data
US 2013/0099216 A1 Apr. 25, 2013

(30) Foreign Application Priority Data
Jun. 17, 2010 (JP) .................. 2010-138113

(51) Int. Cl.
*H01L 51/00* (2006.01)
*H01L 51/50* (2006.01)
(Continued)

(52) U.S. Cl.
CPC ........ *H01L 51/0083* (2013.01); *C07F 15/0033* (2013.01); *C07F 15/0086* (2013.01);
(Continued)

(58) Field of Classification Search
None
See application file for complete search history.

(56) References Cited

U.S. PATENT DOCUMENTS
2005/0072970 A1\* 4/2005 Saito .................... 257/40
2008/0036373 A1 2/2008 Itoh
(Continued)

FOREIGN PATENT DOCUMENTS
GB 2 423 518 8/2006
JP 2004-315509 11/2004
(Continued)

OTHER PUBLICATIONS

European Search Report, Application No. 11 795 452.9. Dated: Mar. 28, 2014 (6 pages).
(Continued)

*Primary Examiner* — Ling Choi
*Assistant Examiner* — Catherine S Branch
(74) *Attorney, Agent, or Firm* — Lucas & Mercanti, LLP

(57) ABSTRACT

Disclosed are: an organic EL material which emits light having a short wavelength and has high luminous efficiency and long light emission life; an organic EL element which contains the organic EL material; and a lighting device and a display device, each of which comprises the organic EL element. The organic EL material is a compound represented by Formula (1):

Formula (1)

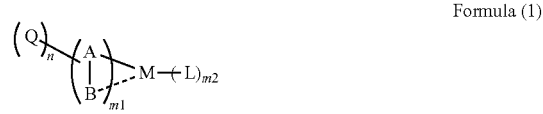

18 Claims, 2 Drawing Sheets

(51) Int. Cl.
*C07F 15/00* (2006.01)
*C09K 11/06* (2006.01)

(52) U.S. Cl.
CPC ............ C09K11/06 (2013.01); H01L 51/0085 (2013.01); H01L 51/5012 (2013.01); *C09K 2211/1007* (2013.01); *C09K 2211/1029* (2013.01); *C09K 2211/1033* (2013.01); *C09K 2211/1037* (2013.01); *C09K 2211/1044* (2013.01); *C09K 2211/1048* (2013.01); *C09K 2211/1051* (2013.01); *C09K 2211/1059* (2013.01); *C09K 2211/1074* (2013.01); *C09K 2211/1092* (2013.01); *C09K 2211/1096* (2013.01); *C09K 2211/14* (2013.01); *C09K 2211/1433* (2013.01); *C09K 2211/185* (2013.01); *H01L 51/5016* (2013.01)

(56) References Cited

U.S. PATENT DOCUMENTS

| | | | | |
|---|---|---|---|---|
| 2010/0187980 | A1* | 7/2010 | Langer et al. | 313/504 |
| 2012/0261651 | A1* | 10/2012 | Noto | C09K 11/06 257/40 |

FOREIGN PATENT DOCUMENTS

| | | |
|---|---|---|
| JP | 2006-290891 | 10/2006 |
| JP | 2008-542203 | 11/2008 |
| JP | WO 2011021385 A1 * | 2/2011 ............ C09K 11/06 |
| WO | 2004-085450 | 10/2004 |
| WO | 2006/046980 | 5/2006 |
| WO | 2007/095118 | 8/2007 |
| WO | WO 2008132085 A1 * | 11/2008 |
| WO | 2008/156879 | 12/2008 |
| WO | 2009/060757 | 5/2009 |

OTHER PUBLICATIONS

Article by Christopher Herrmann, et al, "Chemical Behavior of a Pair of (COD) CpRh and -Ir Complexes with Pendant Peripheral-B(C 6 F 5) 2 Groups +", Organometallics, vol. 27, No. 10, May 1, 2008, pp. 2328-2336, XP55108555, ISSN: 0276-7333, DOI: 10.1021/om800195d.

Qiang Zhao et al: "Highly Selective Phosphorescent Chemosensor for Fluoride Based on an Iridium (III) Complex Containing Arylborane Units"), Inorganic Chemistry, vol. 47, No. 20, Oct. 20, 2008, pp. 9256-9264, XP55108544, ISSN: 0020-1669, DOI: 10.1021/ic800500c.

Non-patent document 1: Inorg. Chem. 2005, 44(13), 4737-4746.

Non-patent document 2: Inorg. Chem. 2006, 45 (22) 8907-8921.

Journal of the American Chemical Society, 2001 vol. 123, 4304-4312.

Non-patent document: Inorg. Chem. 2006, 45 (26), 10670-10677.

* cited by examiner

ORGANIC ELECTROLUMINESCENT MATERIAL, ORGANIC ELECTROLUMINESCENT ELEMENT, DISPLAY DEVICE AND LIGHTING DEVICE

CROSS REFERENCE TO RELATED APPLICATION

This Application is a 371 of PCT/JP2011/058871 filed on Apr. 8, 2011 which, in turn, claimed the priority of Japanese Patent Application No. 2010-138113 filed on Jun. 17, 2010, both applications are incorporated by reference herein

TECHNICAL FIELD

The present invention relates to an organic electroluminescence material, an organic electroluminescence element, a display device and a lighting device.

BACKGROUND

Conventionally, an emission type electronic display device includes an electroluminescence display (hereinafter, referred to as an ELD). A constituent element of an ELD includes such as an inorganic electroluminescence element and an organic electroluminescence element (hereinafter, referred to as an organic EL element).

An inorganic electroluminescence element has been utilized as a flat light source, however, it requires a high voltage of alternating current to operate an emission element.

On the other hand, an organic electroluminescence element is an element provided with a constitution comprising an emitting layer containing a emitting substance being sandwiched with a cathode and an anode, and an exciton is generated by an electron and a hole being injected into the emitting layer to be recombined, resulting emission utilizing light release (fluorescence and phosphorescence) at the time of deactivation of said exciton; the emission is possible at a voltage of approximately a few to a few tens volts, and an organic electroluminescence element is attracting attention with respect to such as superior viewing angle and high visual recognition due to a self-emission type as well as space saving and portability due to a completely solid element of a thin layer type.

However, in an organic electroluminescence in view of the future practical application, desired has been development of an organic EL element which efficiently emits at a high luminance with a low electric consumption.

In Japanese Patent No. 3093796, a slight amount of a fluorescent substance has been doped in a stilbene derivative, a distyrylarylene derivative or a tristyrylarylene derivative, to achieve improved emission luminance and a prolonged lifetime of an element.

Further, there are known such as an element, having an organic emitting layer comprising a 8-hydroxyquinoline aluminum complex as a host compound which is doped, with a slight amount of a fluorescent substance (for example, JP-A No. 63-264692) and an element having an organic emitting layer comprising a 8-hydroxyquinoline aluminum complex as a host compound which is doped with quinacridone type dye (for example, JP-A No. 3-255190).

In the case of utilizing emission from an excited singlet as described above, since a generation ratio of a singlet exciton to a triplet exciton is 1/3, that is, a generation probability of an emitting exciton species is 25% and a light taking out efficiency is approximately 20%, the limit of an external quantum efficiency ($\eta$ext) of taking out light is said to be 5% at maximum.

However, since an organic EL element which utilizes phosphorescence from an excited triplet has been reported from Princeton University (M. A. Baldo et. al., Nature vol. 395, pp. 151-154 (1998)), researches on materials exhibiting phosphorescence at room temperature have come to be active.

For example, it is also disclosed in A. Baldo et al. Nature, vol. 403, No. 17, pp. 750-753 (2000), and U.S. Pat. No. 6,097,147.

Since the upper limit of internal quantum efficiency becomes 100% by utilization of an excited triplet which is principally 4 times of the ease of an excited singlet, it may be possible to achieve almost the same ability as a cooled cathode ray tube to attract attention also for an illumination application.

For example, in S. Lamansky et al., J. Am. Chem. Soc., vol. 123, p. 4304 (2001), many dopants mainly belonging to transition metal complexes such as iridium complexes and platinum complexes have been investigated.

Further, in the aforesaid, A. Baldo et al. Nature, vol. 403, No. 17, pp. 750-753 (2000), utilization of tris(2-phenylpyridine)iridium as a dopant (it is also called as a light emitting material) has been studied.

In addition to these, M. E. Tompson et al., at The 10th International Workshops on Inorganic and Organic Electroluminescence (EL'00, Hamamatsu), have studied to utilize $L_2Ir$ (acac) such as $(ppy)_2Ir(acac)$ as a dopant, Moon-Jae Youn. Og., Tetsuo Tsutsui et al., also at The 10th International Workshops on Inorganic and Organic Electroluminescence (EL'00, Hamamatsu), have studied utilization of such as tris (2-(p-tolyl)pyridine)iridium $(Ir(ptpy)_3)$ and tris(benzo[h]quinoline)iridium $(Ir(bzq)_3)$ (herein, these metal complexes are generally referred to as orthometalated iridium complexes.).

Further, in the aforesaid, S. Lamansky et al., J. Am. Chem. See, vol. 123, p. 4304 (2001), or in JP-A No. 2001-247859, studies have been carried out to prepare an element utilizing various types of iridium complexes.

As will be mentioned later, these complexes are used by being dispersed and added with a light emitting host material (or simply, it is called as a host) in a light emitting layer. And these complexes are called as a phosphorescent dopant.

Since the properties (light emitting efficiency, light emitting lifetime and light emission color) of an organic EL element will be largely changed not only by the dopant but by the host, the development of the dopant and the host have been extensively carried out.

For example, in order to obtain high emission efficiency, Ikai et al., at The 10th International Workshops on Inorganic and Organic Electroluminescence (EL'00, Hamamatsu) utilized a hole transporting compound as a host of a phosphorescent compound. Further, M. E. Tompson et al. utilized various types of electron transporting materials as a host of a phosphorescent compound doped with a new iridium complex.

In any cases, by suitably selecting a dopant and a host, emission luminance, and emission efficiency are significantly improved compared to conventional elements because the emitting light arises from phosphorescence. However, there has been a problem of a poor emission lifetime of the element compared to conventional phosphorescence type elements.

In particular, in the case of a blue light emitting element, she luminescence lifetime becomes extremely short, and the blue dopant which satisfied all requirements of luminescence efficiency, luminescence wavelength, and luminescence lifetime has not yet been found out, and the creation of such dopant is an urgent need.

As a blue phosphorescent dopant, it is known to introduce an electro negative group as a substituent in a phenyl pyridine group. Examples of such group are: a fluorine atom, a trifluoromethyl group and a cyano group. And it is also known to introduce picolinic acid or a pyrazabole system as a ligand.

However, by the complexes which use these ligands, it can be realized a blue luminescence by achieving shortening of luminescence wavelength, and it can achieve efficient luminescence. On the other hand, a luminescence lifetime of an element was very short. Improvement of trade-off of shortening of luminescence wavelength and luminescence lifetime has been required.

On the other hand, as a new development, it is known feat a metal complex which has a phenylpyrazole ligand can apply for producing blue phosphorescent luminescence.

However, it is known that an iridium complex having a simple pyrazole ligand does not emit light at room temperature, but emits light only after introducing a group which reduces a band gap in a substituent (refer to Patent document 6, for example).

However, this method did not improve the above-mentioned trade-off. After all, in order to improve luminescence property and luminescence lifetime, it is required to extend π-conjugated system to result in a long luminescence wavelength. Consequently, this method did not satisfy the requirements for blue phosphorescent dopant.

It is disclosed that a metal complex containing a phenylimidazole ligand is a light emitting material having a comparatively shortwave luminescence wavelength (refer to Patent documents 2 and 3, for example).

However, there remains a large problem at a present time when further shortening of wavelength and extension of lifetime are requested.

It is disclosed that a metal complex containing a phenylimidazole ligand has a comparatively short luminescence wavelength luminescent material (refer to Patent documents 4 and 5, for example).

However, there remains a large problem at a present time when low electric power consumption and extension of lifetime are requested.

Thus, it is the most difficult work for a phosphorescent dopant to simultaneously satisfy the requirements of (a) high emission property; (b) emission at short wavelength; and (c) extension of lifetime (it is also called high durability).

Among the efforts, it was reported that it was principally efficient to increase the transition probability from a metal portion, to a ligand portion in a metal complex with respect to high emission property (to enhance "Metal-to-ligand charge transfer (MLCT)") (refer to Non-patent documents 1 and 2, for example).

As one of the enhancing means of MLCT property, there was carried out a study to incorporate a substituent having a vacant orbital such as an arylboryl group in a ligand (refer to Non-patent document 3, for example).

In this document, an absorption derived from MLCT and light emission cased by photoexcitation were observe by introducing a triaryl boryl group in a ter-pyridine-Pt complex, which usually does not emit light even with photoexcitation.

Moreover, apart from the different viewpoint from this, it was disclosed that an element achieving high color purity due to the inhibition of broadening of emission wave shape with highly effective was obtained by introducing a boron containing substituent in a phenyl pyridine ligand (refer to Patent document 1).

However, the above-mentioned patent documents mainly aimed at achieving longer wavelength of emission. Our investigation revealed that it cannot realize blue emission by using these metal complexes, and emission lifetime cannot be extended. They are the problems to be solved for future element development.

PRIOR ART DOCUMENTS

Patent Documents

Patent document 1; Japanese Patent Application Publication (JP-A) No. 2004-315509
Patent document 2: WO 2006/046980
Patent document 3: US 2006/0251923
Patent document 4: WO 2007/095118
Patent document 5: WO 2008/156879
Patent document 6; WO 2004/085450

Non-Patent Documents

Non-patent document 1: Inorg. Chem., 2005, 14(13), 4737-4746
Non-patent document 2: Inorg. Chem., 2006, 45(22), 8907-8921
Non-patent document 3: Inorg. Chem., 2006, 45(26), 10670-10677

SUMMARY OF THE INVENTION

Problems to be Solved by the Invention

An object of the present invention is to provide an organic EL element exhibiting emission of short wavelength, high emission efficiency, as well as long lifetime, in particular, to provide an organic EL element including a phosphorescent light emitting material of short lifetime, and exhibiting high emission efficiency, as well as long lifetime.

Further, an object of the present invention is to provide a lighting device and a display device incorporating an organic EL element of the present invention.

Means to Solve the Problems

An object of the present invention described above has been achieved by the following constitutions.
1. An organic electroluminescence material being a compound represented by Formula (1).

Formula (1)

In the formula, A and B each represent a 6-membered aromatic hydrocarbon group, or a 5- or 6-membered aromatic heterocyclic group, provided that at least one of A and B represents a 5-membered aromatic heterocyclic group. Q represents a substituent having a vacant orbital which is capable of accepting a π electron from A or B. M represents a transition metal element belonging to groups 8 to 10 in the periodic table, and L represents a ligand which is capable of coordinating with M. m1 is an integer of 1 to 3, and m2 is an integer of 0 to 2. n is an integer of 1 to 4.

2. The organic electroluminescence material of the aforesaid item 1,
wherein the compound represented by Formula (1) is further represented by Formula (2).

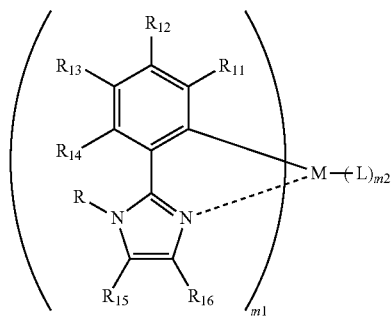

Formula (2)

In the formula, R represents an alkyl group, a cycloalkyl, an aromatic hydrocarbon group, or an aromatic heterocyclic group. $R_{11}$ to $R_{16}$ each represent a hydrogen atom or a substituent, provided that at least one of $R_{11}$ to $R_{16}$ represents the substituent Q having a vacant orbital which is capable of accepting a π electron from a bonded ring. M represents a transition metal element belonging to groups 8 to 10 in the periodic table, and L represents a ligand which is capable of coordinating with M. m1 is an integer of 1 to 3, and m2 is an integer of 0 to 2.

3. The organic electroluminescence material of the aforesaid item 1,
wherein the compound represented by Formula (1) is further represented by Formula (3).

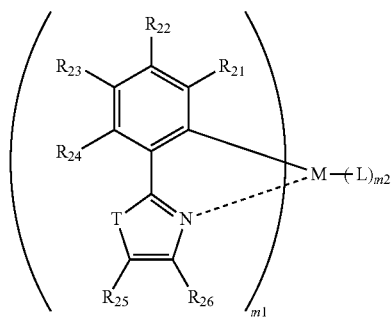

Formula (3)

In the formula, T represents an oxygen atom or a sulfur atom. $R_{21}$ to $R_{26}$ each represent a hydrogen atom or a substituent, provided that at least one of $R_{21}$ to $R_{26}$ represents file substituent Q having a vacant orbital which is capable of accepting a π electron from a bonded ring. M represents a transition metal element belonging to groups 8 to 10 in the periodic table, and L represents a ligand which is capable of coordinating with M. m1 is an integer of 1 to 3, and m2 is an integer of 0 to 2.

4. The organic electroluminescence material of the aforesaid item 1
wherein the compound represented by Formula (1) is further represented by Formula (4).

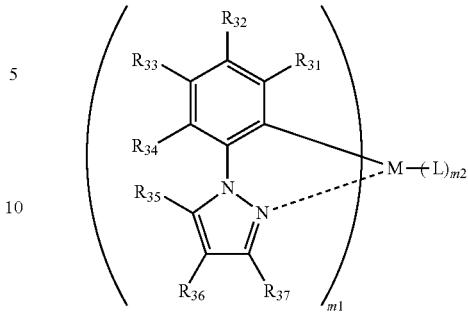

Formula (4)

In the formula, $R_{31}$ to $R_{37}$ each represent a hydrogen atom or a substituent, provided that at least one of $R_{31}$ to $R_{37}$ represents the substituent Q having a vacant orbital which is capable of accepting a π electron from a bonded ring. M represents a transition metal element belonging to groups 8 to 10 in the periodic table, and L represents a ligand which is capable of coordinating with M. m1 is an integer of 1 to 3, and m2 is an integer of 0 to 2.

5. The organic electroluminescence material of the aforesaid item 1,
wherein the compound represented by Formula (1) is further represented by Formula (5).

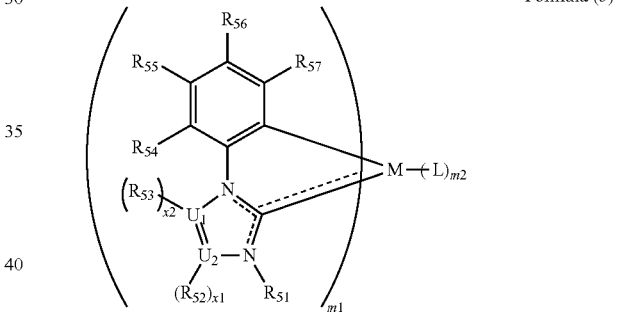

Formula (5)

In the formula, $R_{51}$ to $R_{57}$ each represent a hydrogen atom or a substituent, provided that at least one of $R_{51}$ to $R_{57}$ represents the substituent Q having a vacant orbital which is capable of accepting a π electron from a bonded ring. $U_1$ and $U_2$ each represent a carbon atom or a nitrogen atom. M represents a transition metal element belonging to groups 8 to 10 in the periodic table, and L represents a ligand which is capable of coordinating with M. m1 is an integer of 1 to 3, and m2 is an integer of 0 to 2. x1 and x2 each represent an integer of 0 or 1.

6. The organic electroluminescence material of the aforesaid item 2,
wherein at least one of $R_{11}$ and $R_{16}$ in the compound represented by Formula (2) represents the substituent Q.

7. The organic electroluminescence material of the aforesaid item 2,
wherein, at least one of $R_{11}$ to $R_{14}$ in the compound represented by Formula (2) represents the substituent Q.

8. The organic electroluminescence material of the aforesaid item 6,
wherein $R_{13}$ in the compound represented by Formula (2) represents the substituent Q.

9. The organic electroluminescence material of the aforesaid item 3, wherein at least one of $R_{25}$ and $R_{26}$ in the compound represented by Formula (3) represents the substituent Q.

10. The organic electroluminescence material of the aforesaid item 3,
    wherein at least one of $R_{21}$ to $R_{24}$ in the compound represented by Formula (3) represents the substituent Q.

11. The organic electroluminescence material of the aforesaid item 9,
    wherein $R_{23}$ in the compound represented by Formula (3) represents the substituent Q.

12. The organic electroluminescence material of the aforesaid item 4,
    wherein at least one of $R_{35}$ to $R_{37}$ in the compound represented by Formula (4) represents the substituent Q.

13. The organic electroluminescence material of the aforesaid item 4,
    wherein at least one of $R_{31}$ to $R_{34}$ in the compound represented by Formula (4) represents the substituent Q.

14. The organic electroluminescence material of the aforesaid item 12,
    wherein $R_{33}$ in the compound represented by Formula (4) represents the substituent Q.

15. The organic electroluminescence material of the aforesaid item 5,
    wherein at least one of $R_{51}$ to $R_{53}$ in the compound represented by Formula (5) represents the substituent Q.

16. The organic electroluminescence material of the aforesaid item 5,
    wherein at least one of $R_{54}$ to $R_{57}$ in the compound represented by Formula (5) represents the substituent Q.

17. The organic electroluminescence material of the aforesaid item 16,
    wherein $R_{55}$ in the compound represented by Formula (5) represents the substituent Q.

18. The organic electroluminescence material of any one of the aforesaid items 1 to 17,
    wherein in the compound represented by Formula (1) of the aforesaid item 1, in the compound represented by Formula (2) of the aforesaid item 2, in the compound represented by Formula (3) of the aforesaid item 3, in the compound represented by Formula (4) of the aforesaid item 4, or in the compound represented by Formula (5) of the aforesaid item 5, the substituent Q is a substituent containing an element belonging to group 13 in the periodic table, a sulfur atom or a phosphor atom.

19. The organic electroluminescence material of the aforesaid item 18,
    wherein the substituent Q represents one of Q-1, Q-2 and Q-3.

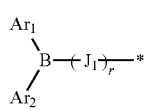

Q-1

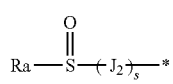

Q-2

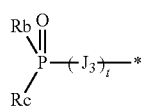

Q-3

In the formulas, $Ar_1$ and $Ar_2$ each respectively represent an aromatic hydrocarbon ring group or an aromatic heterocyclic group, provided that $Ar_1$ and $Ar_2$ may be joined to form an aromatic ring. Ra, Rb and Rc each represent an alkyl group, a cycloalkyl group, an aromatic hydrocarbon ring group or an aromatic heterocyclic group. $J_1$, $J_2$ and $J_3$ each represent an arylene group or a heteroarylene group. r, s and t each represent an integer of 0 or 1.

20. The organic electroluminescence material of the aforesaid item 19,
    wherein the substituent Q represents one selected from the group consisting of Q-1-1 to Q-1-10.

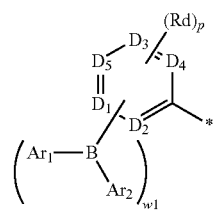

Q-1-1

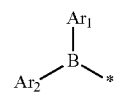

Q-1-2

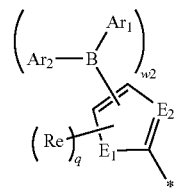

Q-1-3

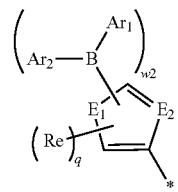

Q-1-4

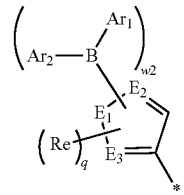

Q-1-5

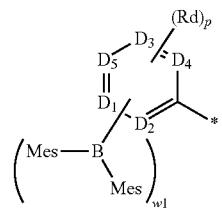

Q-1-6

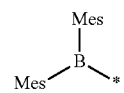

Q-1-7

-continued

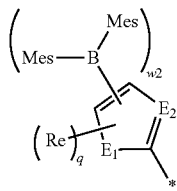
Q-1-8

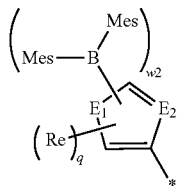
Q-1-9

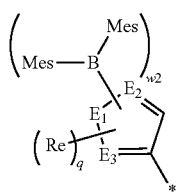
Q-1-10

In the formulas, $Ar_1$ and $Ar_2$ each respectively represent an aromatic hydrocarbon ring group or an aromatic heterocyclic group, provided that $Ar_1$ and $Ar_2$ may be joined to form an aromatic ring. $D_1$ to $D_5$ each represent a carbon atom or a nitrogen atom. Rd and Re each represent an alkyl group, a cycloalkyl group, an aromatic hydrocarbon ring group or an aromatic heterocyclic group. p represents an integer of 0 to 4, and q represent an integer of 0 to 2. $E_1$ represents O, S or N-Rf (provided that Rf represents an alkyl group, a cycloalkyl group, an aromatic hydrocarbon ring group or an aromatic heterocyclic group). $E_2$ and $E_3$ each represent a carbon atom or a nitrogen atom. Mes represents a mesityl group. W1 represents an integer of 1 to 5, and W2. represents an integer of 1 to 3.

21. The organic electroluminescence material of any one of the aforesaid items 1 to 20,
    wherein in the compound represented by Formula (1) of the aforesaid item 1, in the compound represented by Formula (2) of the aforesaid item 2, in the compound represented by Formula (3) of the aforesaid item 3, in the compound represented by Formula (4) of the aforesaid item 4, or in the compound represented by Formula (5) of the aforesaid item 5. M represents a platinum atom or an iridium atom.
22. An organic electroluminescence element comprising at lest one light emitting layer sandwiched between an anode and a cathode,
    wherein the light emitting layer contains at least one compound represented by Formula (1) of the aforesaid item 1.
23. The organic electroluminescence element of the aforesaid item 22,
    wherein the compound represented by Formula (1) is a compound represented by Formula (2) of the aforesaid item 2.
24. The organic electroluminescence element of the aforesaid item 22,
    wherein the compound represented by Formula (1) is a compound represented by Formula (3) of the aforesaid item 3.
25. The organic electroluminescence element of the aforesaid item 22,
    wherein the compound represented by Formula (1) is a compound represented by Formula (4) of the aforesaid item 4.
26. The organic electroluminescence element of the aforesaid item 22,
    wherein the compound represented by Formula (1) is a compound represented by Formula (5) of the aforesaid item 5.
27. The organic electroluminescence element of the aforesaid item 23,
    wherein at least one of $R_{15}$ and $R_{16}$ in the compound represented by Formula (2) represents the substituent Q.
28. The organic electroluminescence element of the aforesaid item 23,
    wherein at least one of $R_{11}$ to $R_{16}$ in the compound represented by Formula (2) represents the substituent Q.
29. The organic electroluminescence element of the aforesaid item 28,
    wherein $R_{13}$ in the compound represented by Formula (2) represents the substituent Q.
30. The organic electroluminescence element of the aforesaid item 24,
    wherein at least one of $R_{25}$ and $R_{26}$ in the compound represented by Formula (3) represents the substituent Q.
31. The organic electroluminescence element of the aforesaid item 24,
    wherein at least one of $R_{21}$ to $R_{24}$ in the compound represented by Formula (3) represents the substituent Q.
32. The organic electroluminescence element of the aforesaid item 31,
    wherein $R_{23}$ in the compound represented by Formula (3) represents the substituent Q.
33. The organic electroluminescence element of the aforesaid item 25,
    wherein, at least one of $R_{35}$ to $R_{37}$ in the compound represented by Formula (4) represents the substituent Q,
34. The organic electroluminescence element of the aforesaid item 25,
    wherein at least one of $R_{31}$ to $R_{34}$ in the compound represented by Formula (4) represents the substituent Q.
35. The organic electroluminescence element of the aforesaid item 34,
    wherein $R_{33}$ in the compound represented by Formula (4) represents the substituent Q.
36. The organic electroluminescence element of the aforesaid item 26,
    wherein at least one of $R_{51}$ to $R_{53}$ in the compound represented by Formula (5) represents the substituent Q.
37. The organic electroluminescence element of the aforesaid item 26,
    wherein at least one of $R_{54}$ to $R_{57}$ in the compound represented by Formula (5) represents the substituent Q,
38. The organic electroluminescence element of the aforesaid item 37,
    wherein $R_{55}$ in the compound represented by Formula (5) represents the substituent Q.
39. The organic electroluminescence element of any one of the aforesaid items 22 to 38,
    wherein in the compound represented by Formula (1) of the aforesaid item 1, in the compound represented by Formula (2) of the aforesaid item 2, in the compound represented by Formula (3) of the aforesaid item 3, in the compound represented by Formula (4) of the aforesaid item 4, or in the compound represented by Formula (5) of the aforesaid item 5, the substituent Q is a substituent containing an element belonging to group 13 in the periodic table, a sulfur atom or a phosphor atom.
40. The organic electroluminescence element of the aforesaid item 39,
wherein the substituent Q is selected from the partial structures of the aforesaid item 19.
41. The organic electroluminescence element of the aforesaid item 40,
wherein the substituent Q is selected from the partial structures of the aforesaid item 20.
42. The organic electroluminescence element of any one of the aforesaid items 22 to 41,
wherein in the compound represented by Formula (1) of the aforesaid item 1, in the compound represented by Formula (2) of the aforesaid item 2, in the compound represented by Formula (3) of the aforesaid item 3, in the compound represented by Formula (4) of the aforesaid item 4, or in the compound represented by Formula (5) of the aforesaid item 5, the aforesaid M represents a platinum atom or an iridium atom.
43. The organic electroluminescence element of any one of the aforesaid items 22 to 42,
comprising an organic layer containing at least one compound represented by Formula (1) of the aforesaid item 1, Formula (2) of the aforesaid item 2, Formula (3) of the aforesaid item 3, Formula (4) of the aforesaid item 4, or Formula (5) of the aforesaid item 5; and
the aforesaid organic layer is formed with a wet process.
44. A display device comprising the organic electroluminescence element of any one of the aforesaid items 22 to 43.
45. A lighting device comprising the organic electroluminescence element of any one of the aforesaid items 22 to 43.

EFFECTS OF THE INVENTION

In an organic electroluminescence material of the present invention, it was able to provide an organic EL element exhibiting high, emission efficiency, as well as long lifetime by any one of the embodiments described in claims 1-21.

Further, it was able to provide a lighting device and a display device incorporating an organic EL element of the present, invention.

PREFERRED EMBODIMENTS TO CARRY OUT THE INVENTION

Figure 1:
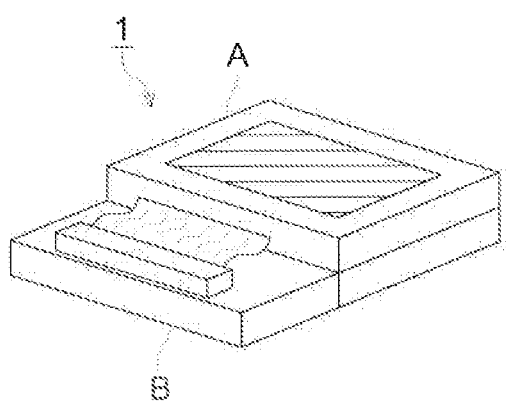
FIG. 1 is a schematic drawing to show an example of a display device of the present invention.

The present inventors extensively investigated various types of ligands used tor formation of a metal complex in the above technical background with the aim of increase MLCT property. As a result, the present inventors found out the following. The MLCT property can be increased by introducing a substituent having a vacant orbital which is capable of accepting a π electron such as a boron atom or a phosphine oxide group into a ligand structure such as phenyl pyrazole or phenyl imidazole. Consequently, emission property and stability of the complex can be improved. Further, the emission wavelength can be adjusted to a required wavelength region by suitably adjusting the kind and the substitution position of the substituent.

It can be said that the above-mentioned knowledge (technology) which was acquired by present inventors is effective universal technology applicable to future progress in organic electroluminescence technology.

Hereafter, the details of each constituent element concerning the present invention will be explained successively.

<<Organic Electroluminescence Element Material>>

An organic electroluminescence material of the present invention will be described.

An organic electroluminescence element material is a compound represented by Formula (1), and this compound belongs to a category of a metal complex (a metal complex compound) from the viewpoint of chemical structure.

The present inventors made attention to an organic electroluminescence element material used in a light emitting layer of an organic EL element, and investigated various types of metal complex compounds especially used as a light emitting dopant.

In a previously known metal complex compound having a phenylpyrazole structure, a short wavelength emission can be observed, but that emission was very weak or not detected at room temperature. This is occurred from the case controlled by so-called non-radiative deactivation. Among them, the present inventors investigated by using a molecular orbital calculation. It was found out that a metal complex compound having a ligand structure containing a specific structure or a specific substituent exhibits a short wavelength emission with high emission strength.

An example of the findings is as follows. By introducing into a ligand a substituent containing an element belonging to group 13 in the periodic table, a sulfur atom or a phosphor atom, a π electron in a metal oxide complex is accommodated, and at the same time, a σ electron is afforded from a substituent to a ligand to produce a back-donation effect. This enables to achieve compatibility of both increasing an emission property and establishing stability, which is hardly achieved by only introduction of an electro negative group in a ligand.

As a substituent showing a back-donation effect, preferable is a substituent having a vacant p orbital which is capable of accepting a π electron from a ligand.

Examples of a preferable substituent will be detailed in the later portion of describing Q.

The present inventors further continued investigation and found out the following. It was developed a compound (it is also called as: a metal complex or a metal complex compound) represented by Formulas (1), (2), (3), (4) or (5), which is an organic EL element material of the present invention. When this compound was applied to an organic EL element, the element exhibited a required emission wavelength and realized a long lifetime. Thus, a new dopant was successively developed.

Further, in any compound represented by Formulas (1), (2), (3), (4) or (5), it was also found out that an emission wavelength can be controlled to be in a required range by tuning a ligand used for formation of a metal complex, an assisting ligand or a substituent.

Consequently, a molecular design to give a function to control an emission wavelength in a required range (from green to red) can be done by using a compound represented by Formulas (1), (2), (3), (4) or (5) relating to the present invention as a starting point of a basic structural design.

A compound (a metal complex) represented by Formulas (1), (2), (3), (4) or (5) relating to the present invention may contain a plurality of ligands depending on a valence of a transition metal represented by M. These ligands may be the same or may have a different structure with each other.

The kinds of ligands in the complex are preferably one or two kinds from the viewpoints of obtaining an effect of the present invention. More preferably, it is one kind of ligand.

Especially preferable is a compound containing a ligand made of a portion of a compound (a metal complex) represented by Formulas (1), (2), (3), (4) or (5) relating to the present invention, the portion being eliminated a transition metal represented by M and a ligand represented by L from the compound represented by Formulas (1), (2), (3), (4) or (5).

Here, the especially preferable ligand is composed of a portion which is produced by eliminating a transition metal represented by M and a ligand represented by L from the compound represented by Formulas (1), (2), (3), (4) or (5).

A conventionally known ligand which can be used for formation of a metal complex relating to the present invention will be detailed later.

Among the compounds (metal complexes) containing a partial structure represented by Formula (1), a compound (a metal complex) represented by Formulas (2), (3), (4) or (5) is preferable.

By using the above-mentioned metal complex as an organic EL element material, it was possible to provide an organic EL element exhibiting high emission efficiency and having a long lifetime, a lighting device and a display device.

In a constituting layer of an organic EL element of the present invention, it is preferable to incorporate a compound (a metal complex) represented by Formulas (1), (2), (3), (4) or (5) relating to the present invention in a charge transport layer.

<<Charge Transport Layer>>

A charge transport layer of the present invention will be described.

As a containing layer of a compound (a metal complex) represented by Formulas (1), (2), (3), (4) or (5) relating to the present invention, there is no specific limitation as long as it is a layer which transports a charge (a charge transport layer). A charge transport layer may have both embodiments: a case in which a charge transport layer is located in a place nearer to an anode side than a light emitting layer (it is called as "a first charge transport layer"); and a case in which a charge transport layer is located in a place nearer to a cathode side than a light emitting layer (it is called as "a second charge transport layer").

In the case in which a charge transport layer is located in a place nearer to an anode side than a light emitting layer (it is called as "a first charge transport layer"), the aforesaid charge transport layer is preferably an electron blocking layer or a light emitting layer. In the case in which a charge transport layer is located in a place nearer to a cathode side than a light emitting layer (it is called as "a second charge transport layer"), the aforesaid charge transport layer is preferably a light emitting layer or a hole blocking layer. More preferably, the aforesaid charge transport layer is a light emitting layer or a hole blocking layer. And still more preferably, the aforesaid charge transport layer is a light emitting layer.

When it is contained in a light emitting layer, it is possible to achieve increase of an external taking out quantum efficiency and longer lifetime of an organic EL element of the present invention by employing as a light emitting dopant in a light emitting layer.

In addition, the constituting layers of an organic EL element of the present invention will be detailed later.

Hereafter, a compound (a metal complex) represented by any one of Formulas (1), (2), (3), (4) and (5) relating to the present invention will be described.

<<Compound (metal complex) Represented by Formula (1)>>

A compound represented by Formula (1) relating to the present invention will be described.

In Formula (1), as a 6-membered aromatic hydrocarbon group represented by A or B, examples thereof include; a phenyl group, p-chlorophenyl group, a mesityl group, a tolyl group, a xylyl group, a naphtyl group, an anthryl group, an azulenyl group, an acenaphthenyl group, a fluorenyl group, a phenanthryl group, an indenyl group and a biphenyl group.

In Formula (1), as a 6-membered aromatic heterocyclic group represented by A or B, examples thereof include: a pyridyl group, a pyrimidinyl group, a pyradinyl group and a triazinyl group.

In Formula (1), as a 5-membered aromatic heterocyclic group represented by A or B, examples thereof include: a furyl group, a pyrrolyl group, an imidazolyl group, a pyrazolyl group, a pyrazinyl group, a triazolyl group (for example, 1,2,4-triazole-1-yl group and 1,2,3-triazole-1-yl group), an oxazolyl group, a thiazoiyl group, an isooxazolyl group, an isothiazolyl group, a furazanyl group, a thienyl group and an imidazolinium carbenium group.

In Formula (1), a 6-membered aromatic hydrocarbon group and a 5- or 6-membered aromatic heterocyclic group represented by A and B may have a substituent respectively. Examples of a substituent include: an alkyl group (for example, a methyl group, an ethyl group, a propyl group, an isopropyl group, a tert-butyl group, a pentyl group, a hexyl group, an octyl group, a dodecyl group, a tridecyl group, a tetradecyl group, and a pentadecyl group); a cycloalkyl group (for example, a cyclopentyl group, and a cyclohexyl group); an alkenyl group (for example, a vinyl group, an allyl group, 1-propenyl group, 2-butenyl group, 1,3-butadienyl group, 2-pentenyl group and iso-propenyl group); an alkynyl group (for example, an ethynyl group and a propargyl group); an aromatic hydrocarbon group (also called an aromatic carbon ring, an aromatic carbon ring group or an aryl group, for example, a phenyl group, a p-chlorophenyl group, a mesityl group, a tolyl group, a xylyl group, a naphtyl group, an anthryl group, an azulenyl group, an acenaphthenyl group, a fluorenyl group, a phenantolyl group, an indenyl group, a pyrenyl group, and a biphenyxyl group); an aromatic heterocyclic group (for example, a furyl group, a thienyl group, a pyridyl group, a pyridazinyl group, a pyrimidinyl group, a pyrazinyl group, a triazinyl group, group, an imidazolyl group, a pyrazolyl group, a thiazolyl group, a quinazolinyl group, a carbazolyl group, a carbolinyl group, a diazacarbazolyl group (indicating a ring structure in which one of the carbon atoms constituting the carboline ring of the carbolinyl group is replaced with nitrogen atoms), and a phthalazinyl group); a heterocyclic group (for example, a pyrrolidyl group, an imidazolidyl group, a morpholyl group, and anoxazolidyl group); an alkoxyl group (for example, a methoxy group, an ethoxy group, a propyloxy group, a pentyloxy group, an hexyloxy group, an octyloxy group, and a dodecyloxy group); a cycloalkoxy group (for example, a cyclopentyloxy group and a cyclohexyloxy group); an aryloxy group (for example, a phenoxy group and a naphthyloxy group); an alkylthio group (for example, a methylthio group, an ethylthio group, a propylthio group, a pentylthio group, hexylthio group, an octylthio group, and a dodecylthio group); a cycloalkylthio group (for example, a cyclopentylthio group and a cyclohexylthio group); an arylthio group (for example, a phenylthio group and a naphthylthio group); an alkoxycarbonyl group (for example, a methyloxycarbonyl group, an ethyloxycarbonyl group, a butyloxycarbonyl group, an octyloxycarbonyl group, and a dodecyloxycarbonyl group); an aryloxycarbonyl group (for example, a phenyloxycarbonyl group and a naphthyloxycarbonyl group); a sulfamoyl group (for example, an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, and a 2-pyridylaminosulfonyl group); an acyl group (for example, an acetyl group, an ethyl carbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, and a pyridylcarbonyl group); an acyloxy group (for example, an acetyloxy group, an ethylcarbonyloxy group, a butylcarbonyloxy group, an octylcarbonyloxy group, a dodecylcarbonyloxy group, and a phenylcarbonyloxy group); an amido group (for example, a methylcarbonylamino group, an ethylcarbonylamino group, a dimethylcarbonylamino group, a propylcarbonylamino group, a pentylcarbonylamino group, a cyclohexylcarbonylamino group, a 2-ethyhexylcarbonylamino group, an octylcarbonylamino group, a dodecylcarbonylamino group, a phenylcarbonylamino group, and a naphthylcarbonylamino group); a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethymexylaminocarbonyl group, a dodecylaminocarbonyl group, a phenylaminocarbonyl group, a naphthylaminocarbonyl group, and a 2-pyridylaminocarbonyl group); a ureido group (for example, a methylureido group, an ethylureido group, a pentylureido group, a cyclohexylureido group, an octylureido group, a dodecylureido group, a phenylureido group, a naphthylureido group, and a 2-oyridylaminoureido group); a sulfinyl group (for example, a methylsulfinyl group, an ethylsufinyl group, a butylsulfinyl group, a cyclohexylsulfinyl group, a 2-ethylhexylsulfinyl group, a dodecylsulfinyl group, a phenylsulfinyl group, a naphthylsulfinyl group, and a 2-pyridylsdfinyl group); an alkylsulfonyl group (for example, a methylsulfonyl group, an ethylsulfonyl group, a butylsulfinyl group, a cyclohexylsulfonyl group, a 2-ethylhexylsulfonyl group, and a dodecylsulfonyl group, an arylsulfonyl group or a heteroarylsulfonyl group (for example, a phenylsulfonyl group, a naphthylsulfonyl group, and a 2-pyridylsulfonyl group); an amino group (for example, an amino group, an ethylamino group, a dimethylamino group, a butylamino group, a cyclopentylamino group, a dodecylamino group, an anilino group, a naphthylamino group, and a 2-pyridylamino group); a halogen atom (for example, a fluorine atom, a chlorine atom and a bromine atom); a fluorinated hydrocarbon group (for example, a fluoromethyl group, trifluoromethyl group, a pentafluoroethyl group and a pentafluorophenyl group); a cyano group; a nitro group; a hydroxyl group; a mercapto group; a silyl group (for example, a trimethylsilyl group, a triisopropylsilyl group, a triphenylsilyl group, and a phenyldiethylsilyl group) and a phosphoric group.

Moreover, these substituents may be further substituted by the above-mentioned substituent. Further, a plurality of these substituents may combine with each other to form a ring.

In Formula (1), as a substituent represented by Q having a vacant orbital which is capable of accepting a π electron form A or B, it is preferable a substituent containing an element belonging to group 13 in the periodic table, a sulfur atom or a phosphor atom. More preferably, Q is represented by any one of Q-1, Q-2 and Q-3. Especially preferably, Q is a group selected from the group consisting Q-1-1 to Q-1-10.

(Groups represented by Q-1, Q-2 and Q-3)

In groups represented by Q-1, Q-2 and Q-3, examples of an aromatic hydrocarbon ring group each represented by $Ar_1$ and $Ar_2$ include: a phenyl group, p-chlorophenyl group, a mesityl group, a tolyl group, a xylyl group, a naphthyl group, an anthryl group, an azulenyl group, an acenaphthenyl group, a fluorenyl group, a phenanthryl group, an indenyl group, a phenyl group and a biphenyl group.

These groups may further have a substituent as described above.

In groups represented by Q-1, Q-2 and Q-3, examples of an aromatic heterocyclic group represented by $Ar_1$ and $Ar_2$ include: a pyridyl group, a pyrimidinyl group, a furyl group, a pyrrolyl group, an imidazolyl group, a benzoimidazolyl group, a pyrazolyl group, a pyrazinyl group, a triazolyl group (for example, 1,2,4-triazole-1-yl group and 1,2,3-triazole-1-yl group), an oxazolyl group, a benzoxazolyl group, a thiazolyl group, an isooxazolyl group, an isothiazolyl group, a furazanyl group, a thienyl group, a quinolyl group, a benzofuryl group, a dibenzofuryl group, a benzothienyl group, an indolyl group, a carbazolyl group, a carbolinyl group, a diazacarbazolyl group (indicating a ring structure in which one of the carbon atoms constituting the carboline ring of the carbolinyl group is replaced with nitrogen atoms), a quinoxalinyl group, a pyridazinyl group, a triazinyl group, a quinazolinyl group, and a phthalazinyl group.

These groups may further have a substituent as described above.

$Ar_1$ and $Ar_2$, shown in Q-1, Q-2 and Q-3, each may be joined to further form an aromatic ring. Examples of an aromatic ring include: an aromatic hydrocarbon ring (for example, a biphenyl ring a naphthalene ring, an azulene ring, an anthracene ring, a phenanthrene ring, a pyrene ring, a chrysene ring, a naphthacene ring, a triphenylene ring, an o-terphenyl ring, an m-terphenyl ring, a p-terphenyl ring an acenaphthene ring, a coronene ring, a fluorene ring, a fluoroanthrene ring a naphthacene ring, a pentacene ring, a perylene ring, a pentaphene ring, a picene ring, a pyrene ring, a pyranthrene ring, and an anthraanthrene ring); an aromatic heterocycle (for example, an aromatic heterocycle of a single ring (such as: a furan ring, a thiophene ring, an oxazole ring, a pyrrole ring, a pyridine ring, a pyridazine ring, a pyrimidine ring, a pyrazine ring, a triazine ring, a benzimidazole ring, an oxadiazole ring, a triazole ring, an imidazole ring, a pyrazole ring, and a thiazole ring) may further condensed with the same ring or with a different ring to form an aromatic heterocyclic ring. Moreover, it can be cited the following rings: an indole ring, an indazole ring, a benzimidazole ring, a benzothiaxole ring, a benzoxazole ring, quinoxaline ring, a quinazoline ring, a cinnoline ring, a quinoline ring, an isoquinoline ring, a phthalazine ring, a naphthyridine ring, a carbazole ring, a carboline ring, and a diazacarbazole ring (indicating a ring structure in which one of the carbon atoms constituting the carboline ring is replaced with nitrogen atoms).

In a group represented by Q-1, a preferably used aromatic ring formed by bonding $Ar_1$ and $Ar_2$ with each other is a 1H-borolyl group or 5H-dibenzoborolyl group.

In groups represented by Q-1, Q-2 and Q-3, examples of an alkyl group represented by Ra, Rb and Rc include: a methyl group, an ethyl group, a propyl group, an isopropyl group, a tert-butyl group, a pentyl group, a hexyl group, an octyl group, a dodecyl group, a tridecyl group, a tetradecyl group, and a pentadecyl group.

These groups may further have a substituent as described above.

In groups represented by Q-1, Q-2 and Q-3, examples of a cycloalkyl group represented by Ra, Rb and Rc include: a cyclopentyl group and a cyclohexyl group.

These groups may further have a substituent as described above.

In groups represented by Q-1, Q-2 and Q-3, examples of an aromatic hydrocarbon ring group represented by Ra, Rb and Rc include: a phenyl group, p-chlorophenyl group, a mesityl group, a tolyl group, a xylyl group, a naphtyl group, an anthlyl group, an azulenyl group, an acenaphthenyl group, a fluorenyl group, a phenanthryl group, an indenyl group, a pyrenyl group and a biphenyl group. Examples of an aromatic heterocyclic group include: a furyl group, a thienyl group, a pyridyl group, a pyridazinyl group, a pyrimidinyl group, a pyrazinyl group, a triazinyl group, group, an imidazolyl group, a pyrazolyl group, a thiazolyl group, a quinazolinyl group, a phthalazinyl group.

These groups may further have a substituent as described above.

In groups represented by Q-1, Q-2 and Q-3, examples of an aromatic heterocyclic group represented by Ra, Rb and Rc include; a furyl group, a thienyl group, a pyridyl group, a pyridazinyl group, a pyrimidinyl group, a pyrazinyl group, a triazinyl group, group, an imidazolyl group, a pyrazolyl group, a thiazoiyl group, a quinazolinyl group, a carbazolyl group, a carbolinyl group, a diazacarbazolyl group (indicating a ring structure in which one of the carbon atoms constituting the carboline ring of the carbolinyl group is replaced with nitrogen atoms), and a phthalazinyl group.

These groups may further have a substituent as described above.

In groups represented by Q-1, Q-2 and Q-3, examples of an arylene group represented by Ra, Rb and Rc include: o-phenylene group, m-phenylene group, p-phenylene group, a naphthalene-diyl group, an anthracene-diyl group, a naphthacene-diyl group, a pyrene-diyl group, a naphtylnaphthalene-diyl group, a biphenyl-diyl group (for example, [1,1'-biphenyl]-4,4'-diyl group, 3,3'-biphenyl-diyl group and 3,6-biphenyl-diyl group), terphenyl group, a quaterphenyl-diyl group, a quinquephenyl-diyl group, a sexiphenyl-diyl group, a septiphenyl-diyl group, an octiphenyl-diyl group, a noviphenyl-diyl group, and a deciphenyl-diyl group.

These arylene groups may have a substituent as described above.

In groups represented by Q-1, Q-2 and Q-3, examples of a heteroarylene group represented by Ra, Rb and Rc include a divalent group derived from: a carbazole ring, a carboline ring, a diazacarbazole ring (it is also called as a monoazacarboline ring, and it indicates a ring structure in which one of the carbon atoms constituting the carboline ring is replaced with nitrogen atoms), triazole ring, a pyrrole ring, a pyridine ring, a pyrazine ring, a quinoxaline ring, a thiophene ring, an oxadiazole ring, a dibenzofuran ring, a dibenzothiophene ring, and an indole ring.

These heteroarylene groups may have a substituent as described above.

(Groups each represented by Q-11-1 to Q-1-10)

In groups represented by Q-1-1 to Q-1-10, an aromatic hydrocarbon ring group each represented by $Ar_1$ and $Ar_2$ is synonymous with an aromatic hydrocarbon ring group each represented by $Ar_1$ and $Ar_2$ in the above-described Q-1, Q-2 and Q-3.

In groups each represented by Q-1-1 to Q-1-10, an aromatic heterocyclic group represented by $Ar_1$ and $Ar_2$ is synonymous with an aromatic heterocyclic group each represented by $Ar_1$ and $Ar_2$ in the above-described Q-1, Q-2 and Q-3.

In groups represented by Q-1-1 to Q-1-10, an aromatic ring group formed by bonding $Ar_1$ and $Ar_2$ with each other is synonymous with an aromatic ring group formed by bonding $Ar_1$ and $Ar_2$ with each other in the above-described Q-1, Q-2 and Q-3.

Further, in groups represented by Q-1-1 to Q-1-10, preferable examples of an aromatic ring formed by bonding $Ar_1$ and $Ar_2$ with each other include: a 1H-borolyl group and 5H-dibenzoborolyl group.

In groups represented by Q-1-1 to Q-1-10, an alkyl group each represented by Rd and Re is synonymous with an alkyl group each represented by Ra, Rb and Rc in the above-described Q-1, Q-2 and Q-3.

In groups represented by Q-1-1 to Q-1-10, a cycloalkyl group each represented by Rd and Re is synonymous with a cycloalkyl group each represented by Ra, Rb and Rc in the above-described Q-1, Q-2 and Q-3.

In groups represented by Q-1-1 to Q-1-10, an aromatic hydrocarbon ring group each represented by Rd and Re is synonymous with an aromatic hydrocarbon ring group each represented by Ra, Rb and Rc in the above-described Q-1, Q-2 and Q-3.

In groups represented by Q-1-1 to Q-1-10, an aromatic heterocyclic group each represented by Rd and Re is synonymous with an aromatic hydrocarbon ring group each represented by Ra, Rb and Rc in the above-described Q-1, Q-2 and Q-3.

In groups represented by Q-1-1 to Q-1-10, an alkyl group represented by Rf in N-Rf of $E_1$ is synonymous with an alkyl group each represented by Ra, Rb and Rc in the above-described Q-1, Q-2 and Q-3.

In groups represented by Q-1-1 to Q-1-10, a cycloalkyl group represented by Rf in N-Rf of $E_1$ is synonymous with a cycloalkyl group each represented by Ra, Rb and Rc in the above-described Q-1, Q-2 and Q-3.

In groups represented by Q-1-1 to Q-1-10, an aromatic hydrocarbon ring group represented by Rf in N-Rf of $E_1$ is synonymous with a cycloalkyl group each represented by Ra, Rb and Rc in the above-described Q-1, Q-2 and Q-3.

In groups represented by Q-1-1 to Q-1-10, an aromatic heterocyclic group represented by Rf in N-Rf of $E_1$ is synonymous with an aromatic heterocyclic group each represented by Ra, Rb and Rc in the above-described Q-1, Q-2 and Q-3.

Hereafter, specific examples of a substituent Q in Formula (1) relating to the present invention will be described, the substituent Q having a vacant orbital capable of accepting a π electron from A or B. The present invention will not be limited to these.

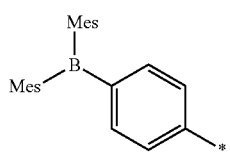

Q2 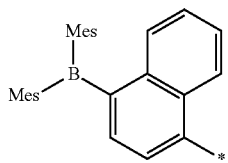
Q3 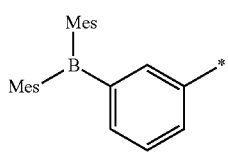
Q4 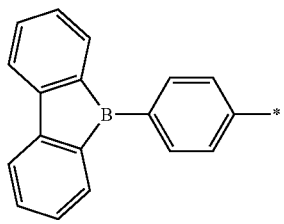
Q5 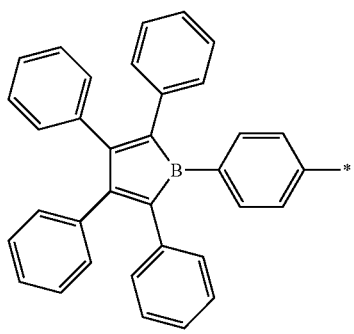
Q6 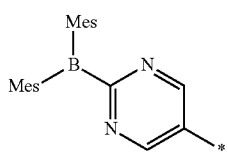
Q7 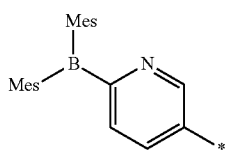
Q8 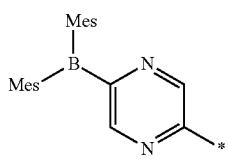
Q9 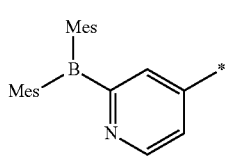
Q10 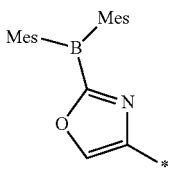
Q11 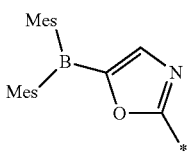
Q12 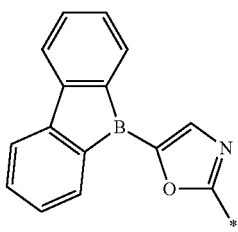
Q13 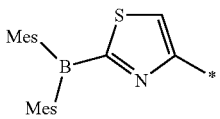
Q14 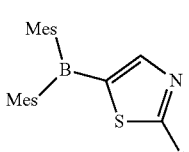
Q15 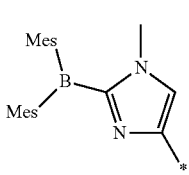
Q16 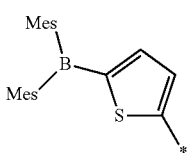
Q17 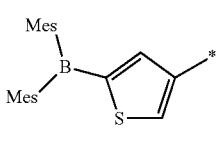
Q18 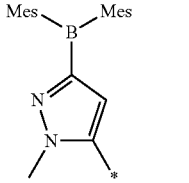

-continued
Q19 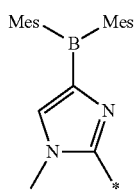
Q20 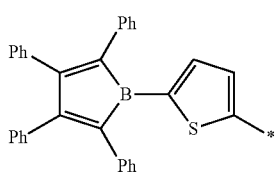
Q21 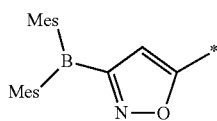
Q22 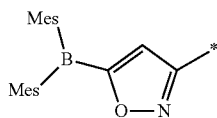
Q23 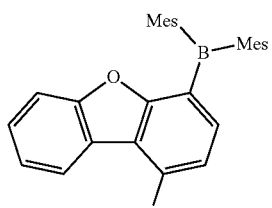
Q24 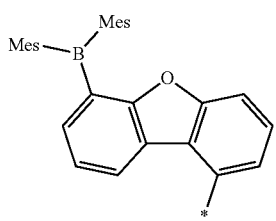
Q25 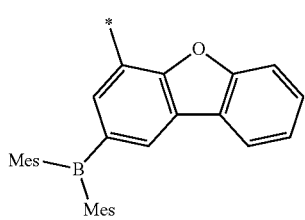
Q26 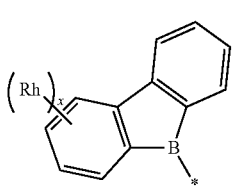
Q27 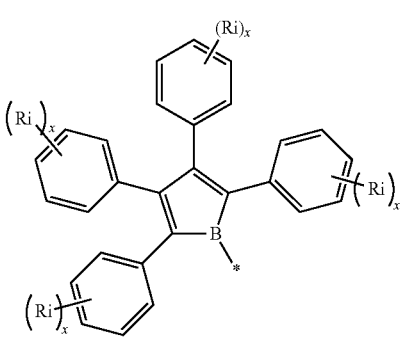
Q28 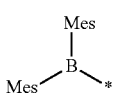
Q29 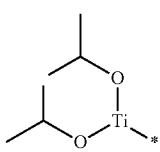
Q30 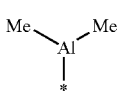
Q31 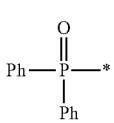
Q32 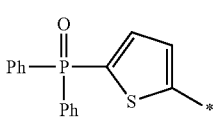
Q33 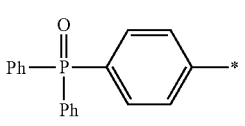
Q34 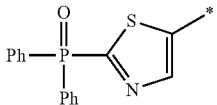
Q35 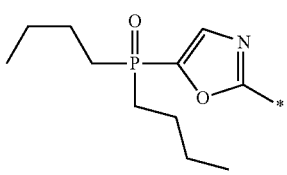
Q36 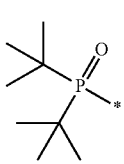

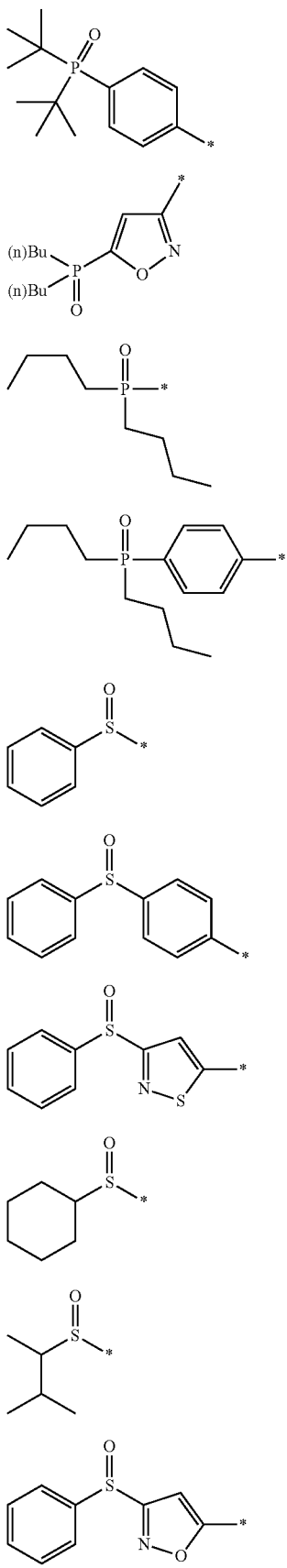

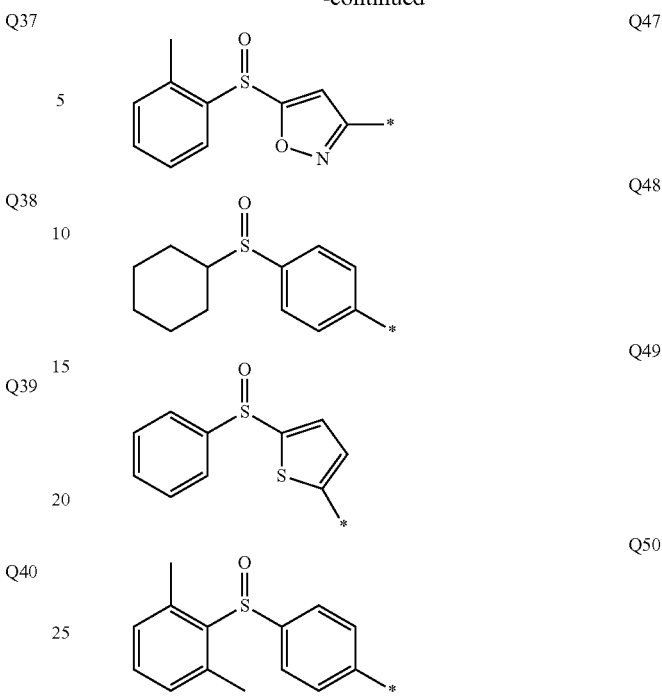

In Formula (1), L represents any ligand which can coordinate with M. This ligand is know to one having ordinary skill in the art. There are various publicly known ligands used for a ligand of a publicly known metal complex. Examples thereof include: ligands described in "Photochemistry and Photophysics of Coordination Compounds", Springer-Verlag, H. Yersin, in 1987; ligands described in "Organic metal chemistry: Basis and application" Shokaho, Akio Yamamoto, in 1982 (for example, a halogen ligand, preferably, a chlorine ligand); heterocyclic ligands (for example, a bipyridyl ligand and a phenanthroline ligand); and a diketone ligand. Further, it is possible to use other ligands in combination with the above-described ligands. Examples of other ligands preferably used are; a substituted or non-substituted phenylpyridine, phenylpyrazole, phenylimidazole, phenyltriazole, phenyltetrazole, pyrazabole, picolinic acid and carbene.

In Formula (1), M is a transition metal element (also simply called as a transition metal) belonging to groups 8 to 10 in the periodic table. Particularly, iridium and platinum are preferable transition metal elements.

Among compounds represented by Formula (1) relating to the present invention, a preferable embodiment is a compound represented by Formula (2).

<<Compound (metal complex) represented by Formula (2)>>

A compound represented by Formula (2) will be described.

In Formula (2), an alkyl group represented by R is synonymous with an alkyl group each represented by Ra, Rb and Rc in the above-described Q-1, Q-2 and Q-3.

In Formula (2), a cycloalkyl group represented by R is synonymous with a cycloalkyl group each represented by Ra, Rb and Re in the above-described Q-1, Q-2 and Q-3.

In Formula (2), an aromatic hydrocarbon ring group represented by R is synonymous with an aromatic hydrocarbon ring group each represented by Ra, Rb and Rc in the above-described Q-1, Q-2 and Q-3.

In Formula (2), an aromatic heterocyclic group represented by R is synonymous with an aromatic heterocyclic group each represented by Ra, Rb and Rc in the above-described Q-1, Q-2 and Q-3.

Among the compounds represented by Formula (2), preferable group represented by R are an aromatic hydrocarbon ring group and an aromatic heterocyclic group. More preferable are groups represented, by Formulas (A), (B) and (C).

(Groups each, represented by Formulas (A), (B) and (C))

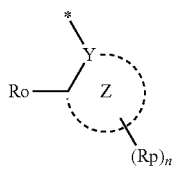

Formula (A)

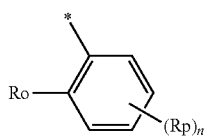

Formula (B)

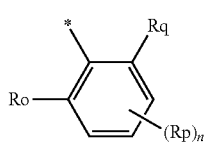

Formula (C)

Hereafter, groups represented by Formulas (A), (B) and (C) will be described.

(Group represented by Formula (A))

In Formula (A), Z represents a group of atoms necessary to form a 6-membered aromatic hydrocarbon ring, 6-membered aromatic heterocycle, 5-membered aromatic heterocycle, or a 5-membered heterocycle, "*" indicates a linking position. n represents an integer of 0 to 4.

In Formula (A), an example of a 6-membered aromatic hydrocarbon ring group represented by Z is a benzene ring, which may be have a substituent as described above.

In Formula (A), examples of a 6-membered aromatic heterocycle represented by Z include: a pyridine ring, a pyridazine ring, a pyrimidine ring, a pyrazine ring, and a triazine ring.

In Formula (A), examples of a 5-membered heterocyle represented by Z include: dihydrothiophene, tetrahydrothiophene, pyrrolidone, dihydropyrrole, tetrahydrofuran, dihydrofuran, dihydrophosphor, phosphorane, silorane, dihydrosilole, dihydroimidazole, dihydropyrazole, dihydrooxazole, dihydrothiazole, dehydroisoxazole, and dihydroisothiazole.

In Formula (A), examples of a 5-membered aromatic heterocyele represented by Z include; thiophene, pyrrole, furan phosphor, silole, imidazole, pyrazole, triazole, tetrazole, thiazole, oxazole, isothiazole, and isoxazole.

In Formula (A), Rp represents a substituent. This substituent is synonymous with a substituent which may be substituted on a 6-membered aromatic hydrocarbon ring, and a 5- or 6-membered aromatic heterocycle represented by A and B in Formula (1).

In Formula (A), Ro represents a substituent having a steric parameter value (Es value) of −0.5 or less. This substituent is preferably bonded to an atom adjacent to the bonding position (*) of a 6-membered aromatic hydrocarbon, 6-membered aromatic heterocycle, 5-membered aromatic heterocycle, or a 5-membered heterocycle which is formed with the aforesaid Z. Further, it is preferable to be an electro donating group.

(Steric parameter value: "Es value")

"Es value", as described herein, refers to a steric parameter derived from chemical reactivity. It is possible to describe that a decrease in this value indicates that the substituent becomes spatially more bulky.

It is common knowledge that in a hydrolysis reaction of esters under acidic conditions, effects for the progress of the reaction may he considered to be only caused by the steric hindrance. Based on this, the value which numerically expresses the steric hindrance is Es value.

Es value of substituent X may he obtainable as follows. Reaction rate constant kX of the following chemical reaction in which α-position mono-substituted acetate, which is derived from α-position mono-substituted acetic acid prepared by substituting, one hydrogen atom of the methyl group of acetic acid with substituent X, undergoes hydrolysis under acidic conditions, is obtained.

$$X\text{-}CH_2COORX + H_2O \rightarrow X\text{-}CH_2COOH + RXOH$$

Reaction rate constant kH of the following reaction (RX is the same as RY) in which acetate corresponding to the above α-position mono-substituted acetate undergoes hydrolysis under acetic conditions, is also obtained.

$$CH_3COORY + H_2 \rightarrow CH_3COOH + RYOH$$

Subsequently, Es is obtained via the following formula.

$$Es = \log(kX/kH)$$

The reaction rate decreases due to steric hindrance of substituent X. As a result, since kX<kH is held, Es value commonly becomes negative.

In practice, when Es value is obtained, two reaction rate constants, namely kX and kH, are determined and it is calculated based on the above formula.

Specific examples of Es value are detailed in Unger, S. H., Hansen, C., Prog. Phys. Org. Chem. 12,91 (1976).

Further, specific numerical values are also described in "Yakubutsu no Kozo Kassei Sokan (Structural Activity Congelation)" (Kagakuno Ryoiki Zokan No. 122, Nanko Do), and "American Chemical Society Professional Reference Book, 'Exploring QSAR' p. 81, Table 3-3". Table 1 below shows some of them.

TABLE 1

| Substituent | Es Value |
|---|---|
| H | 0 |
| F | −0.46 |
| Cl | −0.97 |
| Br | −1.16 |
| I | −1.4 |
| $CH_3$ | −1.24 |
| $C_2H_5$ | −1.31 |
| $n\text{-}C_3H_7$ | −1.6 |
| $n\text{-}C_4H_9$ | −1.63 |
| $i\text{-}C_4H_9$ | −2.17 |
| $s\text{-}C_4H_9$ | −2.37 |
| $t\text{-}C_4H_9$ | −2.78 |
| $cyclo\text{-}C_4H_7$ | −1.3 |
| $n\text{-}C_5H_{11}$ | −1.64 |
| $i\text{-}C_5H_{11}$ | −1.59 |
| $CH(C_2H_5)$ | −3.22 |
| $cyclo\text{-}C_6H_{11}$ | −2.03 |
| $CH_2F$ | −1.48 |
| $CH_2Cl$ | −1.48 |
| $CH_2Br$ | −1.51 |
| $CH_2I$ | −1.61 |
| $CH_2OH$ | −1.21 |

TABLE 1-continued

| Substituent | Es Value |
| --- | --- |
| $CH_2OCH_3$ | −1.43 |
| $CH_2NO_2$ | −2.71 |
| $CH_2COCH_3$ | −1.99 |
| $CHF_2$ | −1.91 |
| $CHCl_2$ | −2.78 |
| $CHBr_2$ | −3.1 |
| $CHOHCH_3$ | −1.15 |
| $CF_3$ | −2.4 |
| $CCl_3$ | −3.3 |
| $CBr_3$ | −3.67 |
| $C(C_6H_5)_3$ | −5.92 |
| $CHCH_3$ | −2.84 |
| CN | −0.51 |
| OH | −0.55 |
| $OCH_3$ | −0.55 |
| SH | −1.07 |
| $SCH_3$ | −1.07 |
| $SF_5$ | −2.91 |
| $NH_2$ | −0.61 |

Further, it should be noted that the Es value, which is defined in the present invention, is not determined while a methyl group is 0, but is determined while a hydrogen atom, to be 0, whereby the Es value of the present invention is a value which is obtained by subtracting 1.24 from the Es value determined while a methyl group is 0.

In one of the embodiments of n the present invention, the Es value is commonly −0.5 or less, it is preferably between −7.0 and −0.6, but it is most preferably between −7.0 and −1.0.

Here, in the present invention, in the case of a substituent at a steric parameter (being a Es value) of −0.5 or less, for example, in the case in which keto-enol tautomers are present in R and R', the Es value of the keto portion is determined via conversion as an enol isomer. In cases in which other tautomers are present, Es values are determined based on the same conversion method. Further, a substituent having an Es value of −0.5 or less is preferably an electron donative group in terms of electronic effects.

(Electron donating group: Substituent having an electron donating property)

In the present invention, "a substituent having an electron donating property" means a substituent which exhibits Hammett σp value described below is a negative value, and such substituent has a larger tendency to donate electrons to the bonded atoms when compared with a hydrogen atom.

Specific examples of an electron-donating substituent include: a hydroxyl group, a thio group, an alkoxyl group (for example, a methoxy group), an alkylthio group, an arylthio group, an acetyloxy group, an amino group, a dimethylamino group, an acetylamino group, alkyl groups (for example, a methyl group, an ethyl group, a propyl group and tert-butyl group), and aryl groups (for example, a phenyl group and a mesityl group). The following literatures can be referred to for Hammett σp value, for example.

Hammett σp value of trie present invention represents Hammett substituent constant σp. Hammett σp value was determined from the electronic effect of the substituent exerted on hydrolysis of ethyl benzoate by Hammett et al. Groups shown in, for example, "Structure-activity relationship of a drug" (Nankodo Co., Ltd.: 1979), or "Substituent Constants for Correlation Analysis in chemistry and biology" (C. Hansch and A. Leo, John Wiley & Sons, New York, 1979) can be cited.

In the present invention, among the groups represented by the aforesaid Formula (A), groups represented by Formula (B) and Formula (C) are preferable.

<<Group Represented by Formula (B)>>

In Formula (B), a substituent represented by Ro and having a steric parameter value (Es value) of −0.5 or less is synonymous with a substituent represented by Ro and having a steric parameter value (Es value) of −0.5 or less in Formula (A).

In Formula (B), a substituent represented by Rp is synonymous with a substituent described for a compound represented by Formula (1). n represents an integer of 0 to 4.

<<Group Represented by Formula (C)>>

In Formula (C), a substituent represented by Ro and Rq and having a steric parameter value (Es value) of −0.5 or less is synonymous with a substituent represented by Ro and having a steric parameter value (Es value) of −0.5 or less in Formula (4).

In Formula (C), a substituent represented by Rp is synonymous with a substituent described for a compound represented by Formula (1). n represents an integer of 0 to 4.

In Formula (2). a substituent each represented by $R_{11}$ to $R_{16}$ is synonymous with a substituent which may be substituted on a 6-membered aromatic hydrocarbon ring, and a 5- or 6-membered aromatic heterocycle represented by A and B in Formula (1).

In Formula (2), at least one of $R_{11}$ to $R_{16}$ represents Q. This Q is synonymous with a substituent Q in Formula (1) having a vacant orbital which is capable of accepting a π electron from A or B.

In Formula (2), a transition metal element belonging to groups 8 to 10 in the periodic table and represented by M is synonymous with a transition metal element belonging to groups 8 to 10 in the periodic table and represented by M in Formula (1).

In Formula (2), any ligand represented by L is synonymous with any ligand represented by L in Formula (1) which is capable of coordinating with M.

<<Compound (metal complex) Represented by Formula (3)>>

In a compound represented by Formula (3), a substituent each represented by $R_{21}$ to $R_{26}$ is synonymous with a substituent which may be substituted on a 6-membered aromatic hydrocarbon ring, and a 5- or 6-membered aromatic heterocycle represented by A and B in Formula (1).

In a compound represented by Formula (3), at least one of $R_{21}$ to $R_{20}$ represents Q. This Q is synonymous with a substituent Q in Formula (1) having a vacant orbital which is capable of accepting a π electron from A or B.

In a compound represented by Formula (3), a transition metal element belonging to groups 8 to 10 in the periodic table and represented by M is synonymous with a transition metal element belonging to groups 8 to 10 in the periodic table and represented by M in Formula (1).

In a compound represented by Formula (3), any ligand represented by L is synonymous with any ligand represented by L in Formula (1) which is capable of coordinating with M.

<<Compound (metal complex) Represented by Formula (4)>>

In a compound represented by Formula (4), a substituent each represented by $R_{31}$ to $R_{37}$ is synonymous with a substituent which may be substituted on a 6-membered aromatic hydrocarbon ring, and a 5- or 6-membered aromatic heterocycle represented by A and B in Formula (1).

In a compound represented by Formula (4), at least one of $R_{31}$ to $R_{37}$ represents Q. This Q is synonymous with a substituent Q in Formula (1) having a vacant orbital which is capable of accepting a π electron from A or B.

In a compound represented by Formula (4), a transition metal element belonging to groups 8 to 10 in the periodic table and represented by M is synonymous with a transition metal element belonging to groups 8 to 10 in the periodic table and represented by M in Formula (1).

In a compound represented by Formula (4), any ligand represented by L is synonymous with any ligand represented by L in Formula (1) which is capable of coordinating with M.

<<Compound (metal complex) Represented by Formula (5)>>

In a compound represented by Formula (5), a substituent each represented by $R_{51}$ to $R_{57}$ is synonymous with a substituent which may be substituted on a 6-membered aromatic hydrocarbon ring, and a 5- or 6-membered aromatic heterocycle represented by A and B in Formula (1).

In a compound represented by Formula (5), at least one of $R_{51}$ to $R_{57}$ represents Q. This Q is synonymous with a substituent Q in Formula (1) having a vacant orbital which is capable of accepting a π electron from A or B.

In a compound represented by Formula (5), a transition metal element belonging to groups 8 to 10 in the periodic table and represented by M is synonymous with a transition metal element belonging to groups 8 to 10 in the periodic table and represented by M in Formula (1).

In a compound represented by Formula (5), any ligand represented by L is synonymous with any ligand represented by L in Formula (1) which is capable of coordinating with M.

Hereafter, specific examples of a compound (it is called as a metal complex or a metal complex compound) represented any one of Formulas (1), (2), (3), (4) and (5) relating to the present invention will be shown. However, the present invention will not be limited to these.

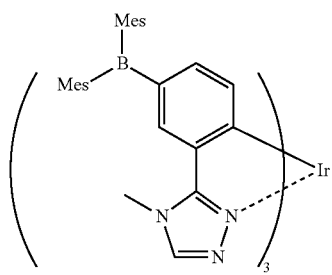

1-1

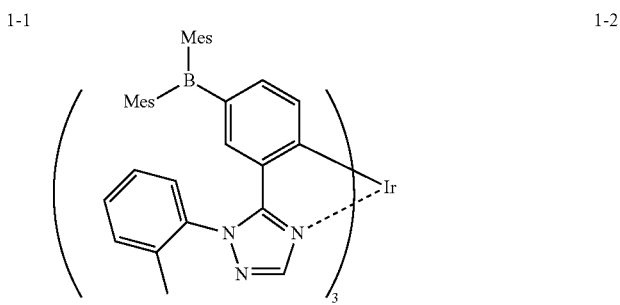

1-2

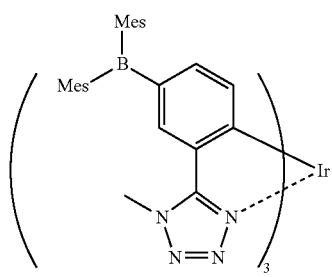

1-3

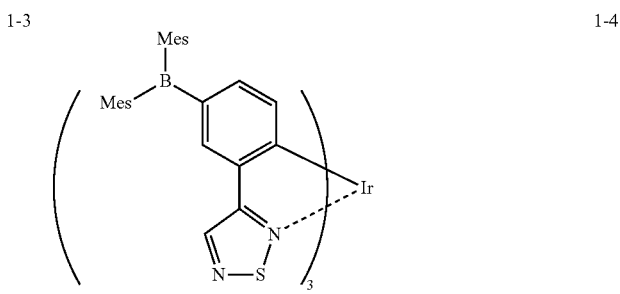

1-4

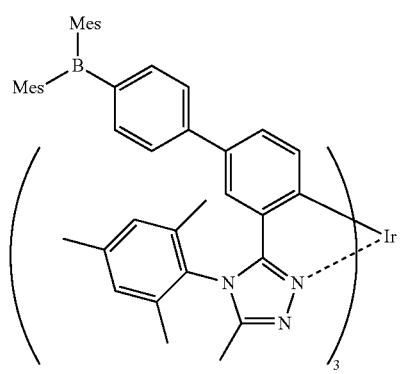

1-5

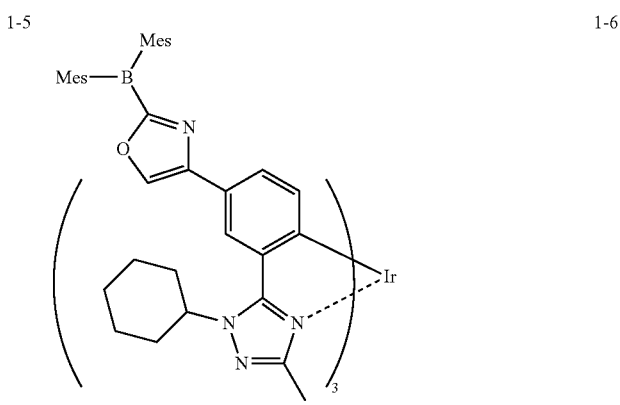

1-6

-continued
1-7
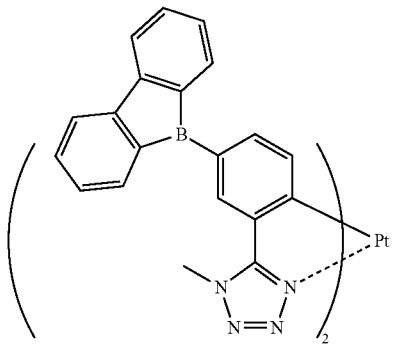
1-8
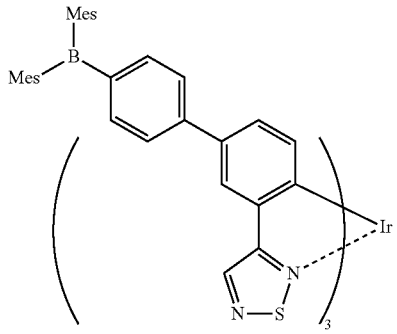
1-9
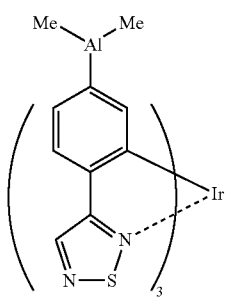
1-10
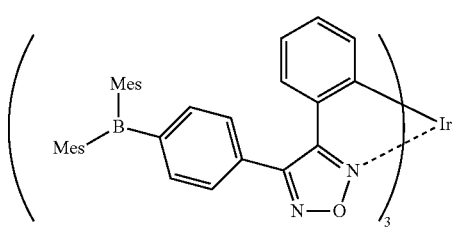
1-11
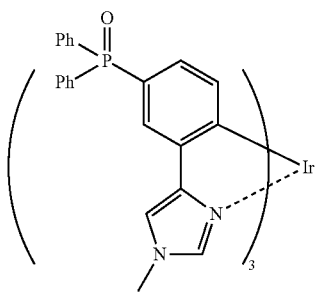
1-12
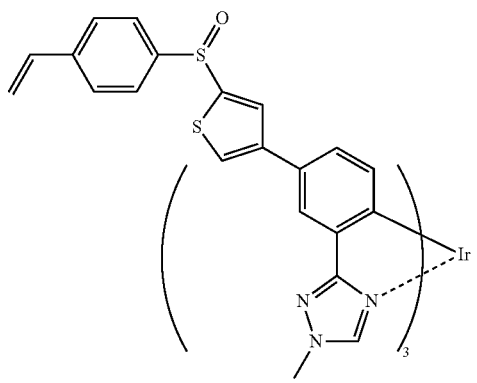
1-13
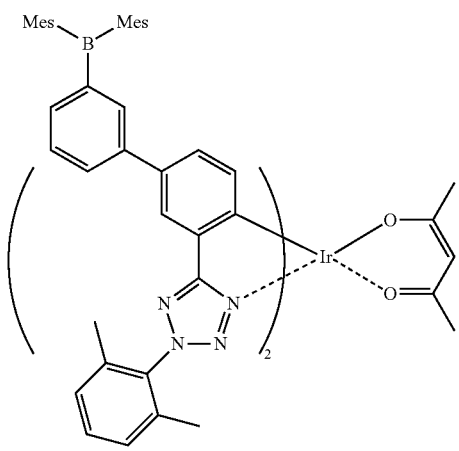
1-14
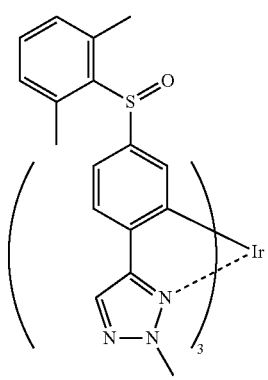

-continued
1-15
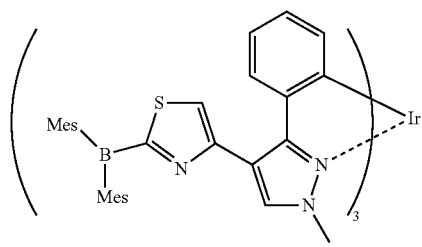
1-16
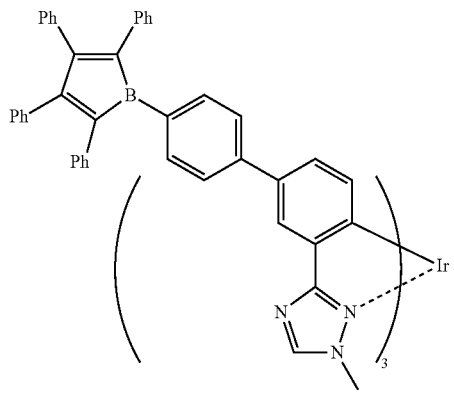
1-17
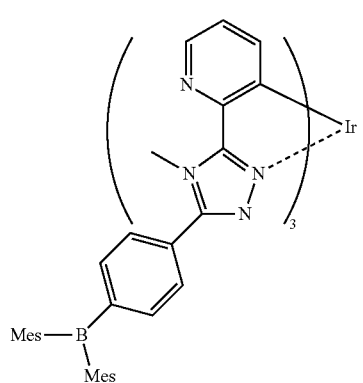
1-18
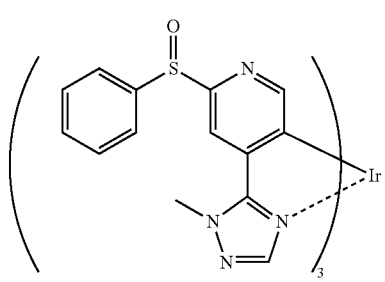
1-19
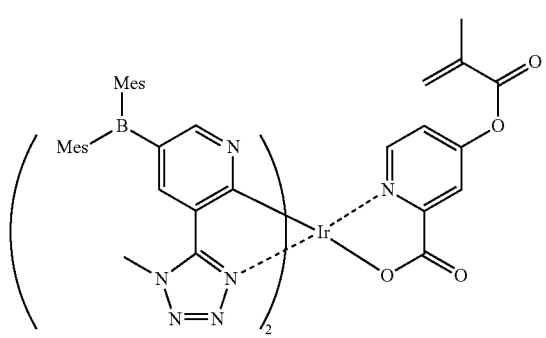
1-20
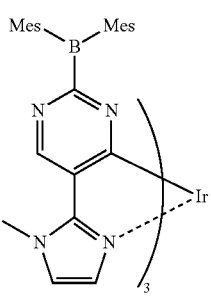
1-21
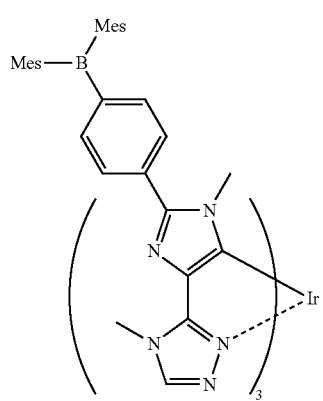
1-22
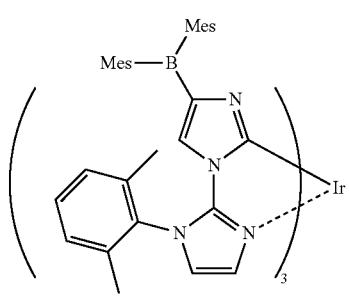

-continued
| | |
|---|---|
| 1-23 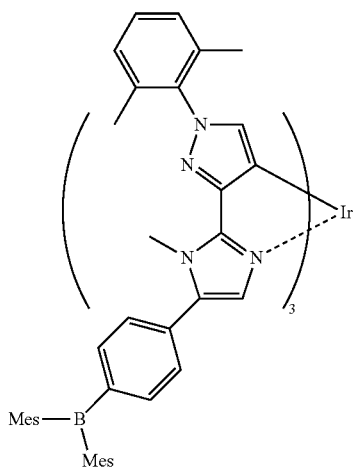 | 1-24 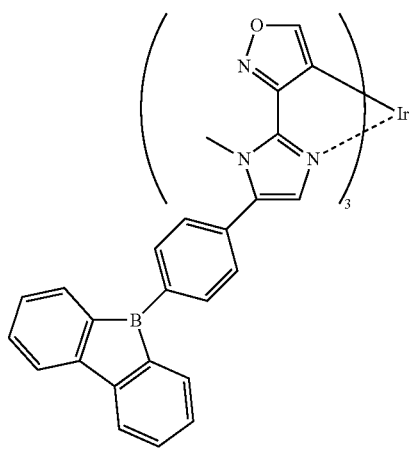 |
| 1-25 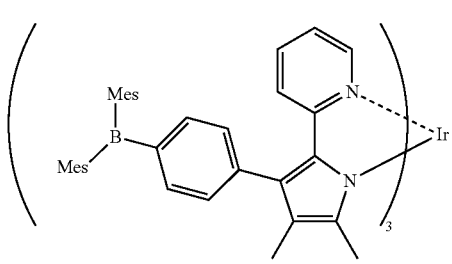 | 1-26 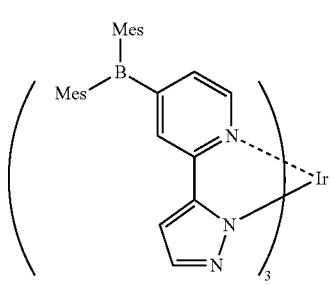 |
| 1-27 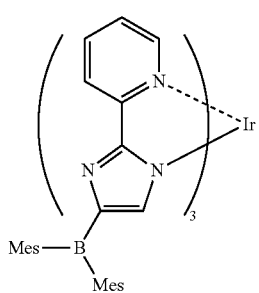 | 1-28 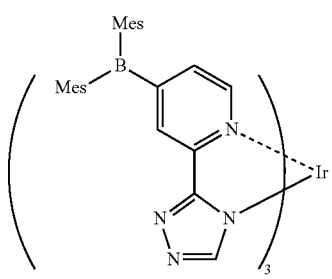 |
| 1-29 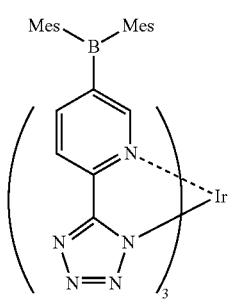 | 1-30 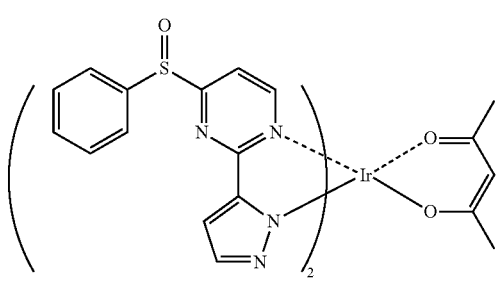 |

-continued
1-31
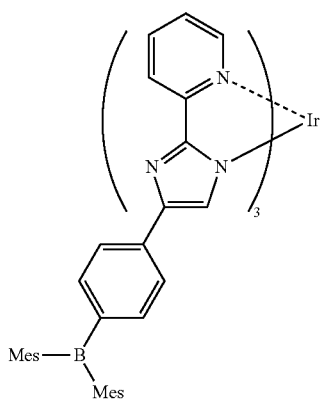
1-32
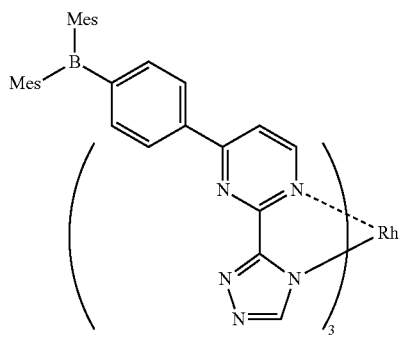
1-33
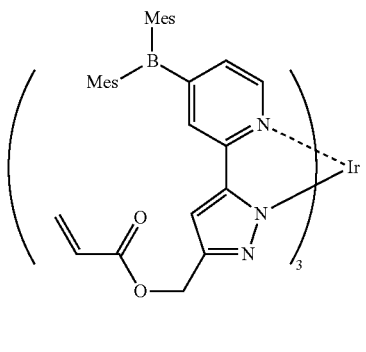
1-34
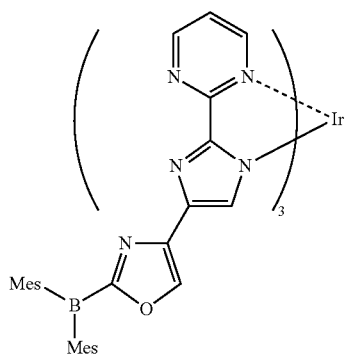
1-35
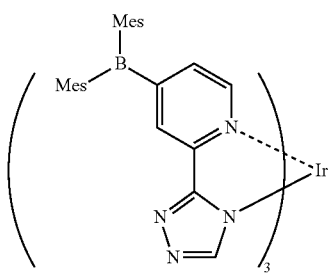
1-36
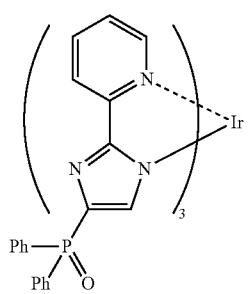
1-37
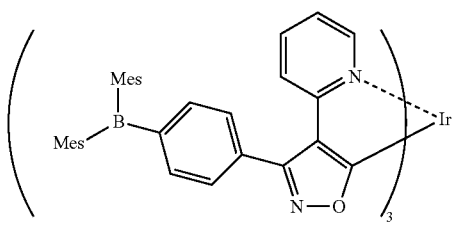
1-38
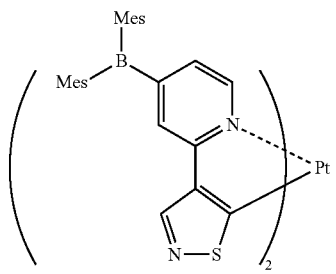

-continued
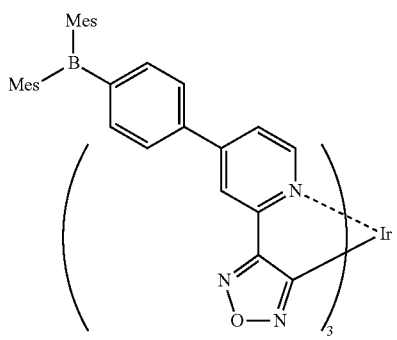 1-39
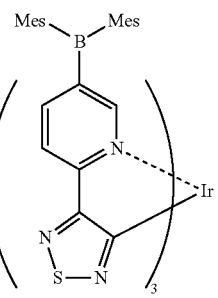 1-40
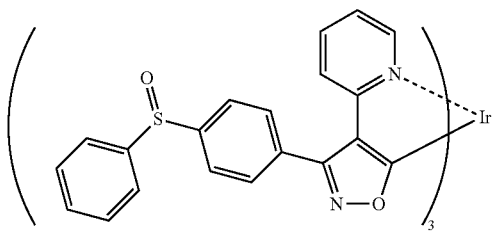 1-41
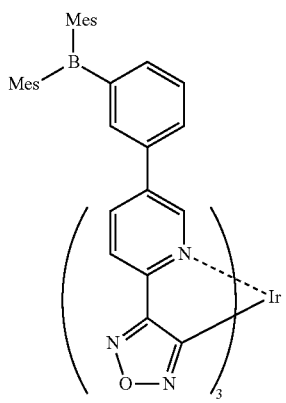 1-42
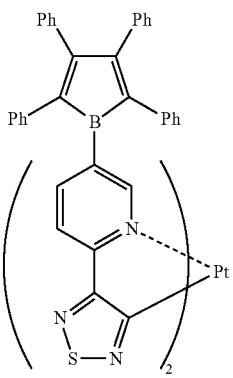 1-43
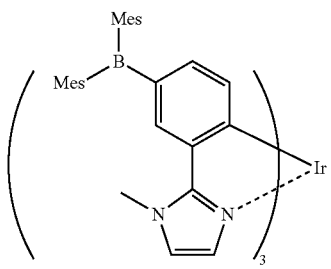 1-44
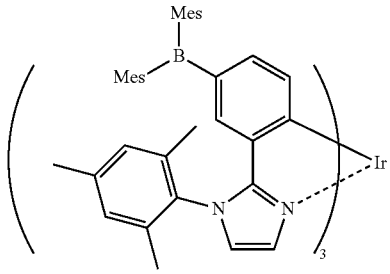 2-1
2-2
2-3
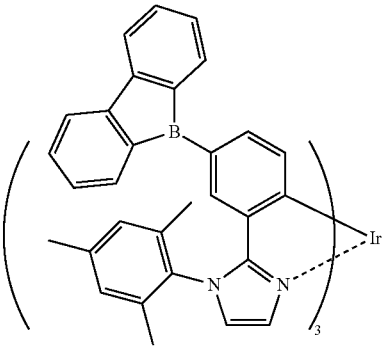 2-4

-continued
2-5
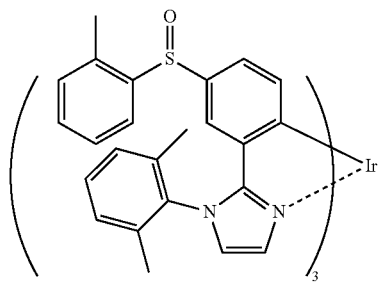
2-6
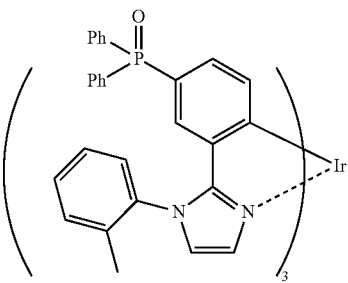
2-7
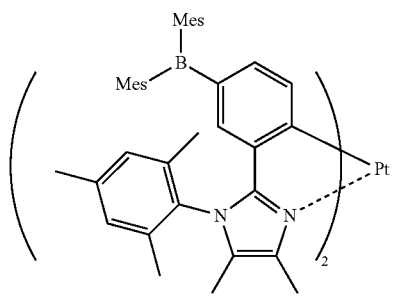
2-8
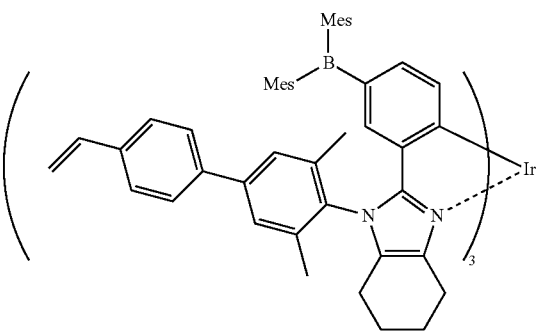
2-9
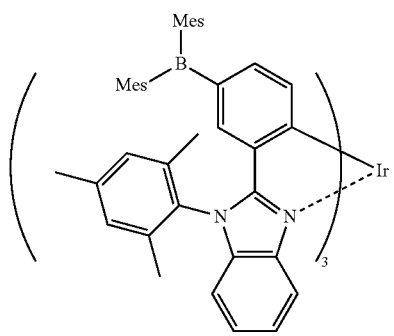
2-10
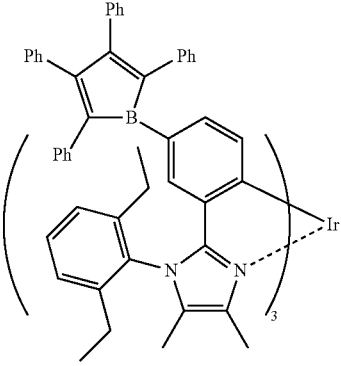
2-11
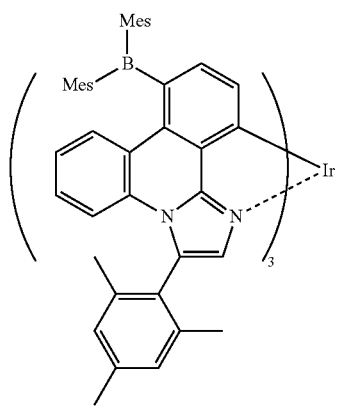
2-12
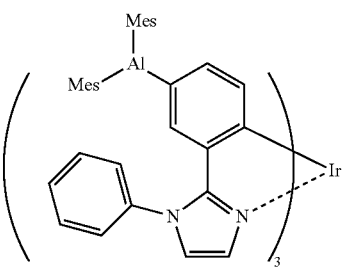

-continued
| | |
|---|---|
| 2-13 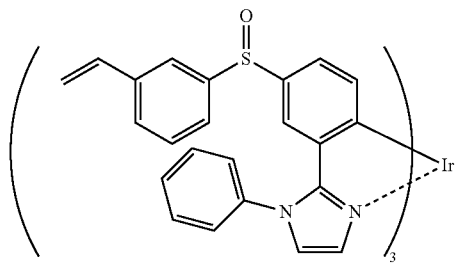 | 2-14 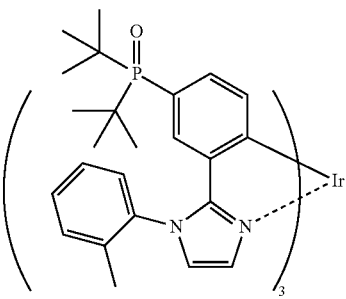 |
| 2-15 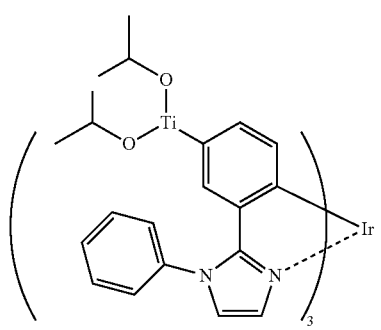 | 2-16 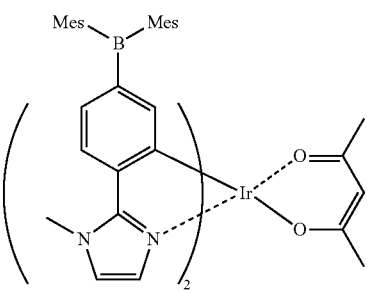 |
| 2-17 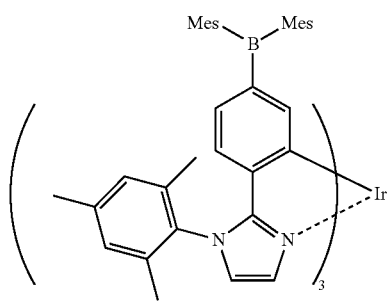 | 2-18 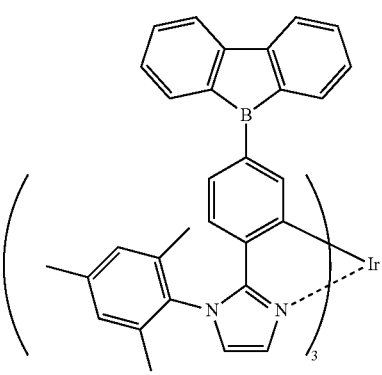 |
| 2-19 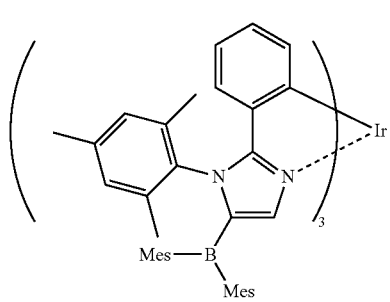 | 2-20 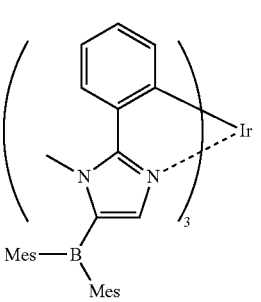 |
| 2-21 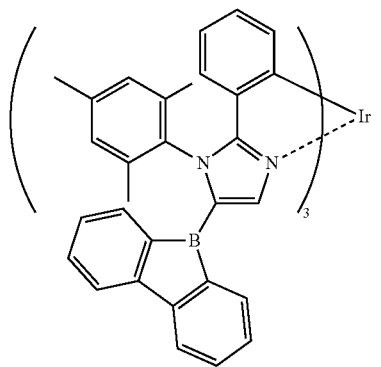 | 2-22 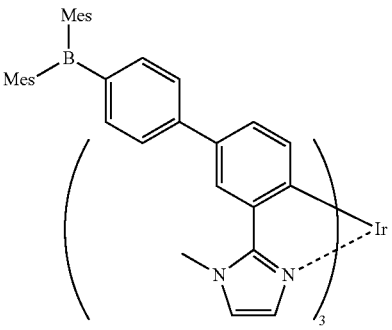 |

-continued
| | |
|---|---|
| 2-23 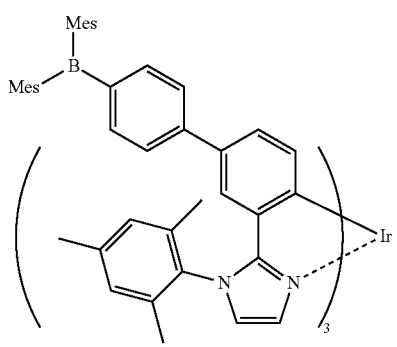 | 2-24 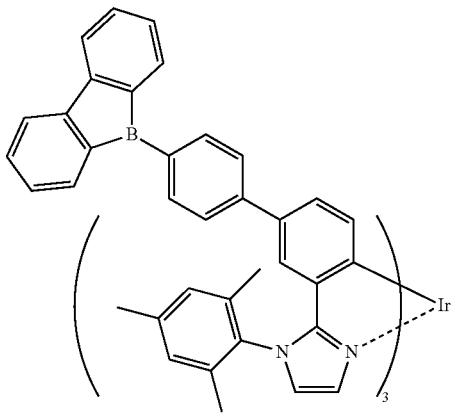 |
| 2-25 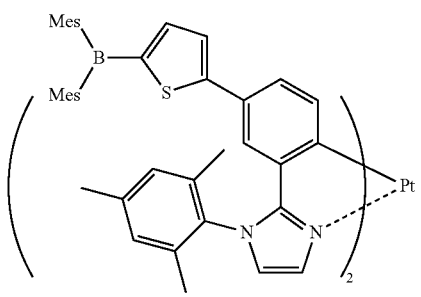 | 2-26 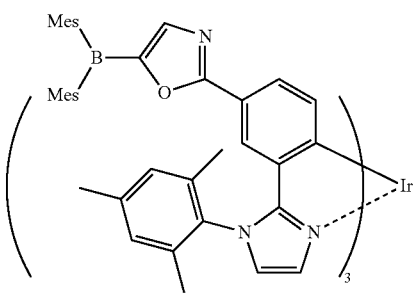 |
| 2-27 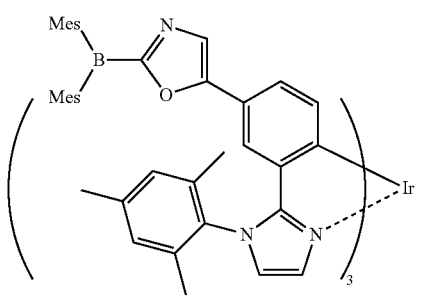 | 2-28 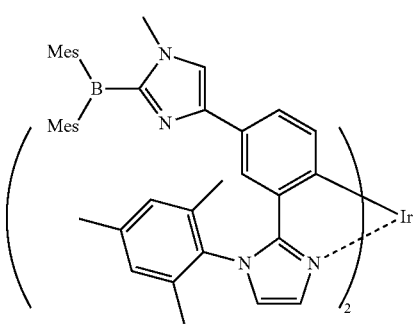 |
| 2-29 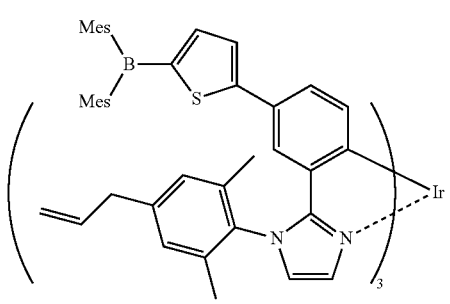 | 2-30 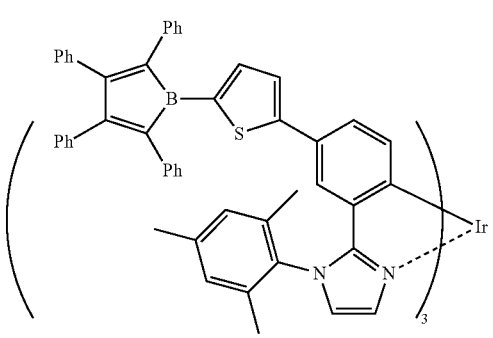 |

-continued
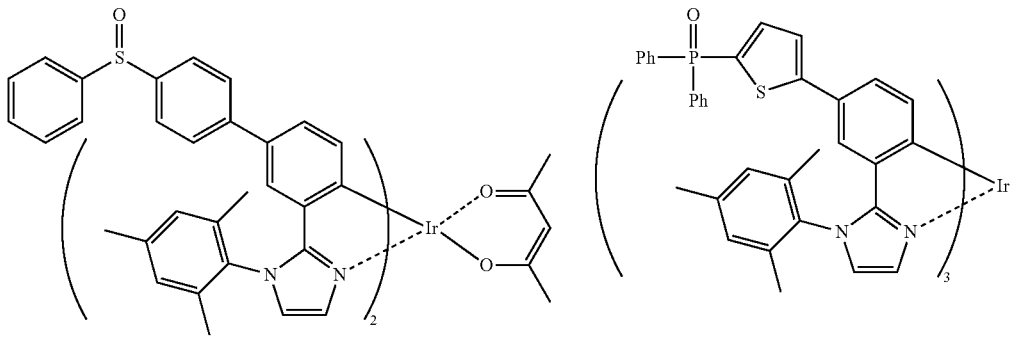
2-31
2-32
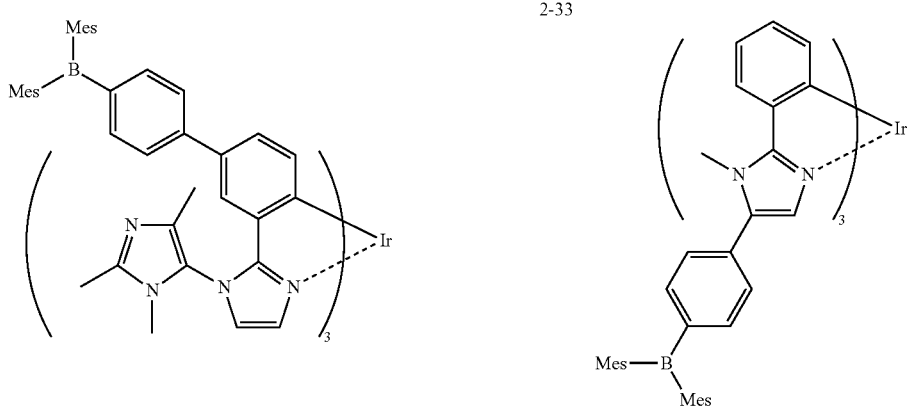
2-33
2-34
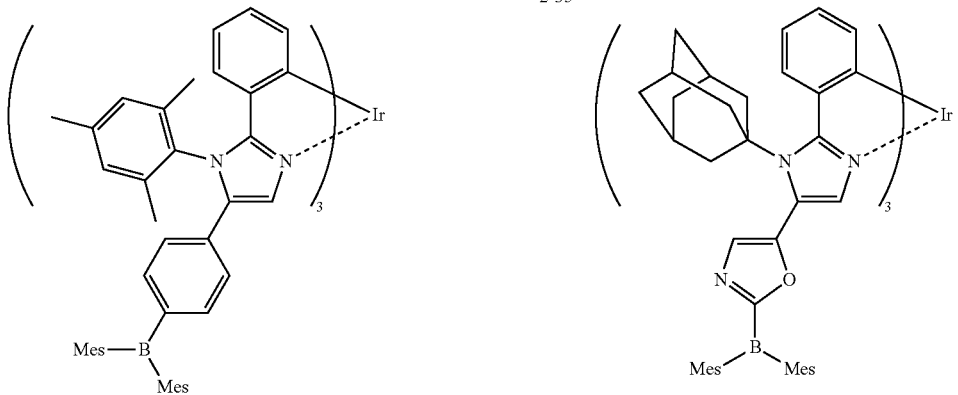
2-35
2-36
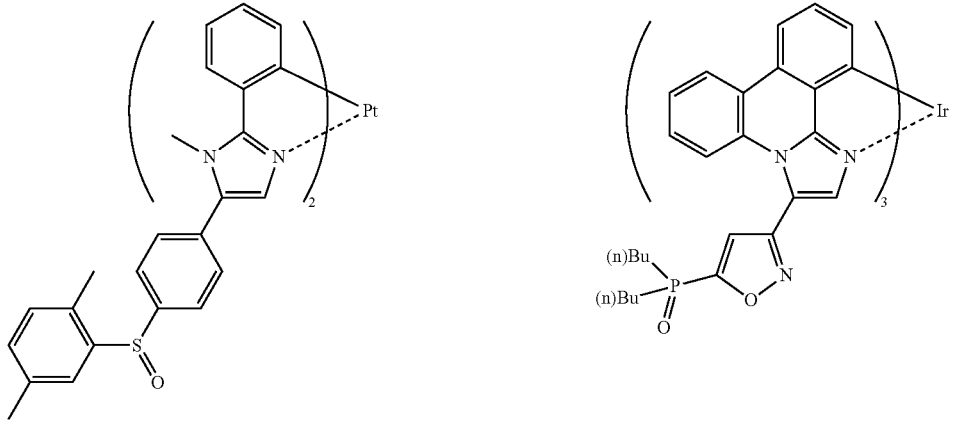
2-37
2-38

-continued
2-39
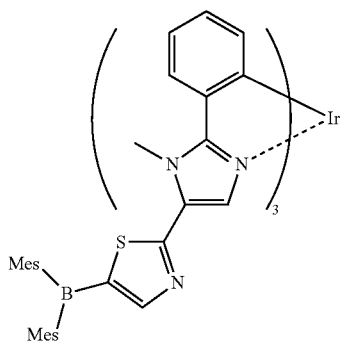
2-40
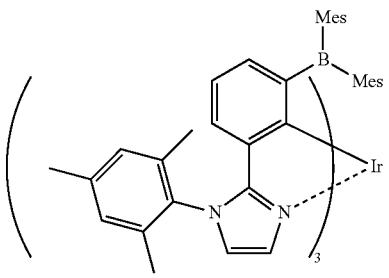
2-41
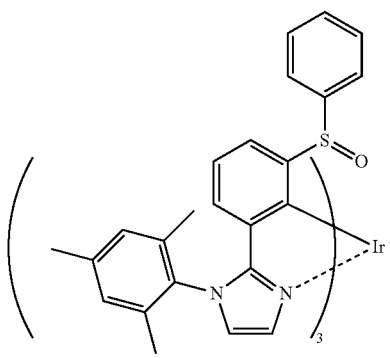
2-42
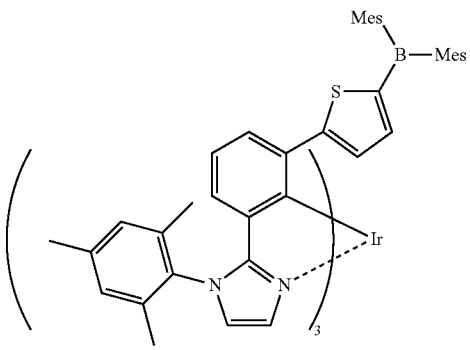
3-1
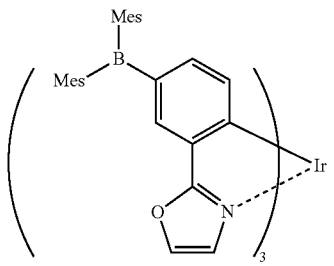
3-2
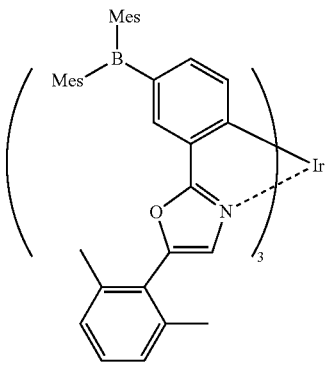
3-3
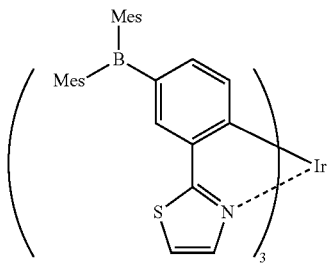
3-4
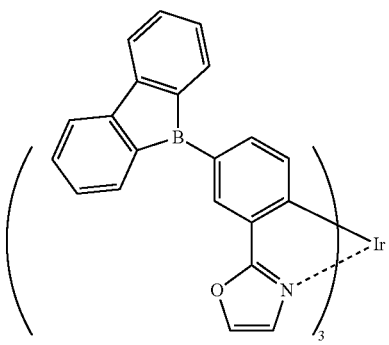

-continued
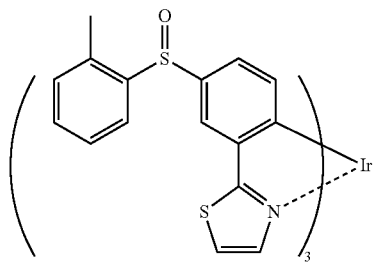
3-5
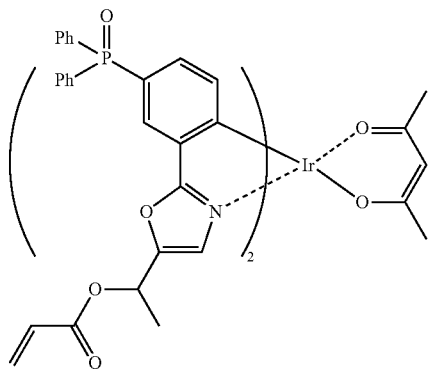
3-6
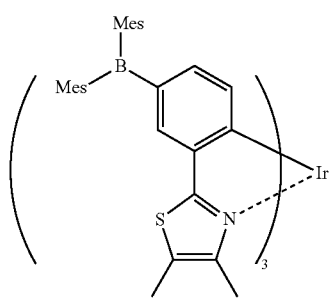
3-7
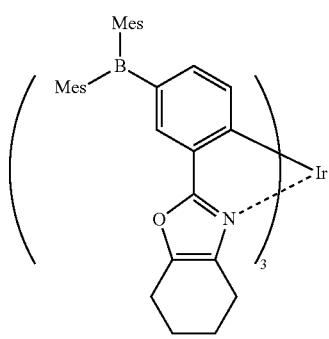
3-8
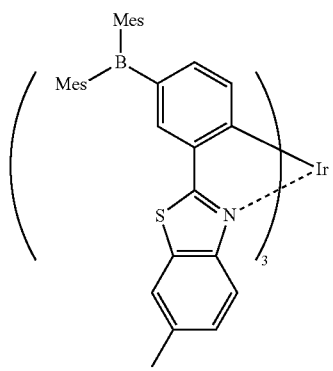
3-9
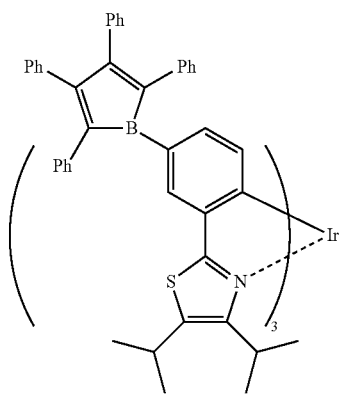
3-10
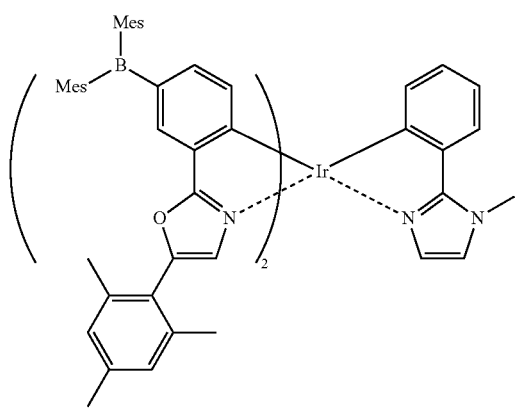
3-11
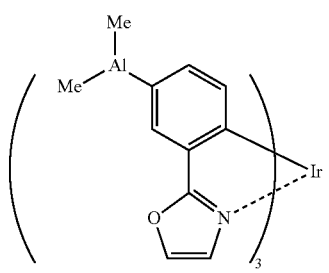
3-12

-continued
3-13
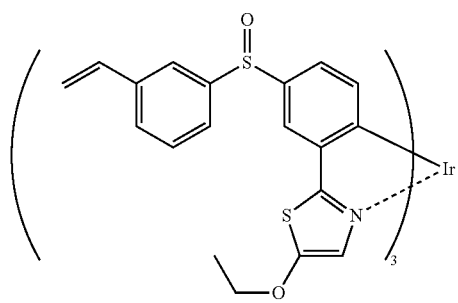
3-14
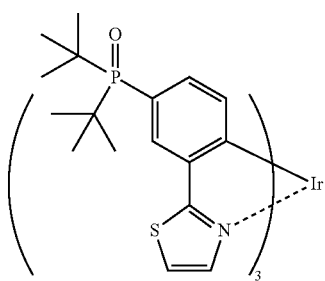
3-15
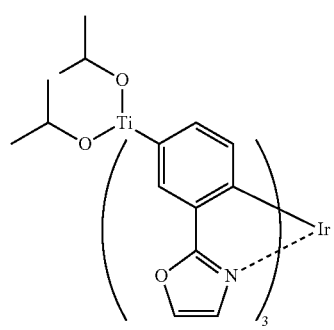
3-16
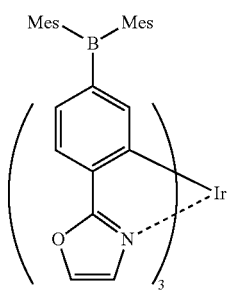
3-17
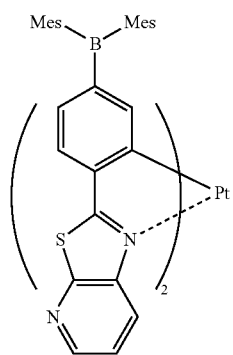
3-18
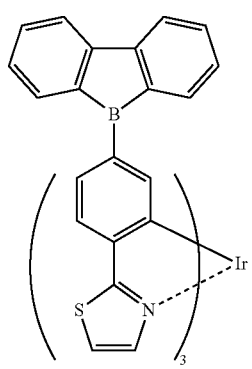
3-19
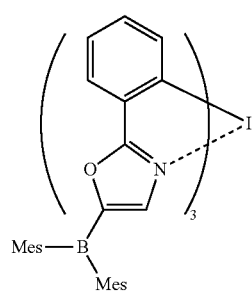
3-20
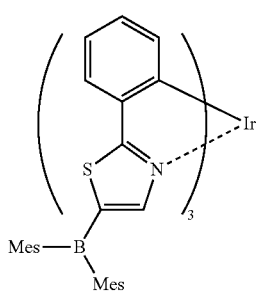
3-21
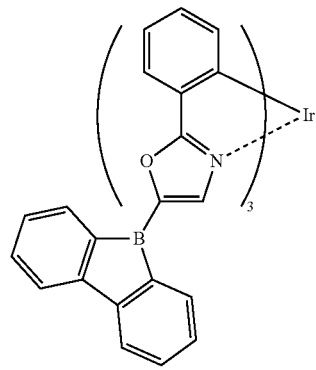
3-22
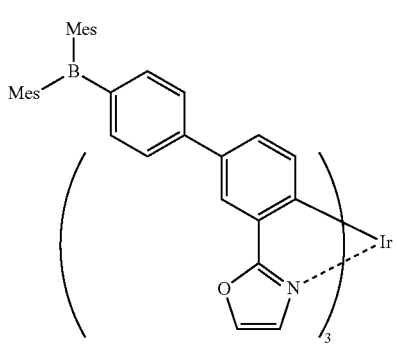

-continued
3-23
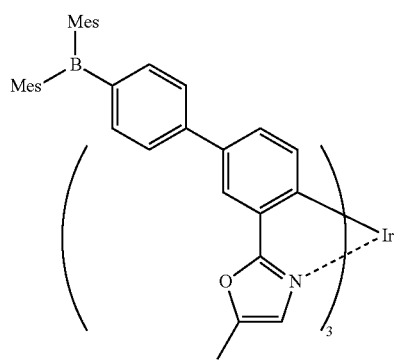
3-24
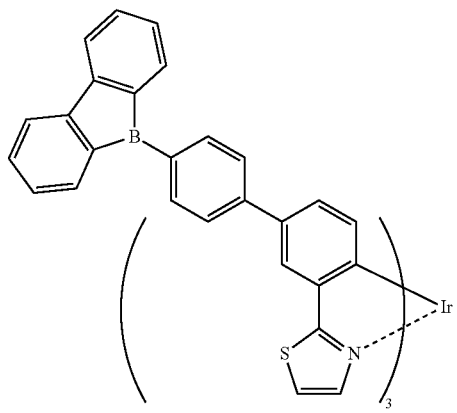
3-25
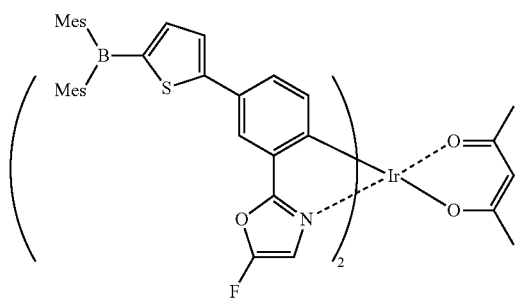
3-26
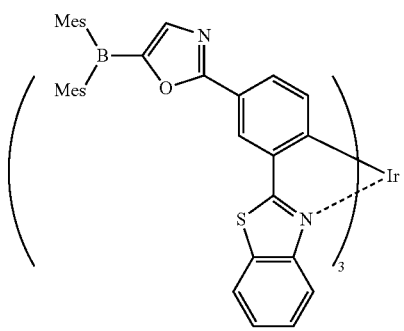
3-27
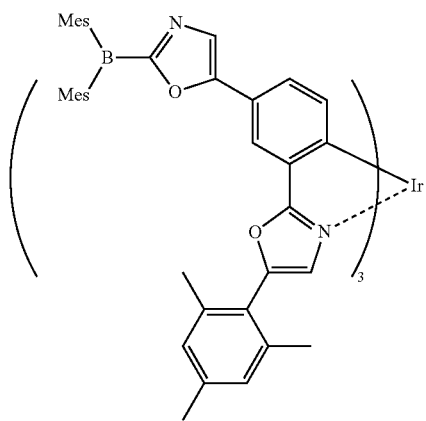
3-28
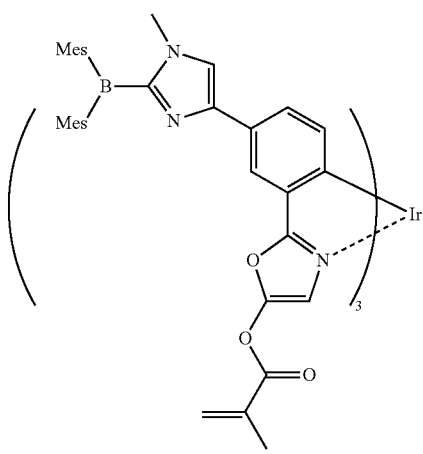
3-29
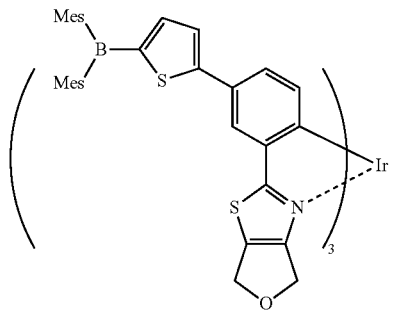
3-30
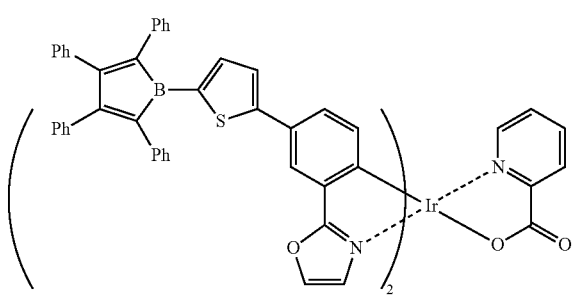

-continued
| | |
|---|---|
| 3-31 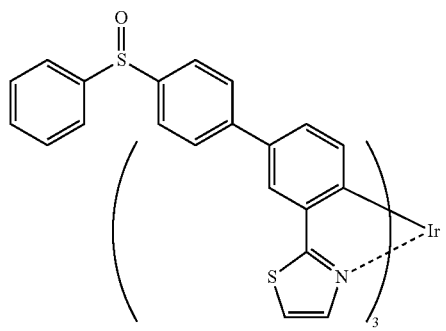 | 3-32 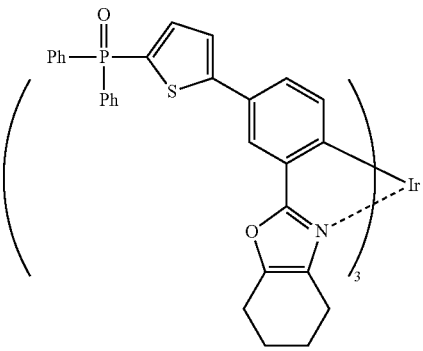 |
| 3-33 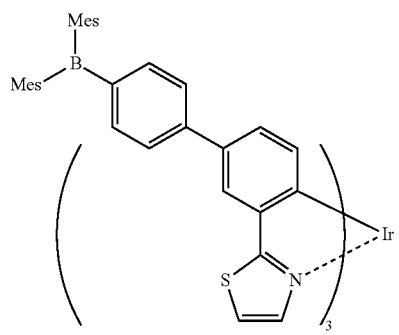 | 3-34 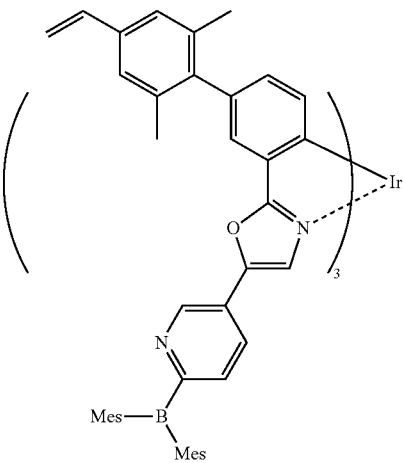 |
| 3-35 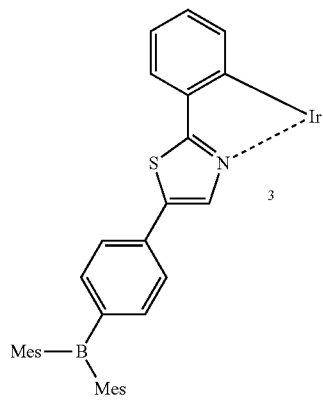 | 3-36 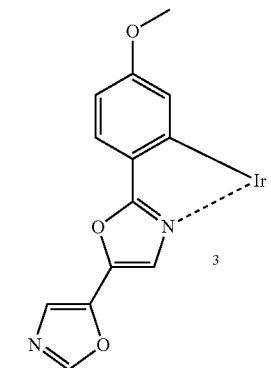 |
| 3-37 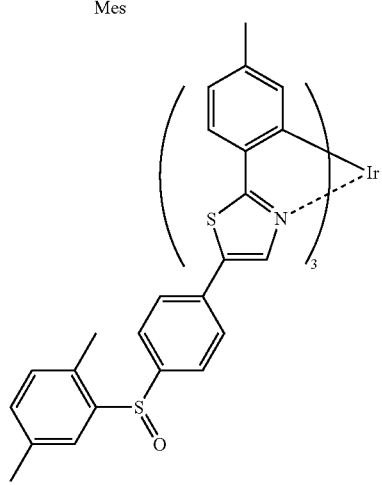 | 3-38 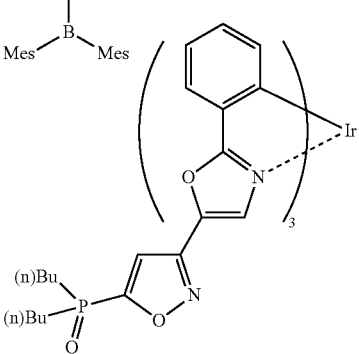 |

-continued
3-39
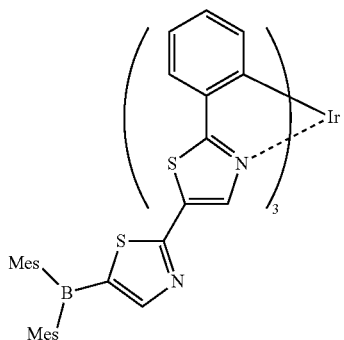
4-1
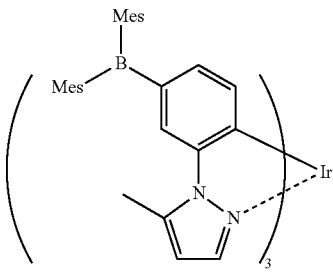
4-2
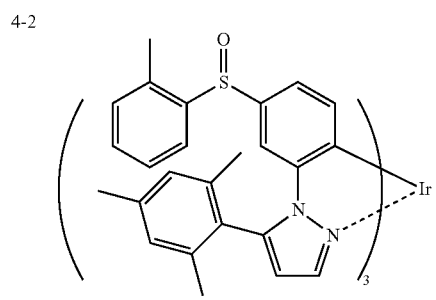
4-3
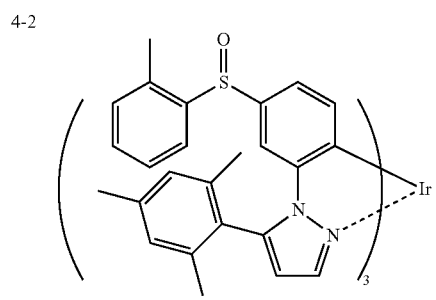
4-4
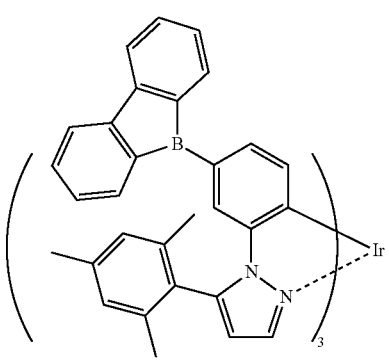
4-5
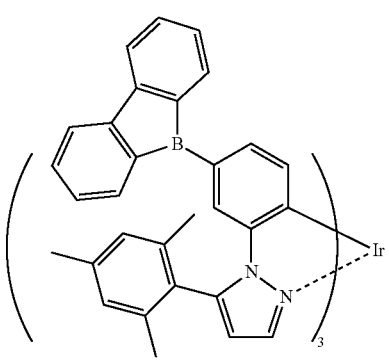
4-6
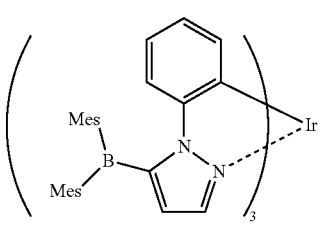
4-7
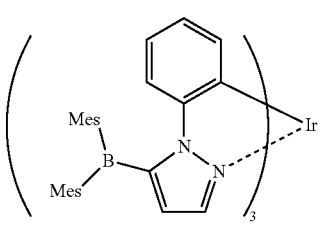
4-8
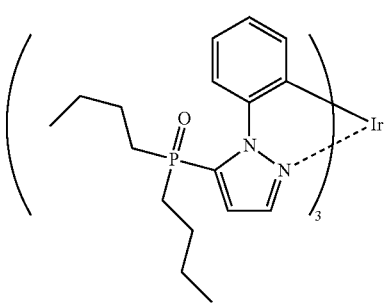
4-9
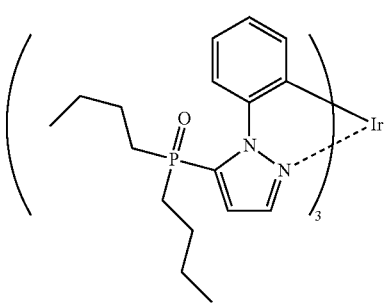

-continued
| 4-10 | 4-11 |
|---|---|
| 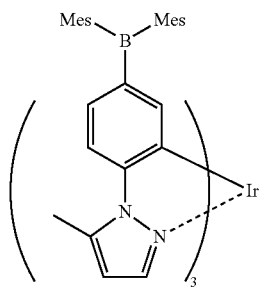 | 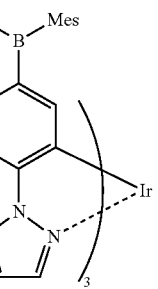 |
| 4-12 | 4-13 |
| 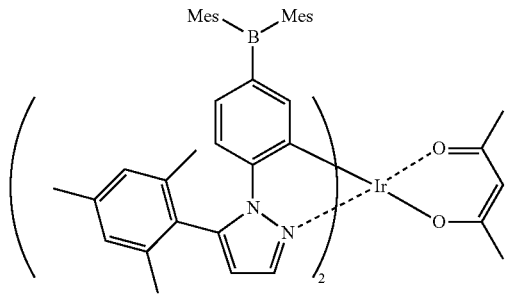 | 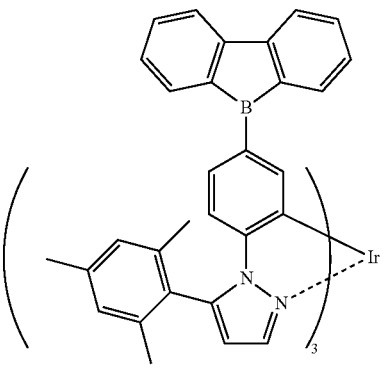 |
| 4-14 | 4-15 |
| 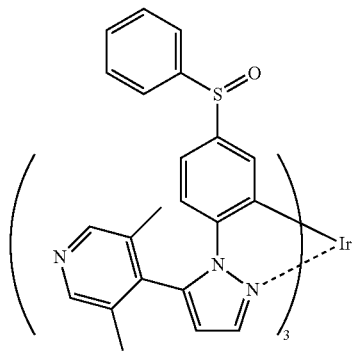 | 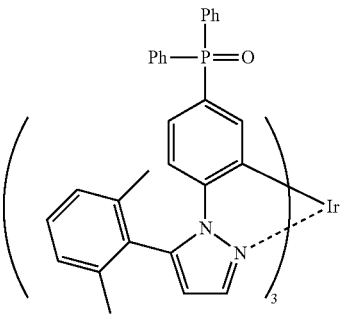 |
| 4-16 | 4-17 |
| 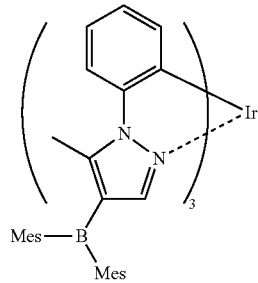 | 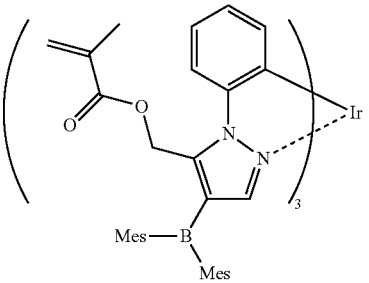 |
| 4-18 | 4-19 |
| 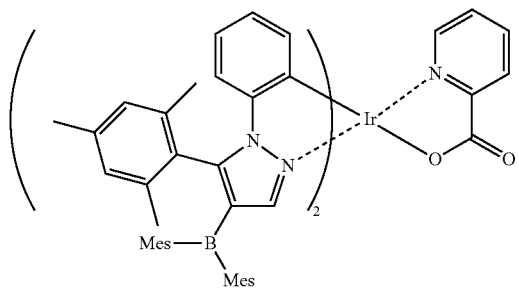 | 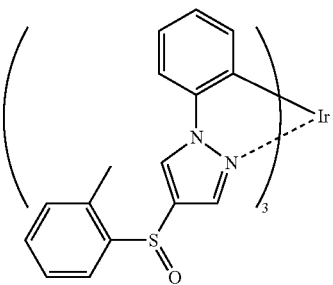 |

4-20
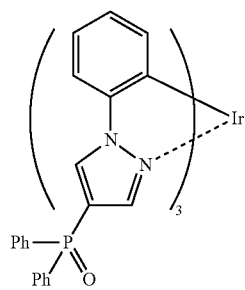
4-21
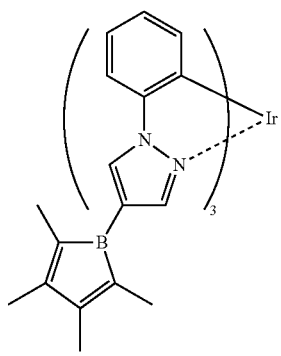
4-22
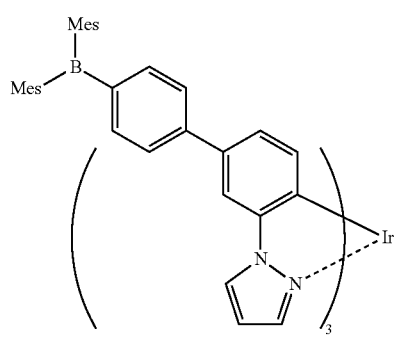
4-23
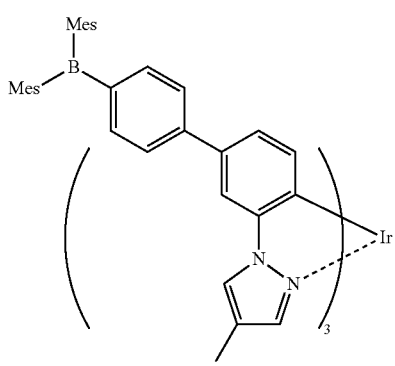
4-24
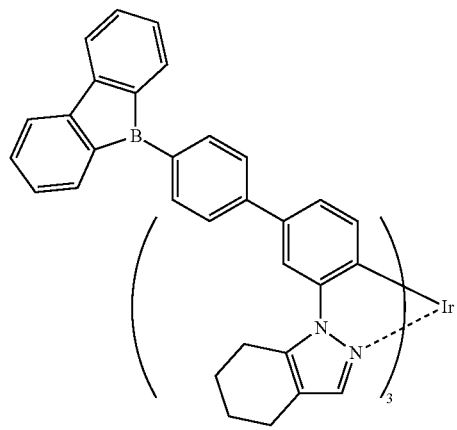
4-25
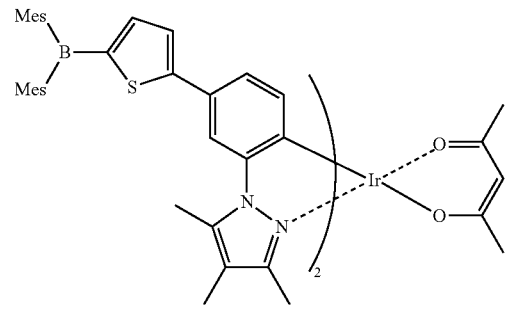
4-26
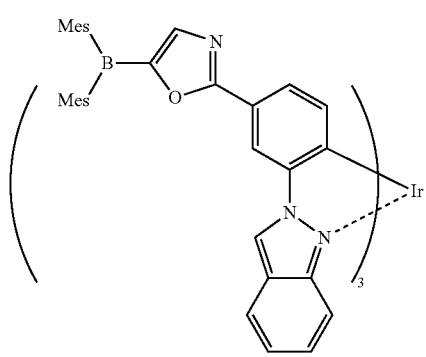
4-27
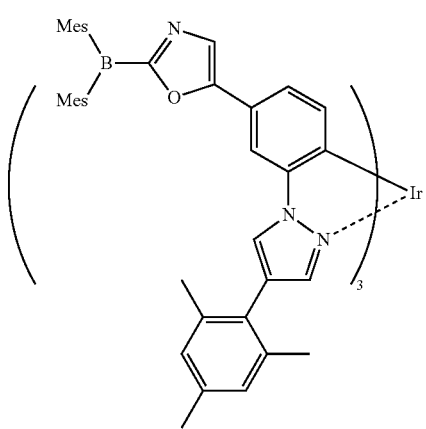

-continued
4-28
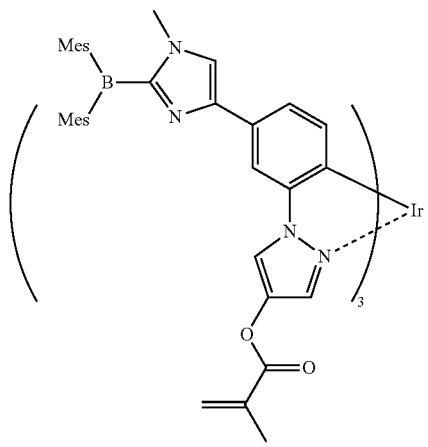
4-29
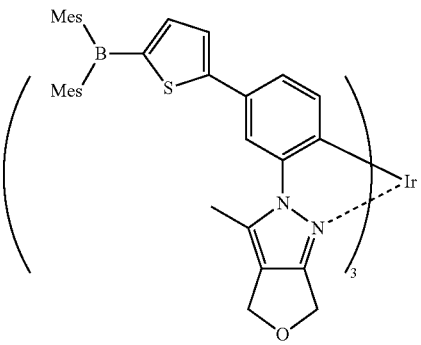
4-30
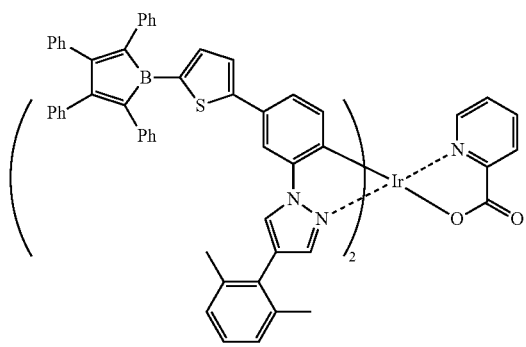
4-31
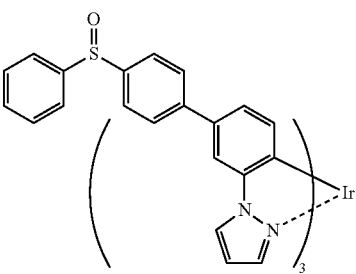
4-32
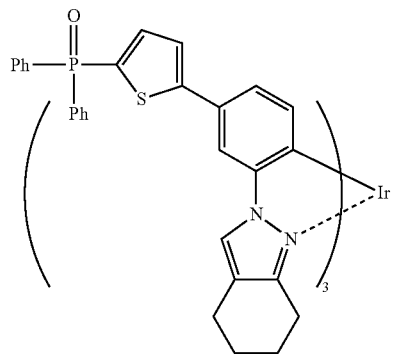
4-33
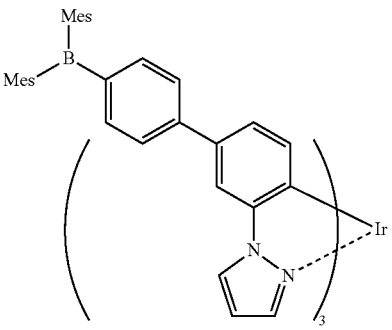
4-34
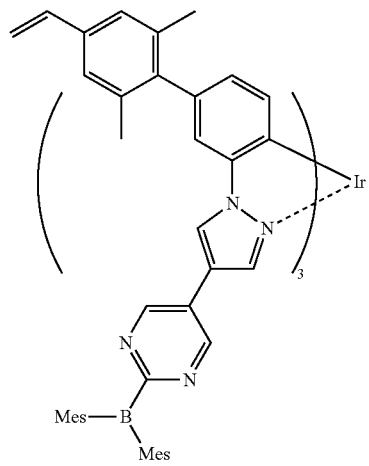
4-35
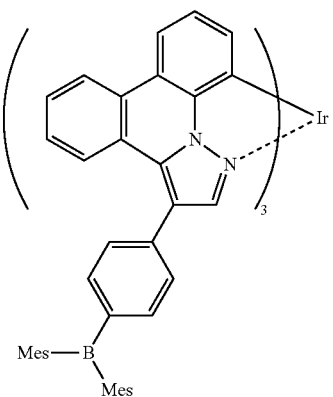

-continued
4-36
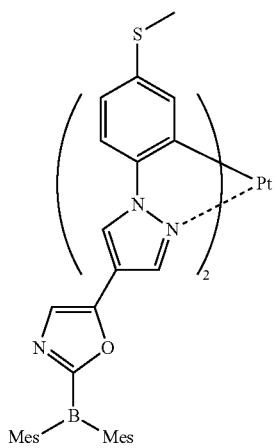
4-37
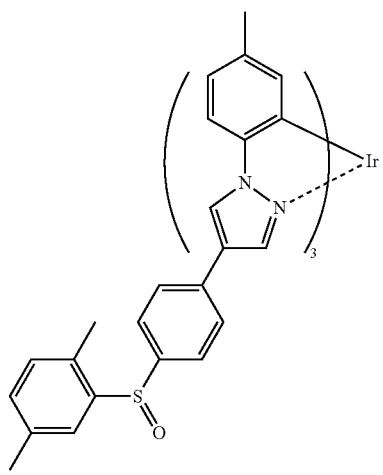
4-38
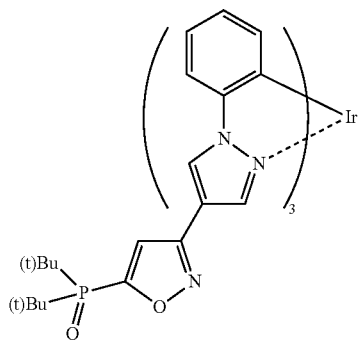
4-39
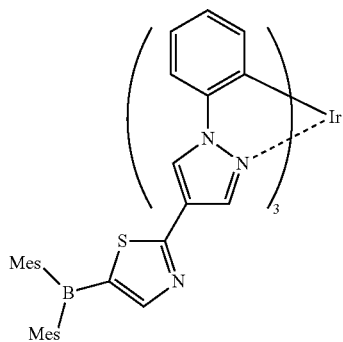
5-1
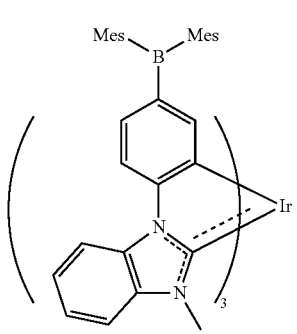
5-2
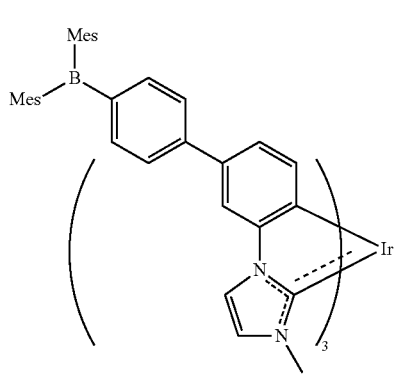
5-3
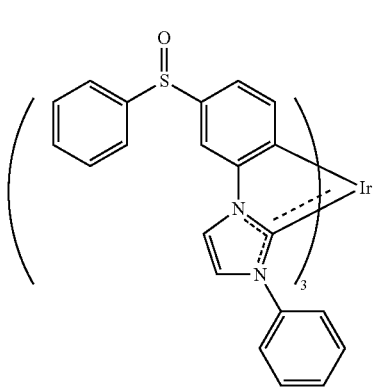
5-4
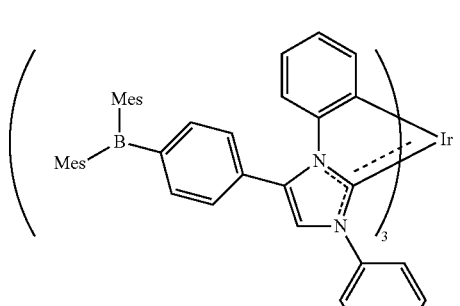

-continued
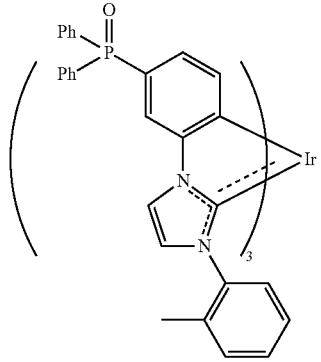
5-5
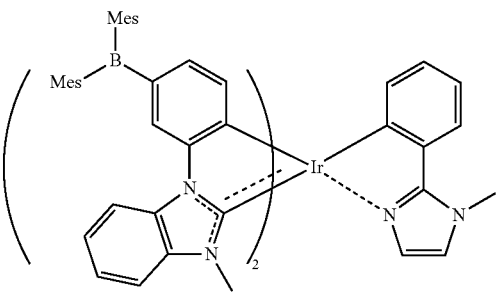
5-6
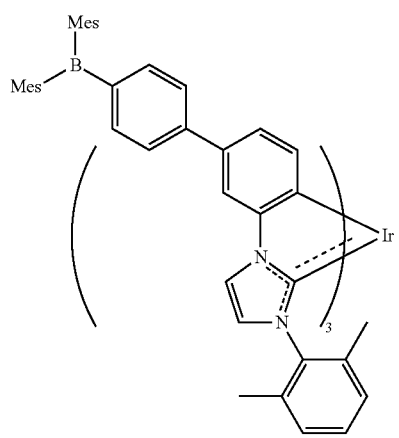
5-7
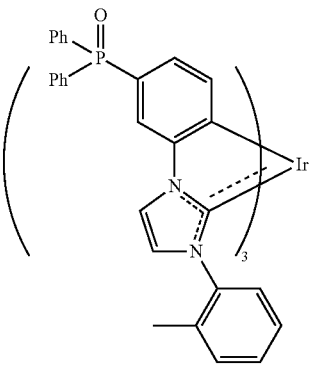
5-8
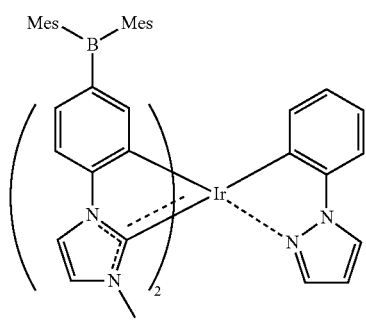
5-9
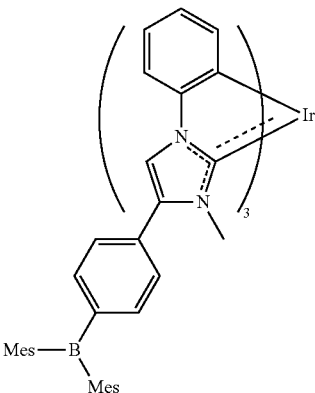
5-10
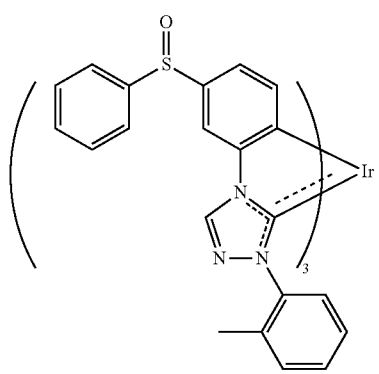
5-11
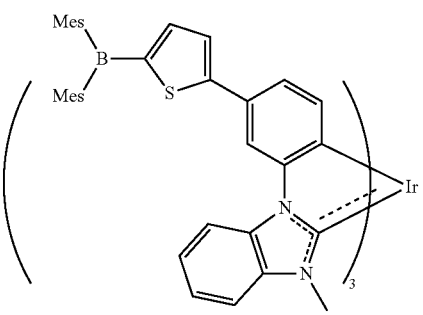
5-12

-continued
5-13
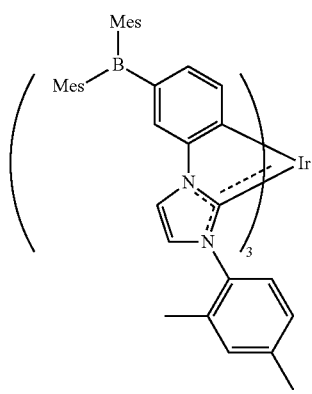
5-14
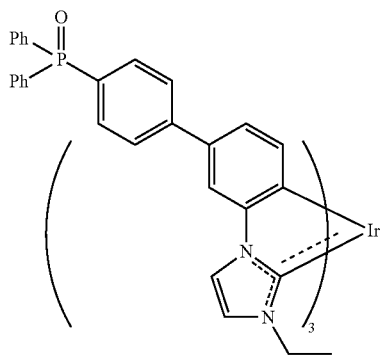
5-15
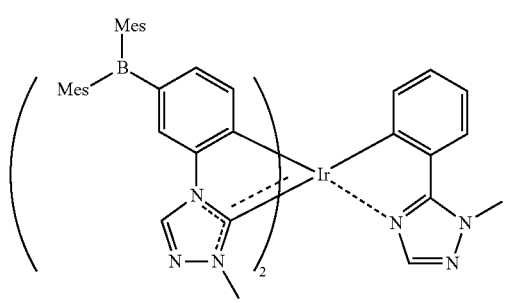
6-1
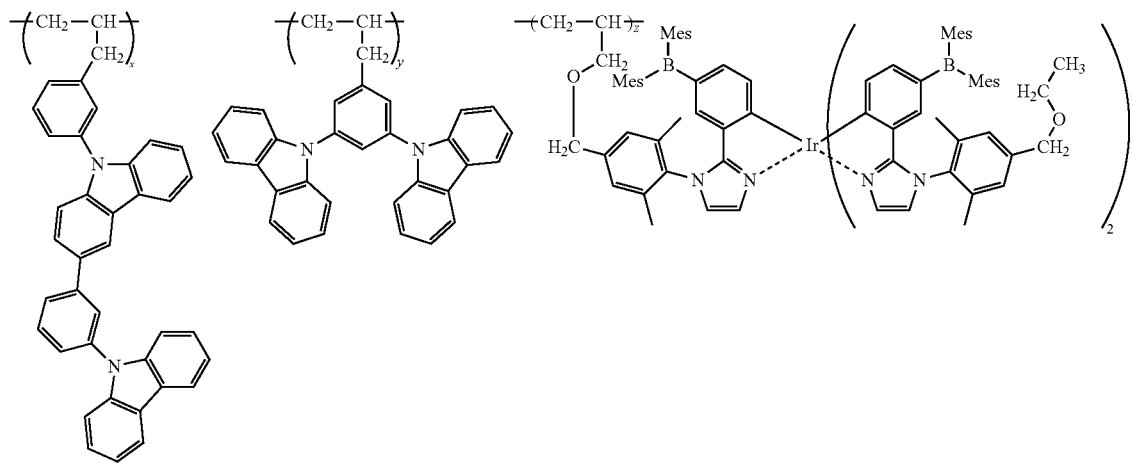
x:y:z = 70:20:10
random co-polymer -continued
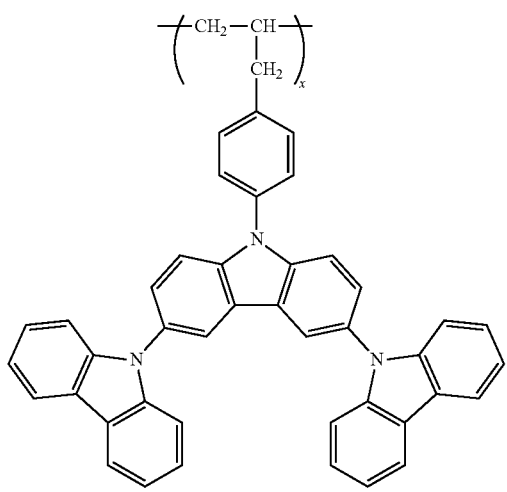
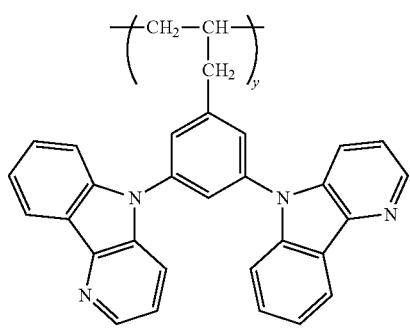
6-2
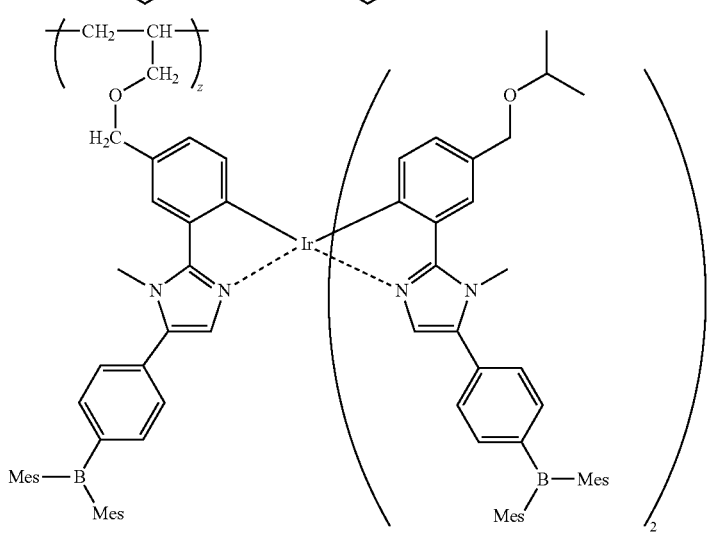
x:y:z = 80:10:10
random co-polymer
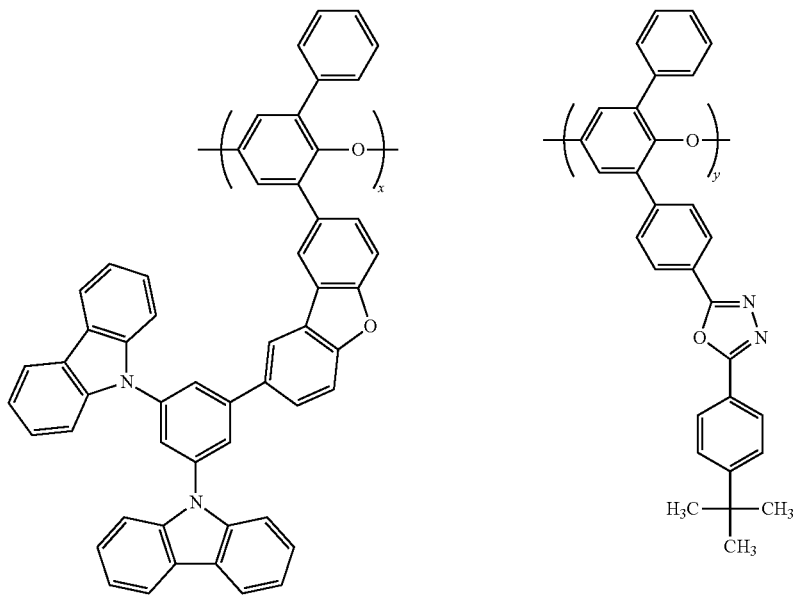
6-3

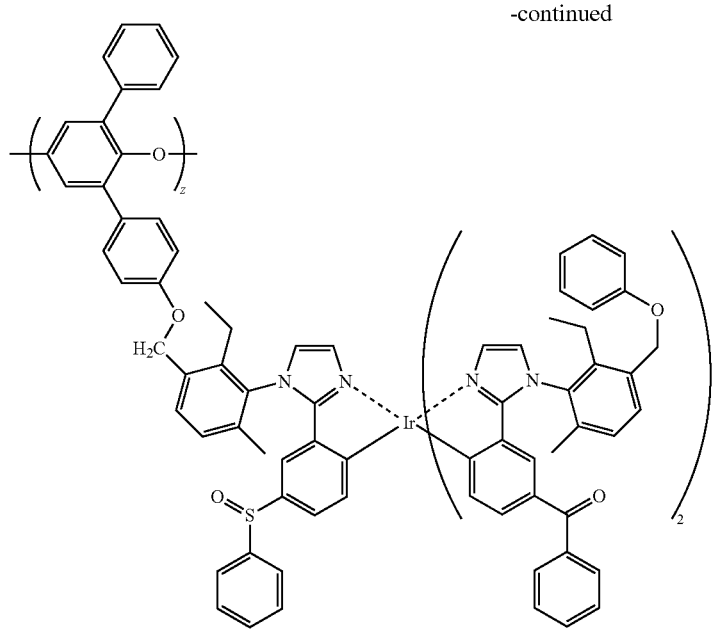
x:y:z = 80:10:10
random co-polymer
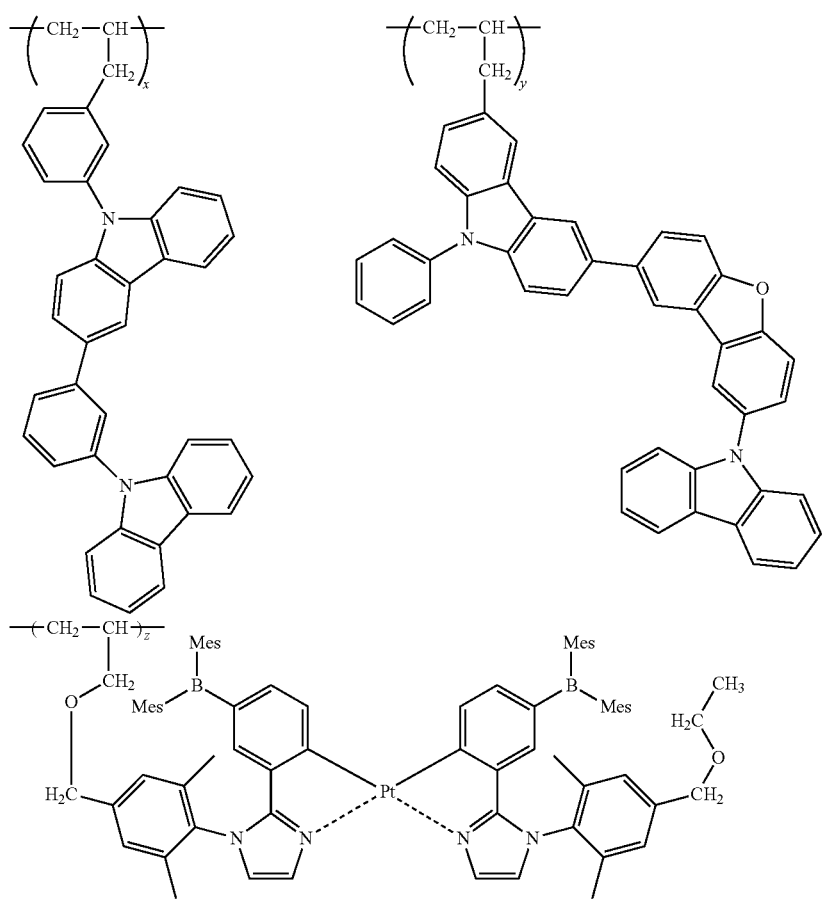
x:y:z = 70:20:10
random co-polymer
6-4

Metal complexes according to an organic EL element material of this invention can be synthesized by applying a method described in such as Organic Letter, vol. 3, No. 16, pp. 2579-2581 (2001), Inorganic Chemistry vol. 30, No. 8, pp. 1685-1687 (1991), J. Am. Chem. Soc., vol. 123, p. 4304 (2001 ), Inorganic chemistry vol. 40, No. 1, pp. 1704-1711 (2001), Inorganic Cbenastsy vol. 41, No. 12, pp. 3055-3066 (2002), New Journal of Chemistry, vol. 26, p. 1171 (2002), Organic Letter Vol. 8, No. 3 pp. 415-418 (2006), and reference documents described in these documents.

In the present invention, an emission wavelength is measured as follows. First, an absorption spectrum of an example compound is measured. Then, a maximum absorption wavelength in the range of 300 nm-350 nm is determined as an excitation light.

By using the determined excitation light, an emission wavelength is measured with a phosphorescent photometer F-4500 (made by Hitachi. Ltd.) while carrying out nitrogen gas bubbling.

Although there is no limitation to a used solvent, examples of preferably used solvents are 2-methyltetrahyoduran and dichloromethane from the viewpoint of solubility of a compound.

The density of the sample for measurement is preferable to be sufficiently diluted. Specifically, it is preferable to measure in the range of $10^{-6}$ mole/L to $10^{-4}$ mole/L.

Although there is no limitation to the temperature at the time of measurement it is generally preferable to set the temperature in the range of room temperature to 77 K.

<<Constituting Layers of Organic EL Element>>

The layers which constitute the organic EL element of the present invention will now be detailed. Preferred embodiments of the organic EL element of the present invention will be described below, however, the present invention is not limited to these.

(i) Anode/light emitting layer/electron transport layer/cathode (ii) Anode/hole transport layer/light emitting layer/electron transport layer/cathode (iii) Anode/hole transport layer/light emitting layer/hole blocking layer/electron transport layer/cathode (iv) Anode/hole transport layer/light emitting layer/hole blocking layer/electron transport layer/cathode buffer layer/cathode (v) Anode/anode buffer layer/hole transport layer/light emitting layer/hole blocking layer/electron transport layer/cathode buffer layer/cathode (vi) Anode/hole transport layer/anode buffer layer/light emitting layer/hole blocking layer/electron transport layer/cathode buffer layer/cathode (vii) Anode/anode buffer layer/hole transport, layer/light emitting layer/electron transport layer/cathode buffer layer/cathode The light emitting layer may form a unit to result in a light emitting layer unit. Further, it may be provided with a non-light emitting intermediate layer between the light emitting layers. In addition, the intermediate layer may contain a charge generating layer. The organic EL element of the present invention preferably emits a white light, and a lighting device employing this element is preferred.

Each of the layers which constitute the organic EL elements of the present invention will now be detailed.

<<Electron Transport Layer>>

An electron transport layer is composed of a material having a function to transfer an electron, and an electron injection layer and a hole blocking layer are included in an electron transport layer in a broad meaning. A single layer or plural layers of an electron transport layer may be provided.

As an electron transport material (including a hole blocking material and an electron injection material) used for an electron transport layer is only required to have a function of transporting electrons ejected from the cathode to the light emitting layer. As materials to form an electron transport layer, any of the conventional compounds may be selected and they can be employed singly or jointly.

Examples of them (hereinafter, they are called as an electron transport material) include: a nitro-substituted fluorene derivative, a diphenylquinone derivative, a thiopyradineoxide derivative, heterocyclic tetracarboxylic acid anhydride such as naphthalene perylene, carbodiimide, a fluorenylidenemethane derivative, anthraquinonedimethane, an anthrone derivative, an oxadiazole derivative, and an azacarbazole derivative including a carboline derivative.

Here, "an azacarbazole derivative" indicates a compound having a structure in which at least one of the carbon atoms constituting the carboline ring is replaced with one or more nitrogen atoms.

Further, as examples of an oxadiazole derivative described above, the following compounds can be used as an electron transport material: a thiadiazole derivative in which an oxygen atom in the oxadiazole ring is replaced with a sulfur atom; and a quinoxaline derivative which contains a quinoxaline ring known as an electron withdrawing group.

Polymer materials, in which these materials are introduced in a polymer chain or these materials form the main chain of polymer, can be also utilized.

Further, a metal complex of a 8-quinolinol derivative such as tris(8-quinolinol)aluminum ($Alq_3$), tris(5,7-dichloro-8-quinolinol)aluminum, tris(5,7-dibromo-8-quinolinol)aluminum, tris(2-methyl-8-quinolinol)aluminum, tris(5-methyl-8-quinolinol)aluminum and bis(8-quinolinol)zinc (Znq); and metal complexes in which a central metal of the aforesaid metal complexes is substituted by In, Mg, Cu, Ca, Sn, Ga or Pb, can be also utilized as an electron transport material.

Further, metal-free or metal phthalocyanine, or a compound whose terminal is substituted by an alkyl group or a sulfonic acid group, can be preferably utilized as an electron transport material.

In the same manner as for a hole injection layer and hole transport layer, an inorganic semiconductor such as an n-type-Si and an n-type-SiC can be also utilized as an electron transport material.

An electron transport layer is preferably formed in a film with an election transport material by the following methods, for example: a vacuum deposition method and a wet method (it is also called as a wet process. Examples of a wet process include: a spin coating method, a cast method, a the coating method, a blade coating method, a roll coating method, an inkjet method, a printing method, a spray coating method, a curtain coating method, and a LB method (Langmuir Blodgett method).

The preparation method of the constituting layers of the organic EL element will he described in detain in the portion of preparation of an organic EL element.

The layer thickness of the electron transport layer of the present invention is not specifically limited; however, it is generally 5 nm-5,000 nm, and preferably it is 5 nm-200 nm. This electron transport layer may be a single layer structure containing of one or more types of the above described materials.

Further, it is possible to employ an electron transport layer of a higher n property which is doped with impurities. As its example, listed are those described in each of JP-A Nos. 4-297076, 10-270172, 2000-196140, 2001-102175, as well as in J. Appl. Phys., 95, 5773 (2004).

Next there will be listed specific example compounds (electron transport materials) known in the art and preferably used in the electron transport layer of the white emission organic EL element. However, the present invention is not limited to these.

ET-1

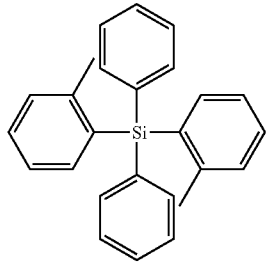

ET-2(BCP)

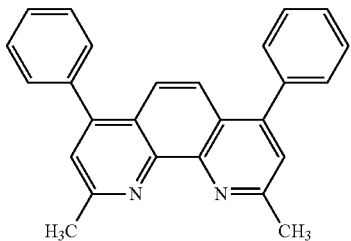

ET-3(PBD)

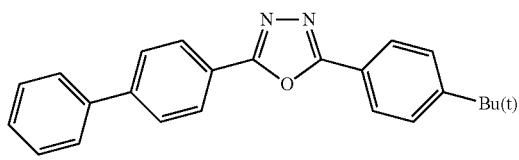

ET-4

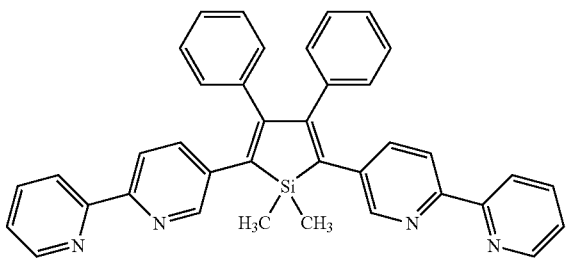

ET-5

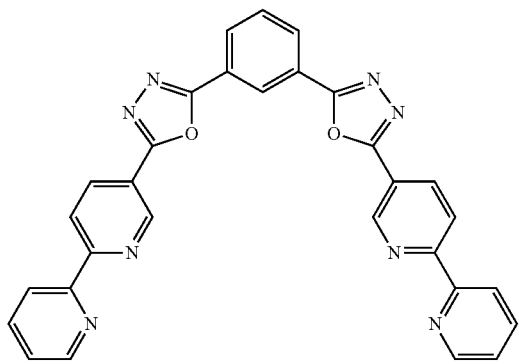

ET-6

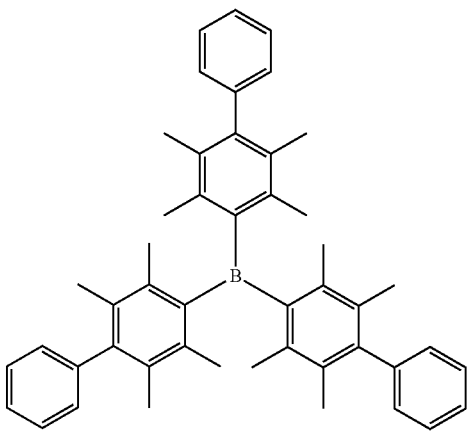

ET-7(Alq₃)

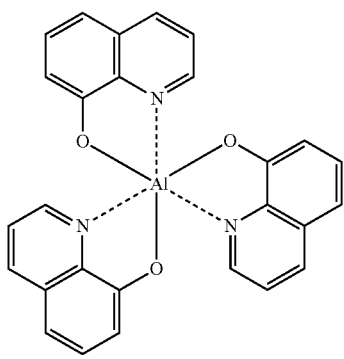

ET-8(BAlq)

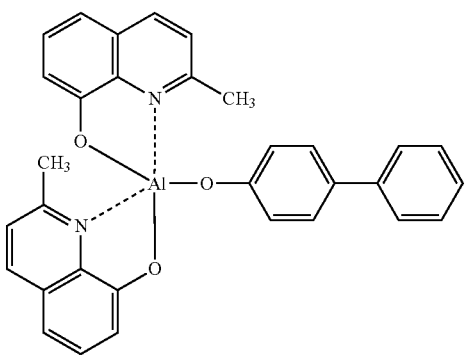

-continued
ET-9
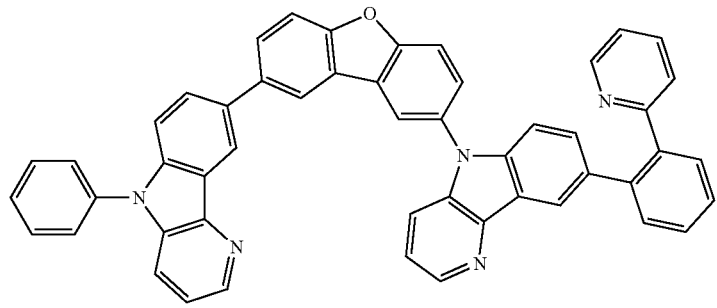
ET-10
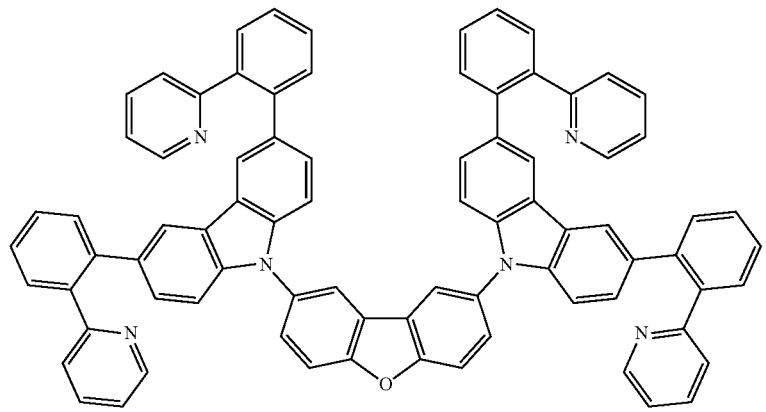
ET-11
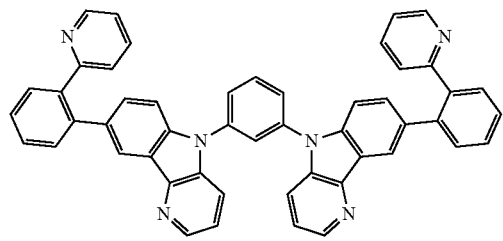
ET-12
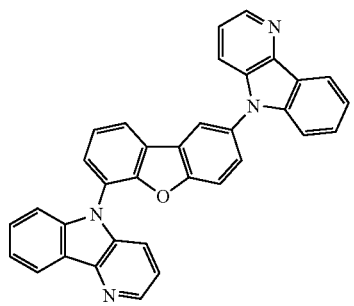
ET-13
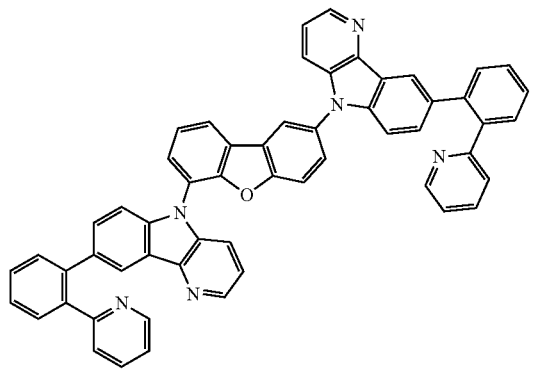
ET-14
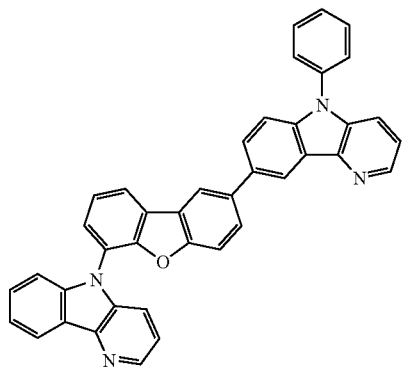

-continued
ET-15
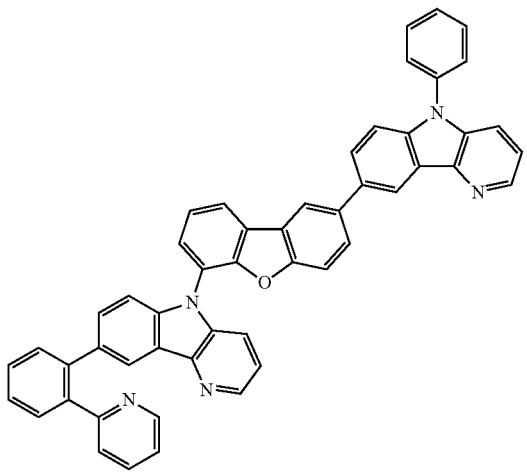
ET-16
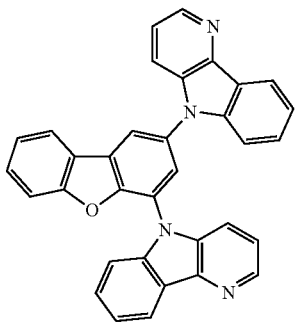
ET-17
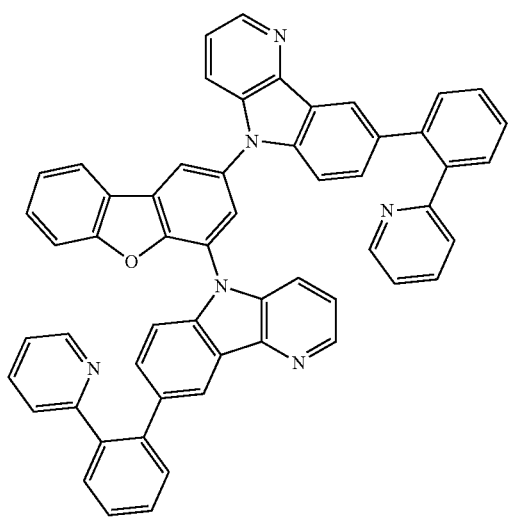
ET-18
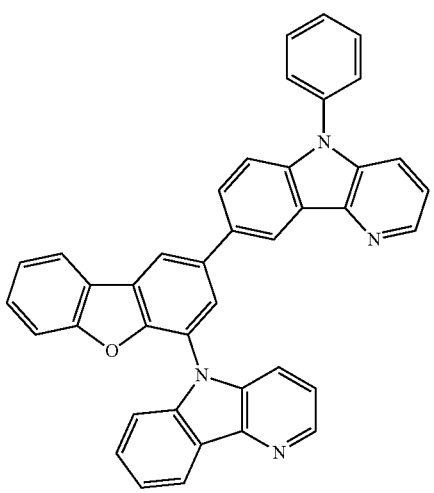
ET-19
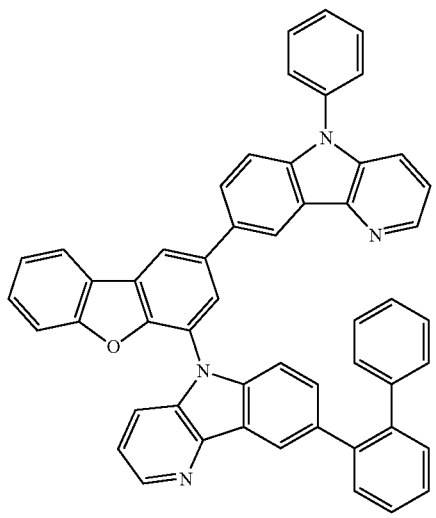
ET-20
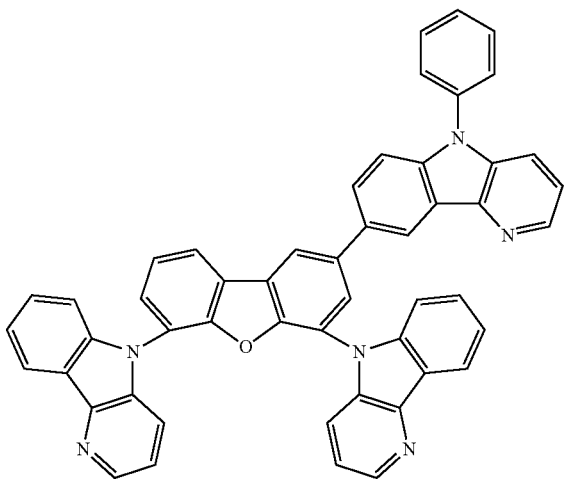

-continued
ET-21
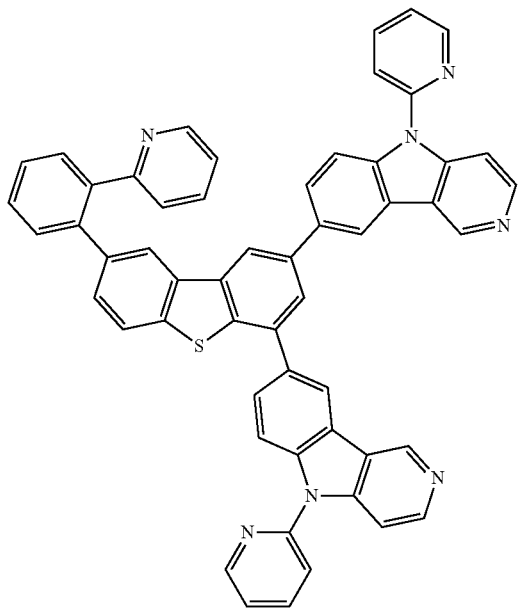
ET-22
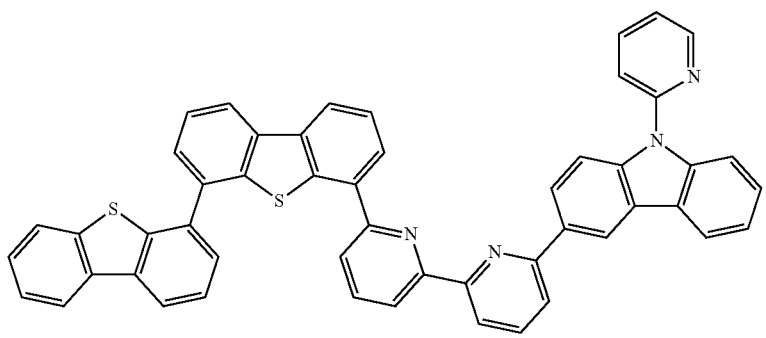
ET-23
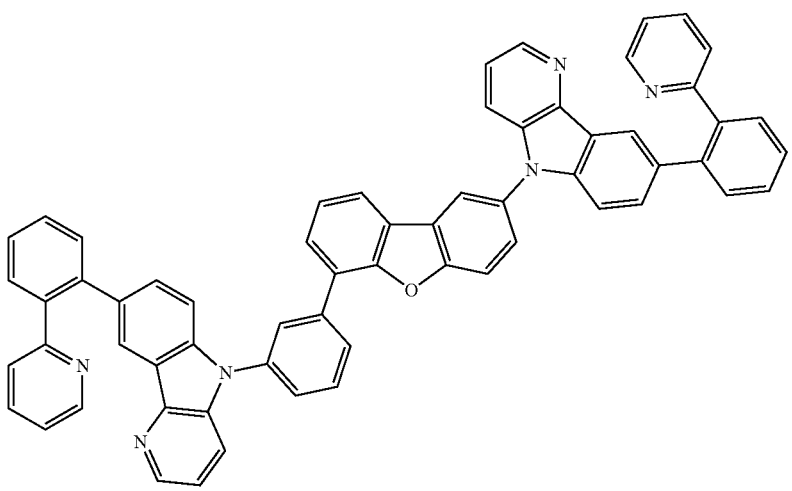

ET-24
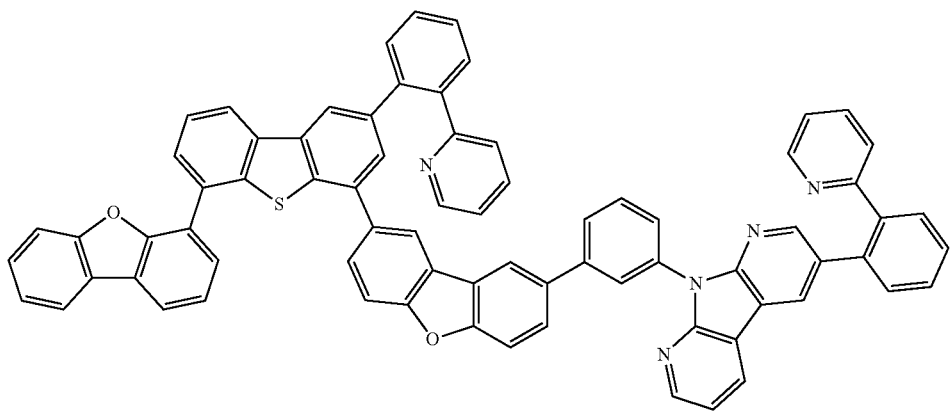
ET-25
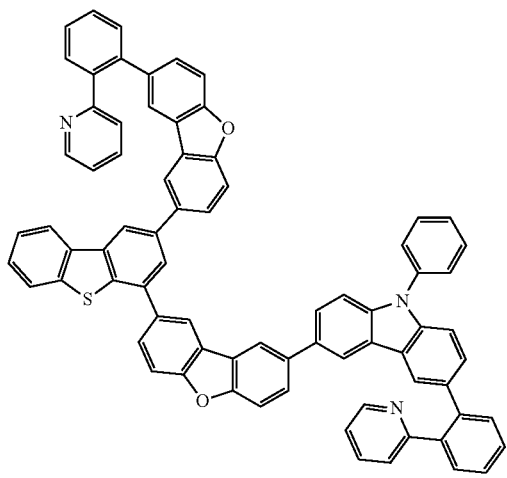
ET-26
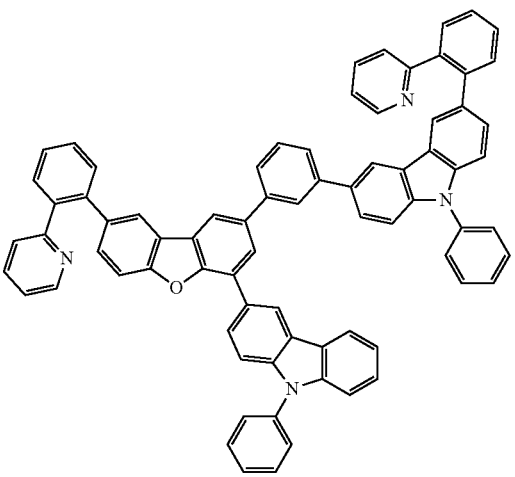
ET-27
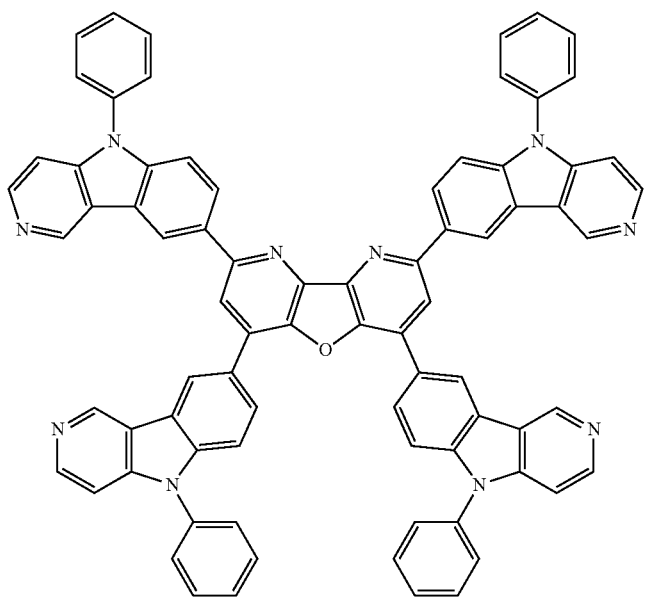

ET-28
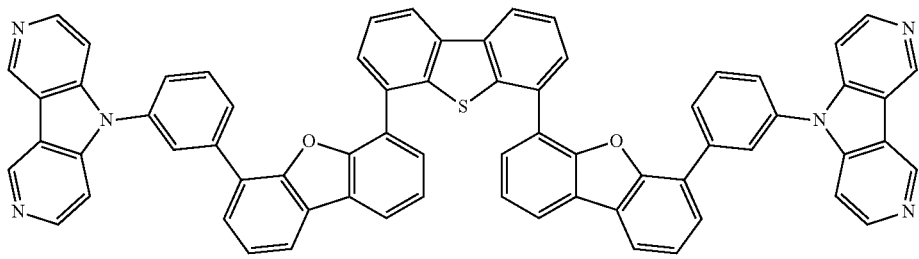
ET-29
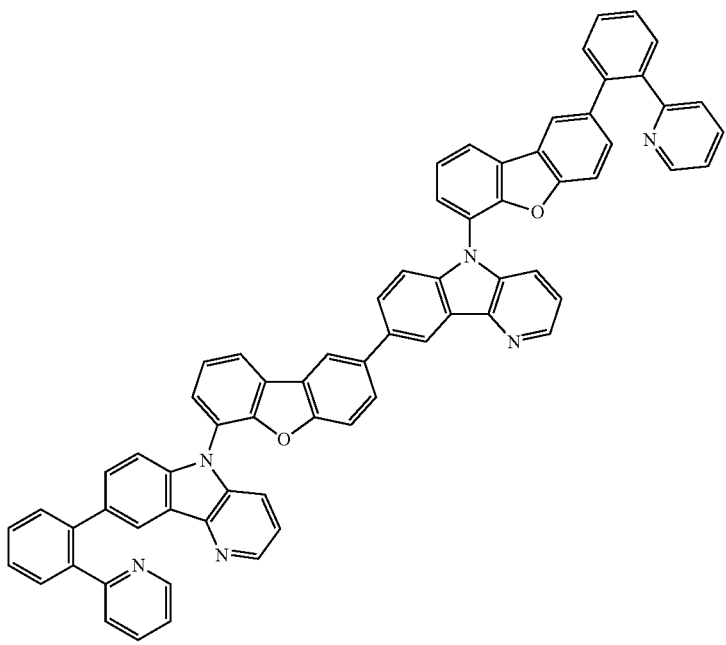
ET-30
ET-31
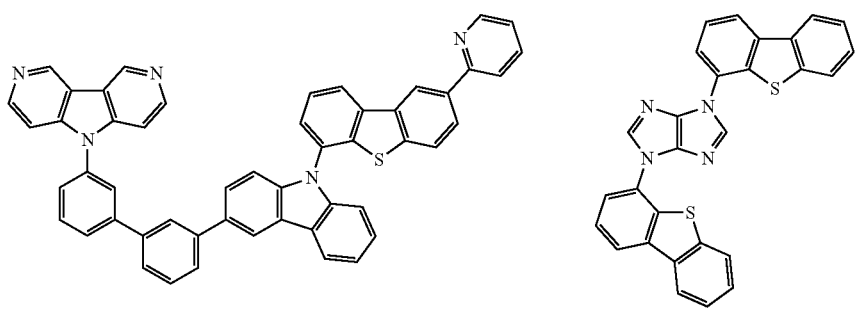

ET-32
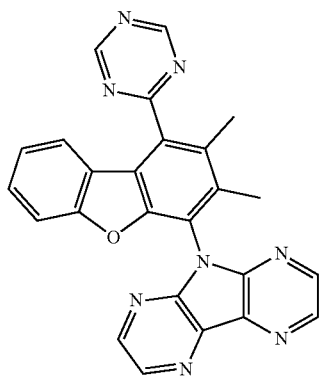
ET-33
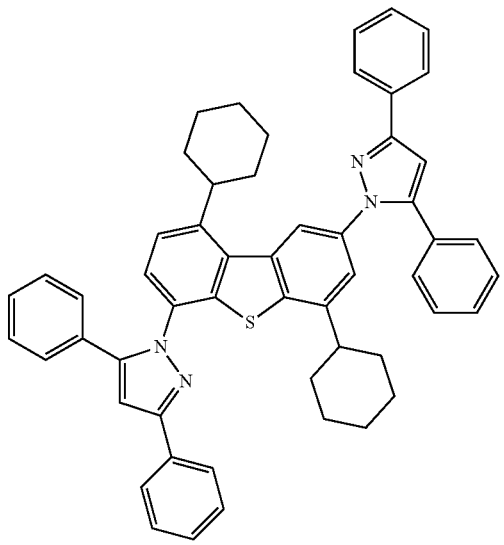
ET-34
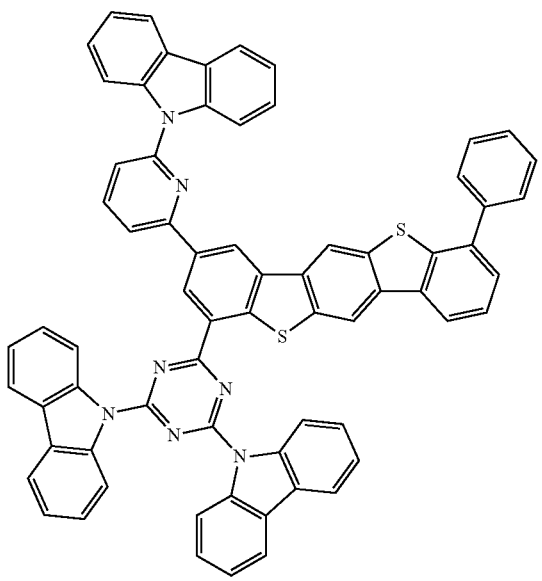
ET-35
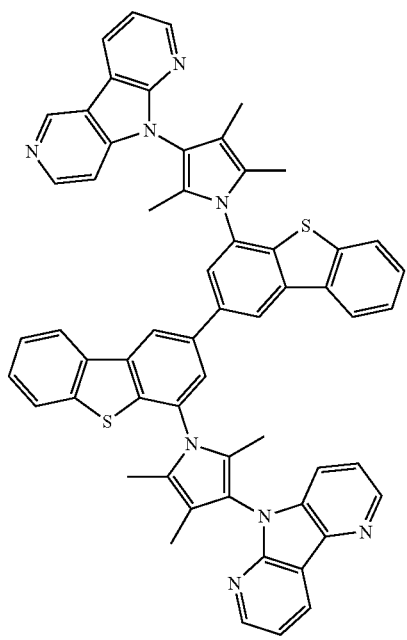
ET-36
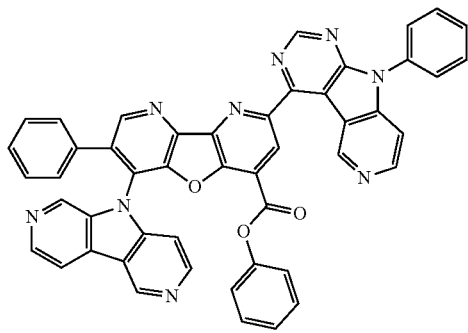
ET-37
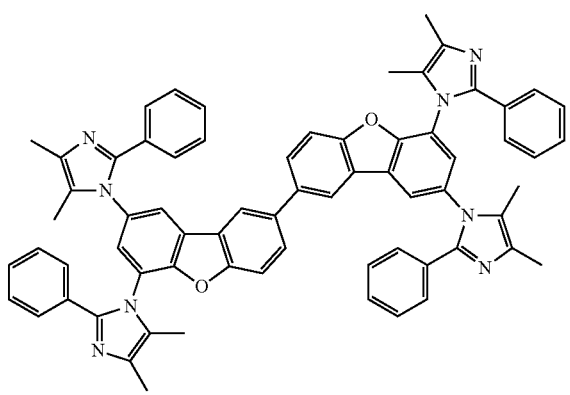

-continued

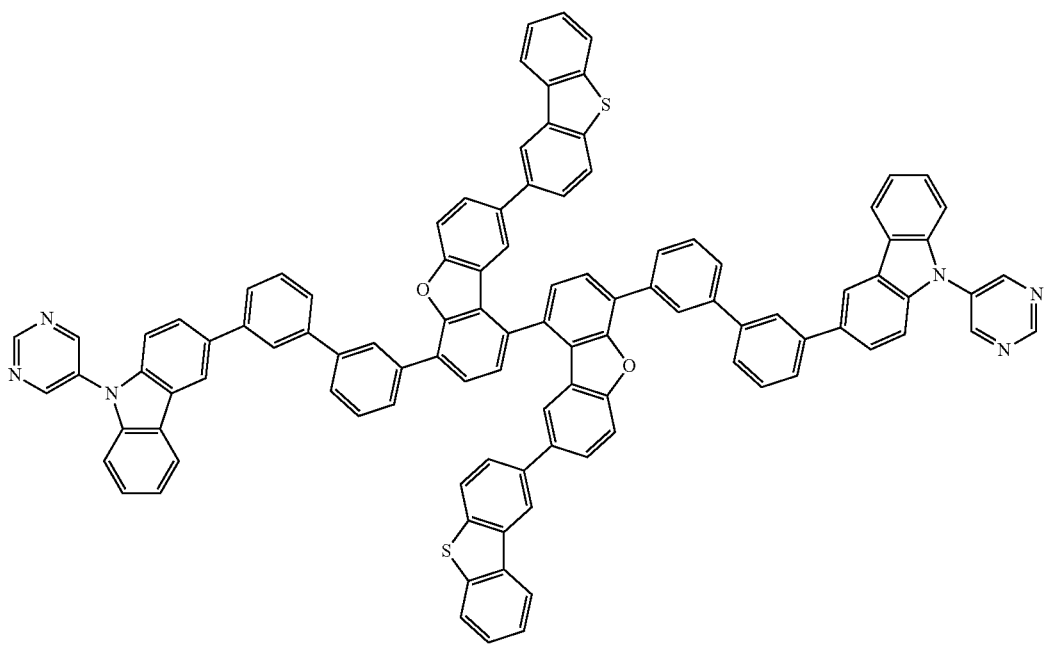

ET-38

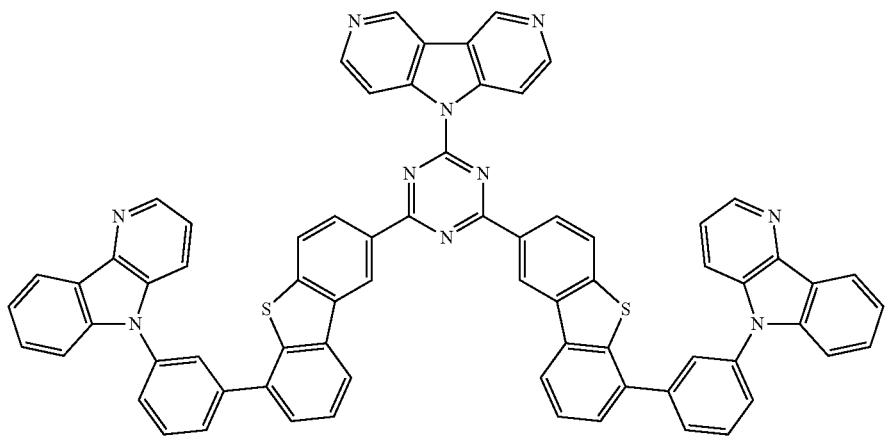

ET-39

A compound represented the following Formula (R-1) is more preferably used for forming an electron transport layer of an organic EL element of the present invention.

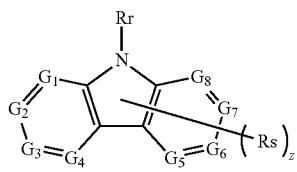

R-1

In the formula, Rr represents an alkyl group, a cycloalkyl group, an aromatic hydrocarbon group, or an aromatic heterocyclic group. Although Rs represents a substituent, a preferably used substituent as Rs is an alkyl group, a cycloalkyl group, an aromatic hydrocarbon group, or an aromatic heterocyclic group. Especially preferable Rs is an aromatic hydrocarbon group or an aromatic heterocyclic group.

An alkyl group represented by Rr in Formula (R-1) is synonymous with an alkyl group each represented by Ra, Rb and Rc in Q-1, Q-2 and Q-3 in Formula (1).

A cycloalkyl group represented by Rr in Formula (R-1) is synonymous with a cycloalkyl group each represented by Ra, Rb and Rc in Q-1, Q-2 and Q-3 in Formula (1).

An aromatic hydrocarbon group represented by Rr in Formula (R-1) is synonymous with an aromatic hydrocarbon group each represented by Ra, Rb and Rc in Q-1, Q-2 and Q-3 in Formula (1).

An aromatic heterocyclic group represented by Rr in Formula (R-1) is synonymous with an aromatic heterocyclic group each represented by Ra, Rb and Rc in Q-1, Q-2 and Q-3 in Formula (1).

A substituent represented by Rs in Formula (R-1) is synonymous with a substituent which may be substituted on a 6-membered aromatic hydrocarbon ring, and a 5- or 6-membered aromatic heterocycle represented by A and B in Formula (1).

An alkyl group preferably used for Rs in Formula (R-1) is synonymous with an alkyl group each represented by Ra, Rb and Rc in Q-1, Q-2 and Q-3 in Formula (1).

A cycloalkyl group preferably used for Rs in Formula (R-1) is synonymous with a cycloalkyl group each represented by Ra, Rb and Rc in Q-1, Q-2 and Q-3 in Formula (1).

An aromatic hydrocarbon group preferably used for Rs in Formula (R-1) is synonymous with an aromatic hydrocarbon group each represented by Ra, Rb and Rc in Q-1, Q-2 and Q-3 in Formula (1).

An aromatic heterocyclic group preferably used for Rs in Formula (R-1) is synonymous with an aromatic heterocyclic group each represented by Ra, Rb and Rc in Q-1, Q-2 and Q-3 in Formula (1).

<<Light Emitting Layer>>

The light emitting layer of the present invention is a layer, which emits light via recombination of electrons and holes injected from an electrode or a layer such as an electron transport layer or a hole transport layer. The light emission portion may be present either within the light emitting layer or at the interface between the light emitting layer and an adjacent layer thereof.

The total thickness of the light emitting layer is not particularly limited. However, in view of the layer homogeneity, the minimization of application of unnecessary high voltage during light emission, and the stability enhancement of the emitted light color against the drive electric current, the layer thickness is regulated preferably in the range of 2 nm-5 μm, more preferably in the range of 2 nm-200 nm, but most preferably in the range of 5 nm-100 nm.

The light emitting layer can be prepared by forming a thin layer made of a light emitting dopant and a host compound, which will be described later, with a vacuum evaporation method or a wet preparation method. A wet preparation method is also called as a wet process, and examples of this include: a spin coating method, a east method, a the coating method, a blade coating method, a roll coating method, an inkjet method, a printing method, a spray coating method, a curtain coating method, and a LB method (Langmuir Blodgett method).

When a compound represented by Formula (1) relating to the present invention is used in a light emitting layer, it is preferable to form the layer with a wet process.

It is preferable that the light emitting layer of the organic EL element of the present, invention incorporates a light emitting dopant (a phosphorescent emitting dopant (or it is called as a phosphorescence dopant or a phosphorescence emitting dopant group) or a fluorescent dopant) and a light emitting host compound.

(Light Emitting Dopant Compound)

The light emitting dopant compound (it may be called as the light emitting dopant) of the present, invention will now be described.

As light emitting dopants according to the present invention, it can be employed fluorescent dopants (also referred to as fluorescent compounds) and phosphorescent dopants (also referred to as phosphorescent emitting materials, phosphorescent compounds or phosphorescence emitting compounds).

(Phosphorescent Dopant (also referred to as Phosphorescence emitting dopant))

A phosphorescence dopant of the present invention will be described.

The phosphorescent dopant of the present invention is a compound, wherein emission from an excited, triplet state thereof is observed, specifically, emitting phosphorescence at room temperature (25° C.) and exhibiting a phosphorescence quantum yield of at least 0.01 at 25° C. The phosphorescence quantum yield is preferably at least 0.1.

The phosphorescence quantum yield can be determined via a method described in page 398 of Bunko II of Dai 4 Han Jikken Kagaku Koza 7 (Spectroscopy II of 4th Edition Lecture of Experimental Chemistry 7) (1992, published by Maruzen Co., Ltd.). The phosphorescence quantum yield in a solution can be determined using appropriate solvents. However, it is only necessary for the phosphorescent dopant of the present invention to exhibit the above phosphorescence quantum yield (0.01 or more) using any of the appropriate solvents.

Two kinds of principles regarding emission of a phosphorescent dopant are cited. One is an energy transfer-type, wherein carriers recombine on a host compound on which the carriers are transferred to produce an excited state of the host compound, and then via transfer of this energy to a phosphorescent dopant, emission from the phosphorescence-emitting dopant is realized. The other is a carrier trap-type, wherein a phosphorescence-emitting dopant serves as a carrier trap and then carriers recombine on the phosphorescent dopant to generate emission from the phosphorescent dopant. In each case, the excited state energy of the phosphorescent dopant is required to be lower than that of the host compound.

As a light emitting dopant relating to an organic EL element of the present invention, it is concluded a compound (a metal complex) represented by any one of the above-described Formula (1), Formula (2), Formula (3), Formula (4) and Formula (5). The light emitting layer of the present invention may further incorporate the compounds described in the following patent documents.

The patent documents are: WO 00/70655, JP-A Nos. 2002-280178, 2001-181616, 2002-280179, 2001-181617, 2002-280180, 2001-247859, 2002-299060, 2001-313178, 2002-302671, 2001-345183 and 2002-324679, WO 02/15645, JP-A Nos. 2002-332291, 2002-50484, 2002-322292 and 2002-83684, Japanese Translation of PCT International Application Publication No, 2002-540572, JP-A Nos. 2002-117978, 2002-338588, 2002-170684 and 2002-352960, WO 01/93642, JP-A Nos. 2002-50483, 2002-100476, 2002-173674, 2002-359082, 2002-175884, 2002-363552, 2002-184582 and 2003-7469, Japanese Translation of PCT International Application Publication No. 2002-525808, JP-A 2003-7471, Japanese Translation of PCT International Application Publication No. 2002-525833, JP-A Nos. 2003-31366, 2002-226495, 2002-234894, 2002-235076, 2002-241751, 2001-319779, 2001-319780, 2002-62824, 2002-100474, 2002-203679, 2002-343572 and 2002-203678. 2002-203679, 2002-343572 and 2002-203678.

(Fluorescent Dopants (also referred to as Fluorescent Compounds))

As fluorescent dopants, listed are compounds exhibiting a high fluorescent quantum efficiency such as: coumarin based dyes, pyran based dyes, cyanine based dyes, croconium based dyes, squarylium based dyes, oxobenzanthracene based dyes, fluorescein based dyes, Rhodamine based dyes, pyrylium based dyes, perylene based dyes, stilbene based dyes, polythiophene based dyes, rare earth complex based fluorescent materials, or laser dyes.

Moreover, two or more sorts of compounds may be combined together and used for the light emitting dopants of the present invention. It is possible to use in combination with phosphorescence dopants each having a different structure or to use in combination of a fluorescence dopant and a phosphorescence dopant.

Hereafter, there will be listed specific examples of a known light emitting dopant which may be used in combination with a compound (a metal complex) represented by any one of the above-described Formula (1), Formula (2), Formula (3), Formula (4) and Formula (5) relating to the present invention as a light emitting dopant. The present invention is not limited to them.
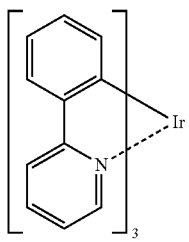 D-1
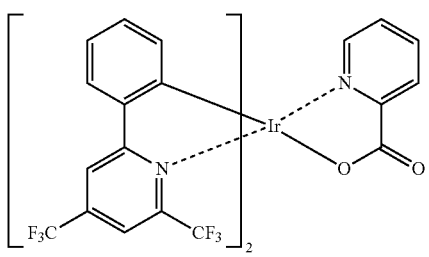 D-2
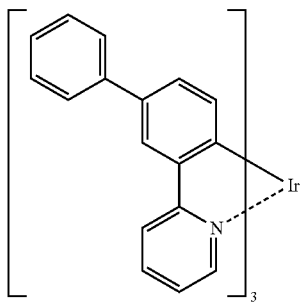 D-3
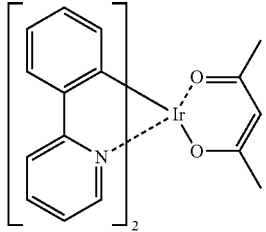 D-4
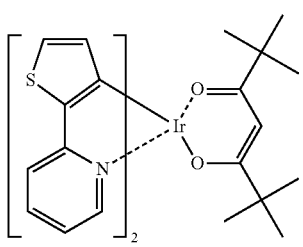 D-5
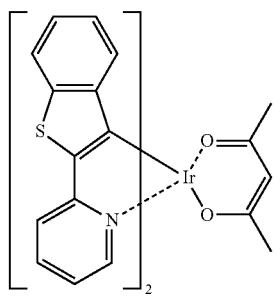 D-6
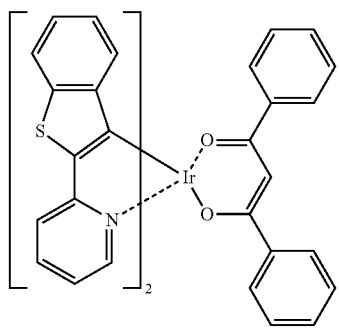 D-7
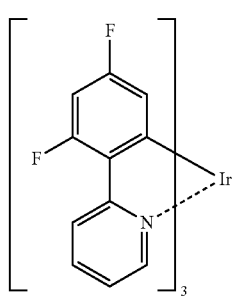 D-8
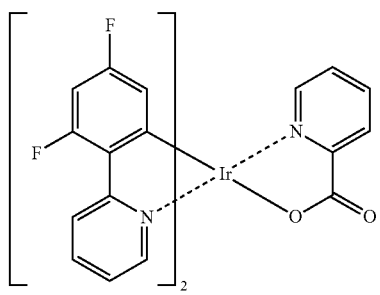 D-9
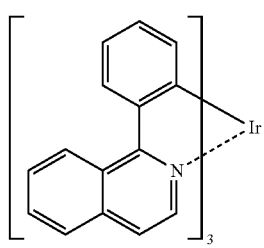 D-10

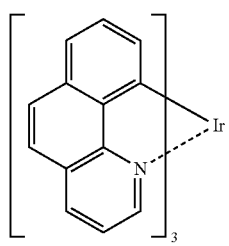
D-11
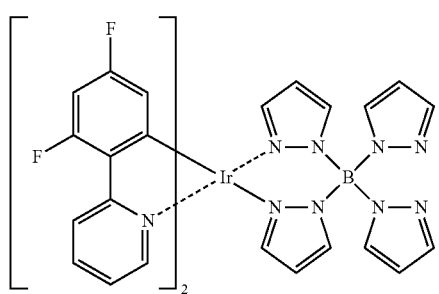
D-12
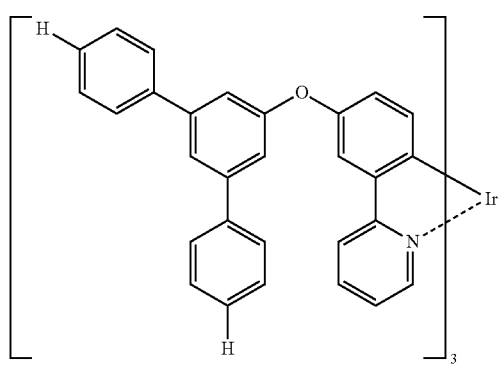
D-13
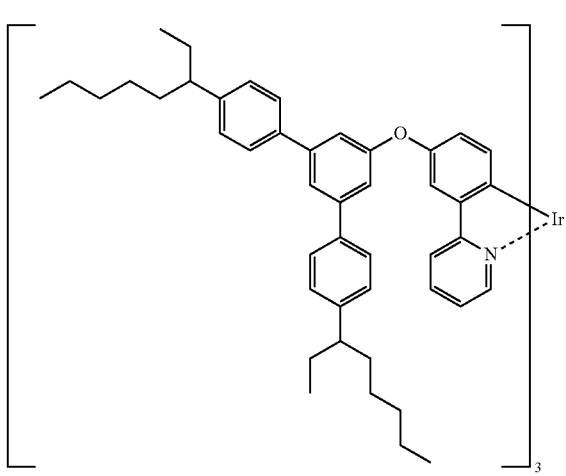
D-14
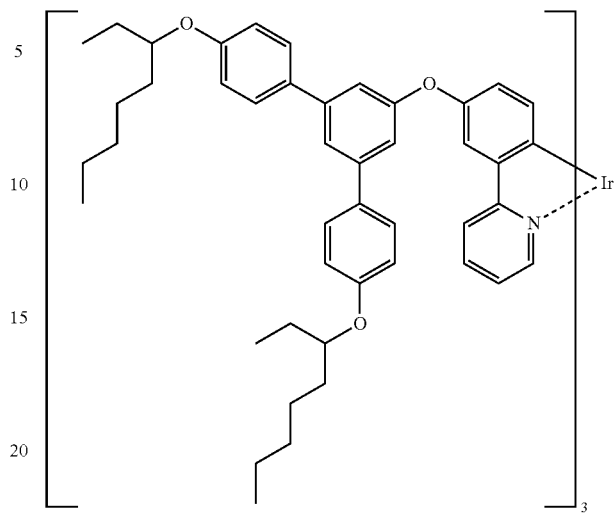
D-15
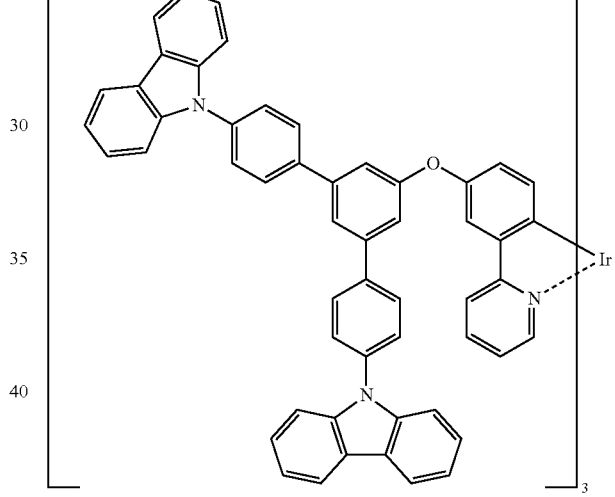
D-16
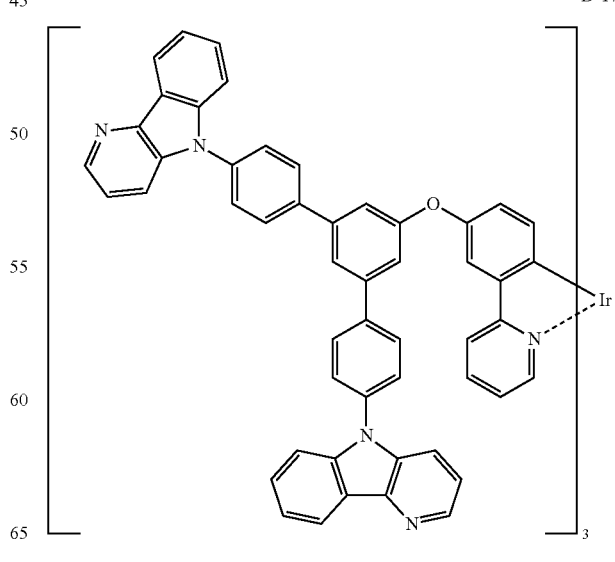
D-17

-continued
D-18
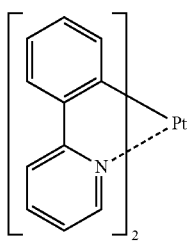
D-19
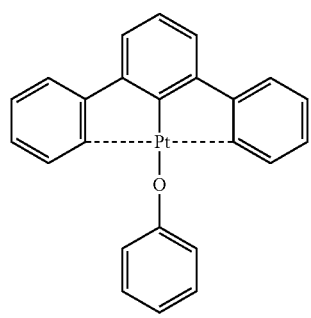
D-20
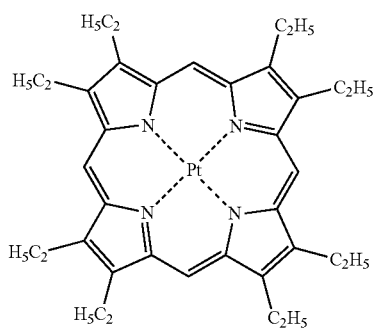
D-21
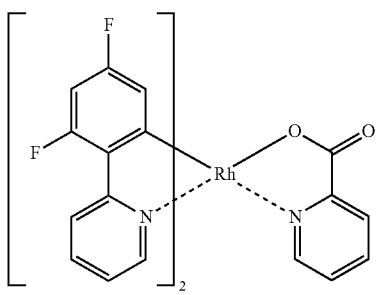
D-22
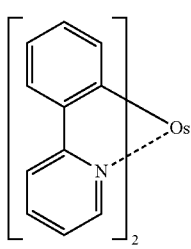
-continued
D-23
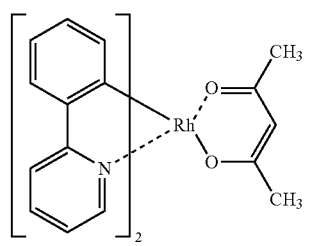
D-24
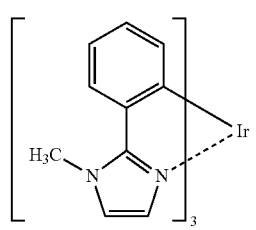
D-25
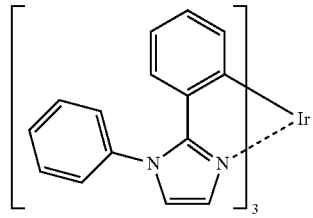
D-26
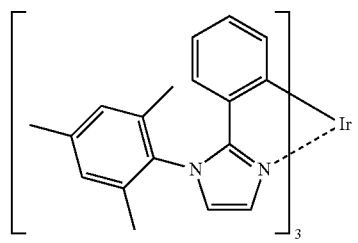
D-27
D-28
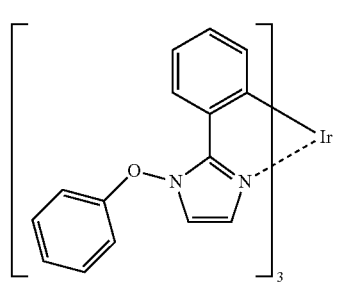

-continued
D-29
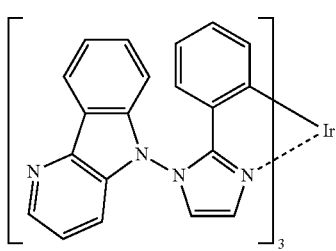
D-30
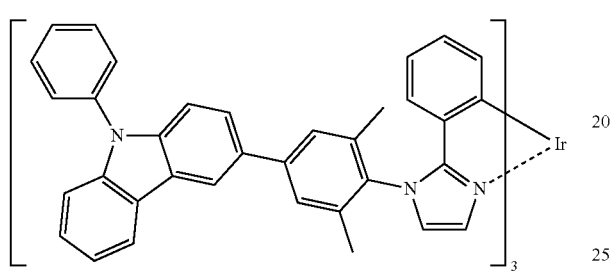
D-31
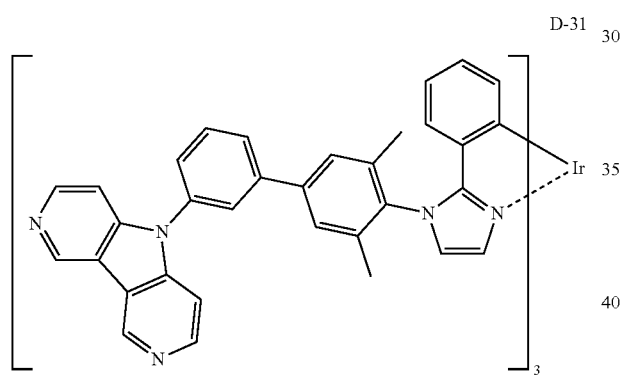
D-32
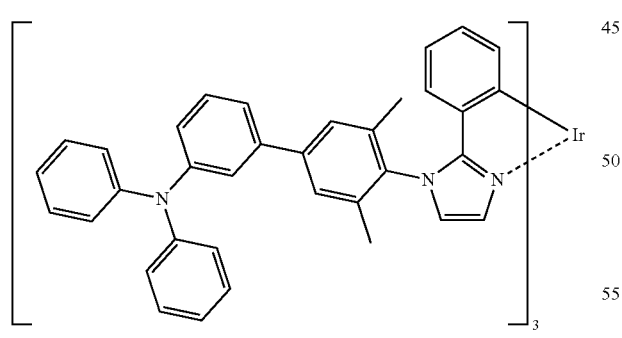
D-33
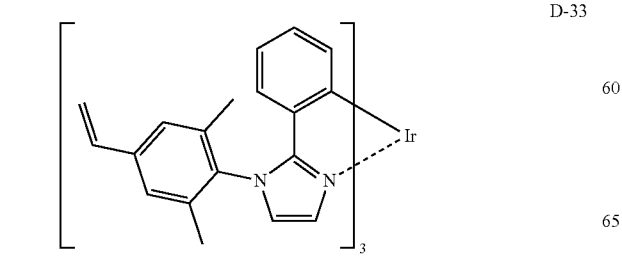
-continued
D-34
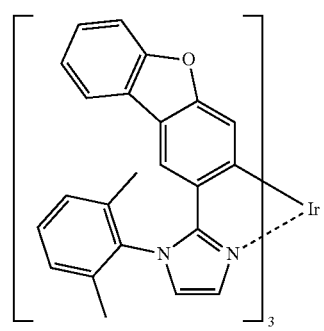
D-35
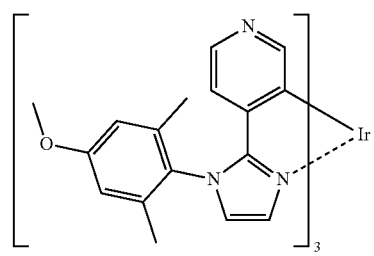
D-36
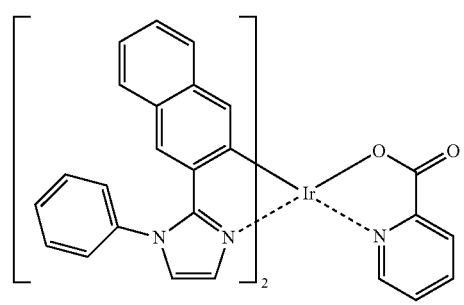
D-37
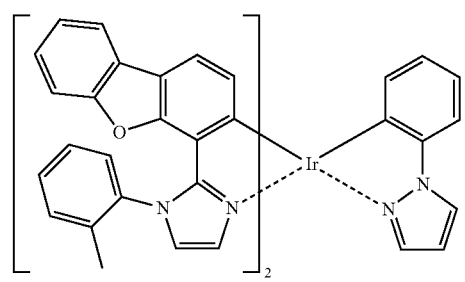
D-38
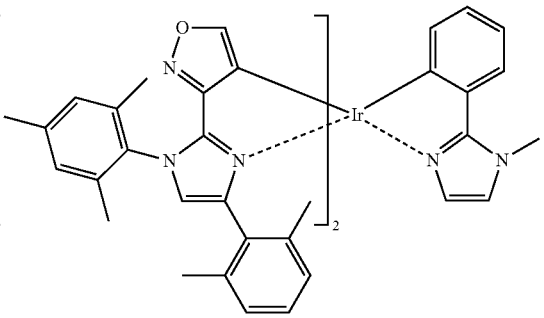

-continued
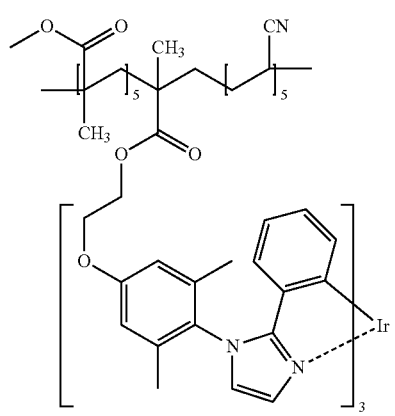
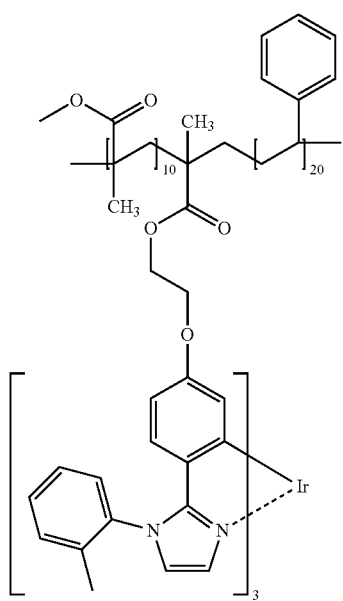
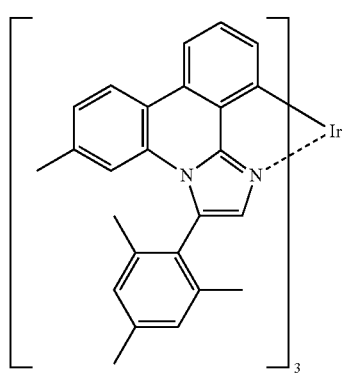
-continued
D-42
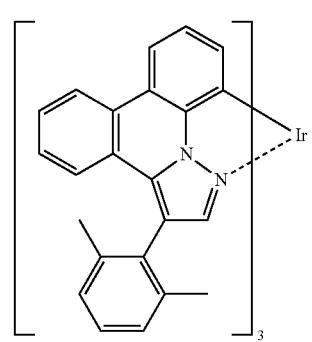
D-43
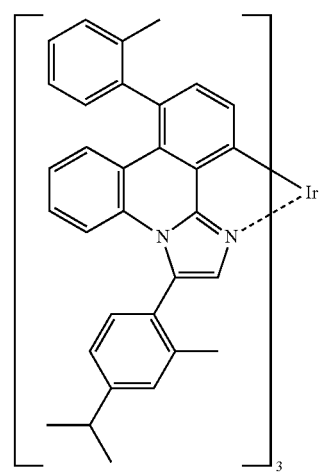
D-44
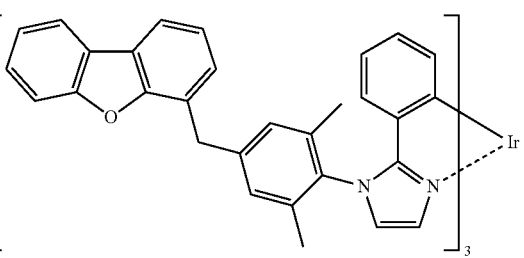
D-45
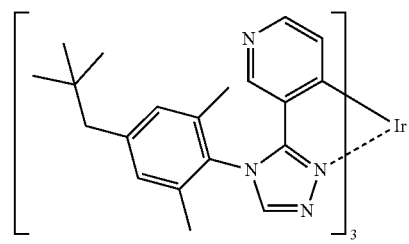
D-46
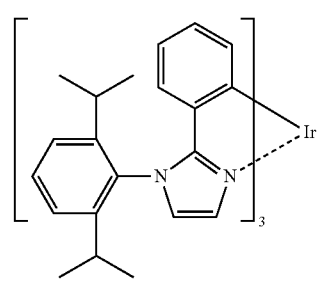

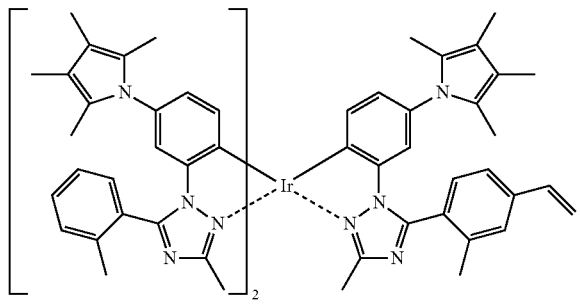

D-47

(Light Emitting Host Compound (also referred to as alight emitting host))

"Host compounds" as described in the present invention, are defined as compounds, incorporated in a light emitting layer, which result in a weight ratio of at least 20% in the above layer and also result in a phosphorescent quantum yield of the phosphorescence emission of less than 0.1 at room temperature (25° C.). Preferably, the phosphorescent quantum yield is less than 0.01. Further, among the compounds incorporated in the light emitting layer, it is preferable that the weight ratio of the host compound in the aforesaid layer is at least 20%.

Structures of the light emitting host employed in the present invention are not particularly limited. The conventionally known host compounds in organic EL elements can be used. Representative compounds include those having a basic skeleton such as carbazole derivatives, triarylamine derivatives, aromatic compound derivatives, nitrogen-containing heterocyclic compounds, thiophene derivatives, furan derivatives, oligoarylene compounds, carboline derivatives, or diazacarbazole derivatives (here, "a diazacarbazole derivative" indicates a ring structure in which at least one of the carbon atoms constituting the carboline ring is replaced with a nitrogen atom).

A known light emitting host which may be used in the present invention is preferably a compound having a hole transporting ability and an electron transporting ability, as well as preventing elongation, of an emission wavelength and having a high Tg (a glass transition temperature).

It may be used a light emitting host compound of the present invention singly or it may be used in combination with plural host compounds, which may be other host compound of the present invention or a known host compound.

It is possible to control the transfer of charges by making use of a plurality of host compounds, which results in high efficiency of an organic EL element.

In addition, it is possible to mix a different emission lights by making use of a plurality of known phosphorescent dopants as described above. Any required emission color can be obtained thereby.

Further, a light emitting host used in the present invention may be either a low molecular weight compound or a polymer compound having a repeating unit, in addition to a low molecular weight compound provided with a polymerizing group such as a vinyl group and an epoxy group (a polymerizable light emitting host). These compounds may be used singly or in combination of two or more compounds.

As specific examples of a light emitting host compounds, the compounds described in the following Documents are preferable.

For example, JP-A Nos. 2001-257076, 2002-308855, 2001-313179, 2002-319491-2001-357977, 2002-334786, 2002-8860, 2002-334787, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084 and 2002-308837.

Examples of the conventionally known compounds used as a light emitting host in the light emitting layer of the organic EL element of the present invention are given in the following, however, the present invention is not limited to these.

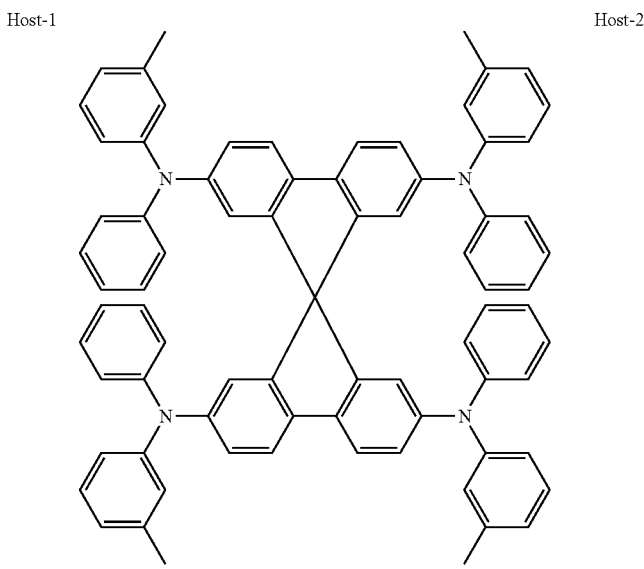

-continued
Host-3
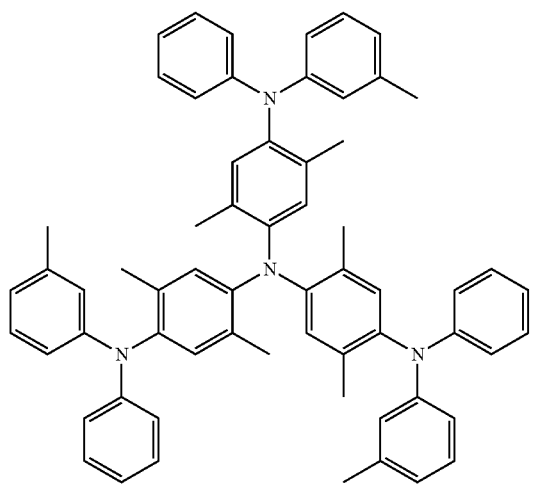
Host-4
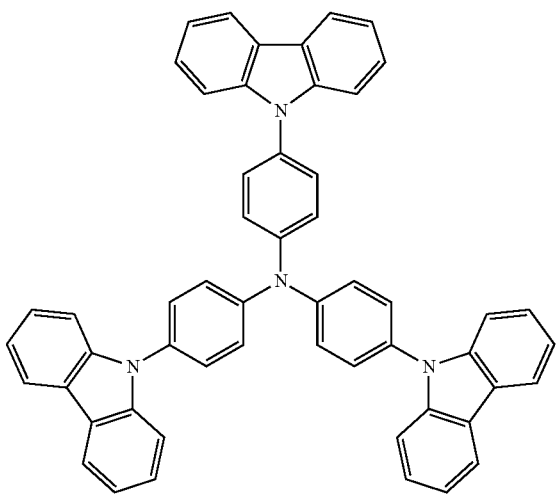
Host-5
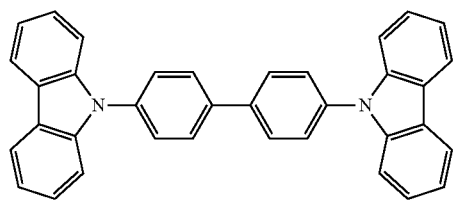
Host-6
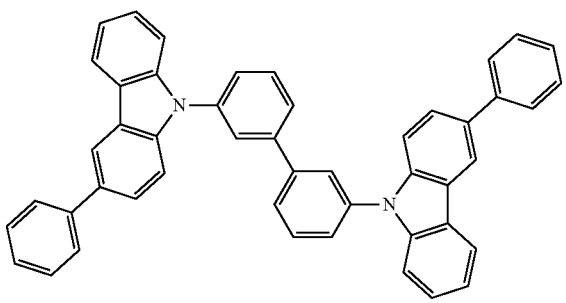
Host-7
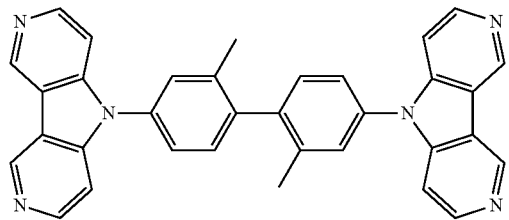
Host-8
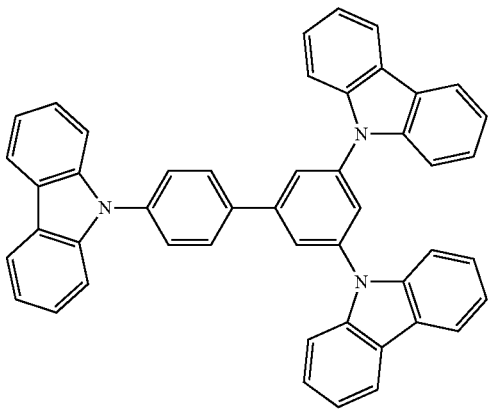
Host-9
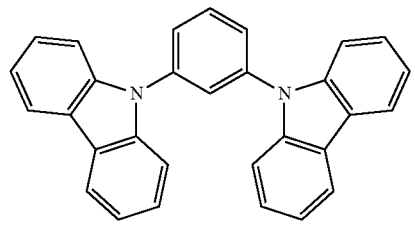
Host-10
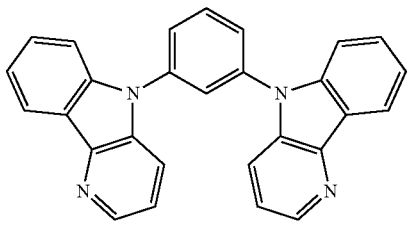

-continued
Host-11
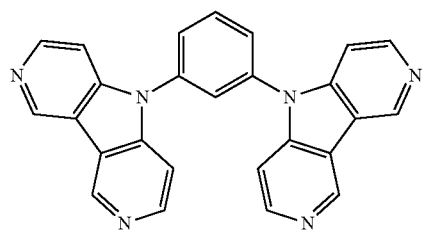
Host-12
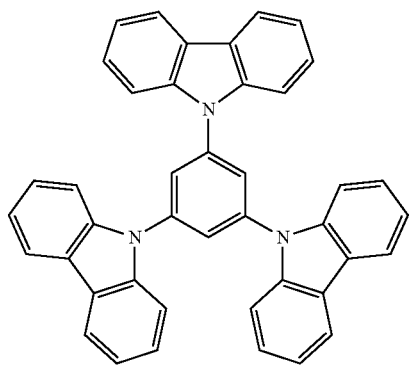
Host-13
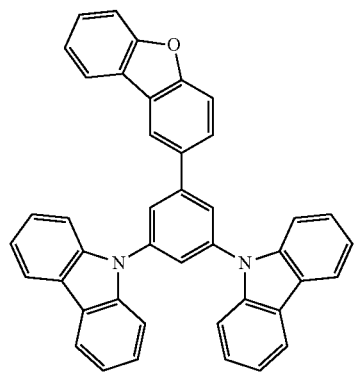
Host-14
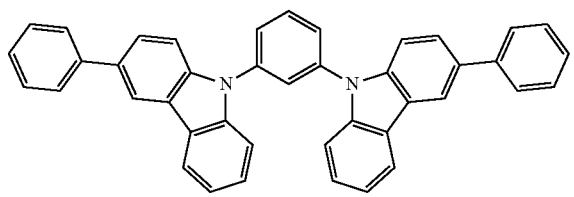
Host-15
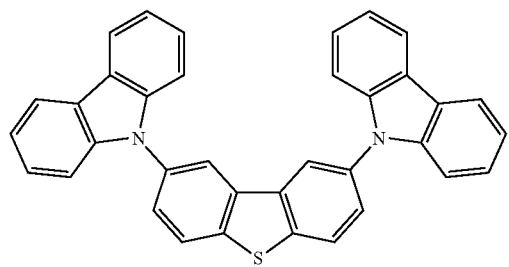
Host-16
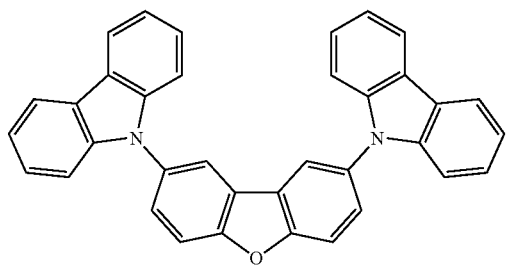
Host-17
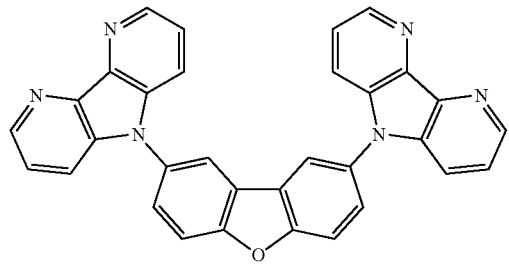
Host-18
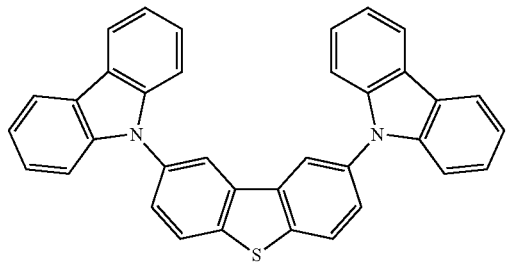

-continued
Host-19
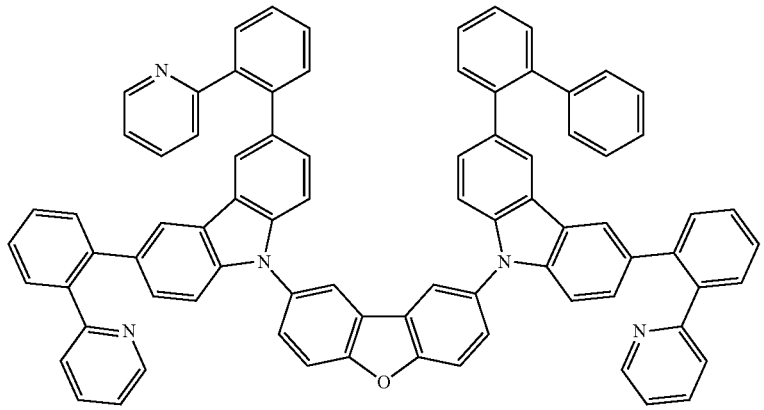
Host-20
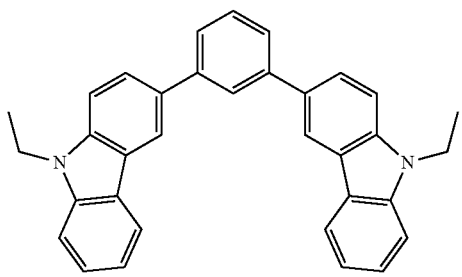
Host-21
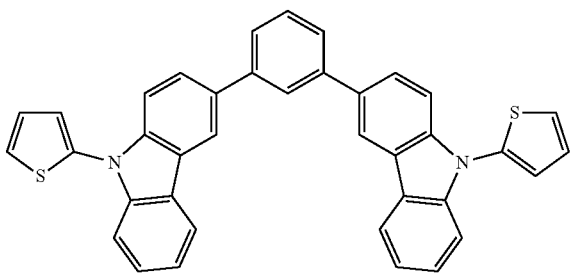
Host-22
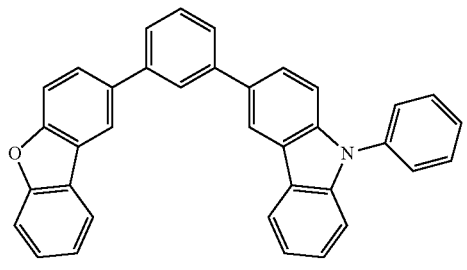
Host-23
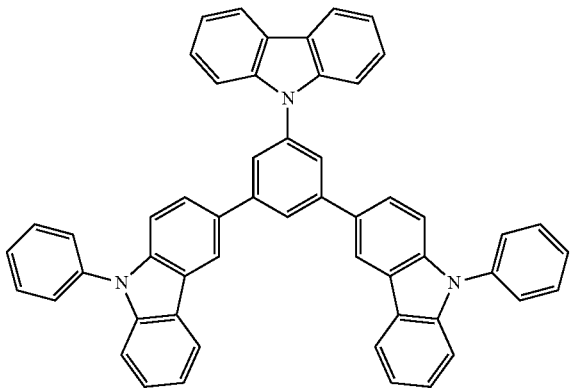
Host-24
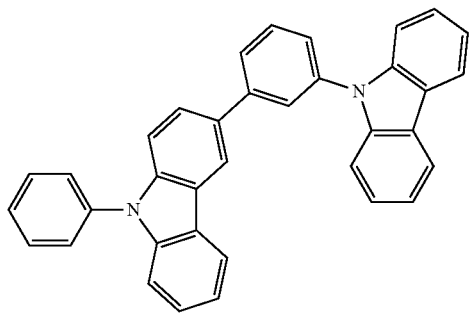
Host-25
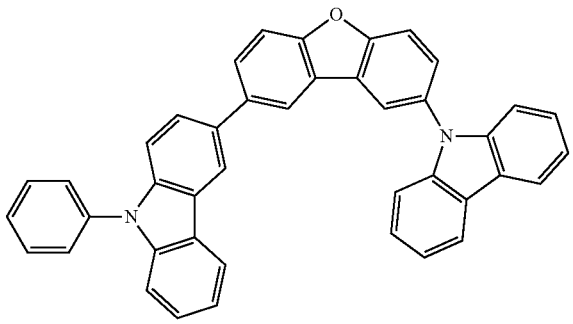

-continued
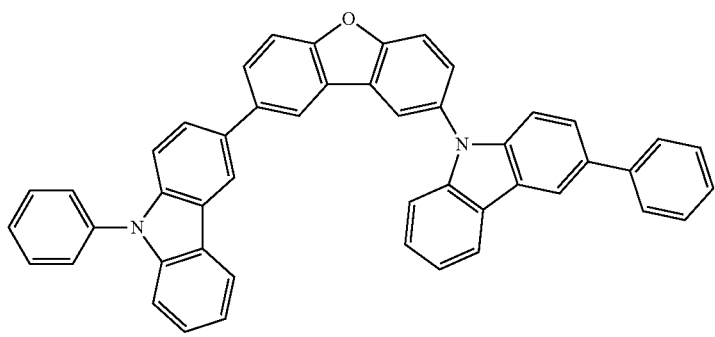
Host-26
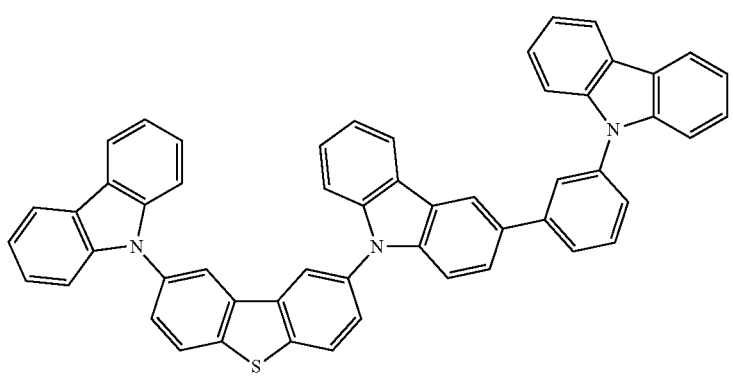
Host-27
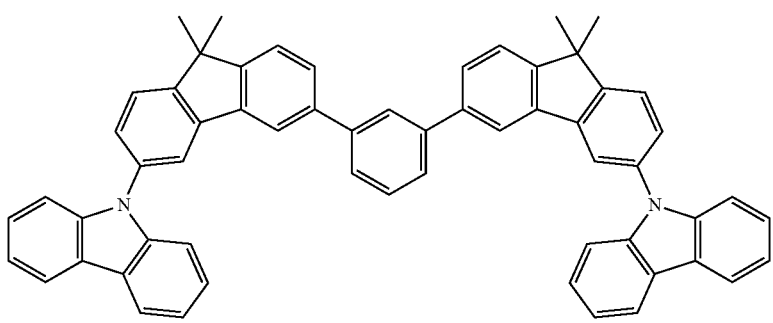
Host-28
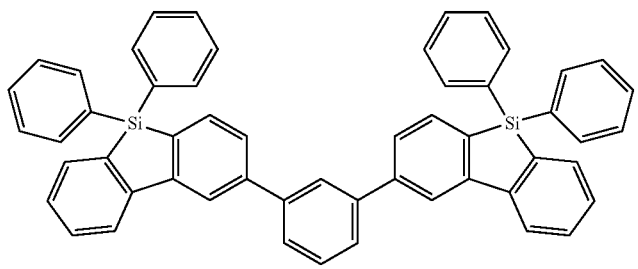
Host-29
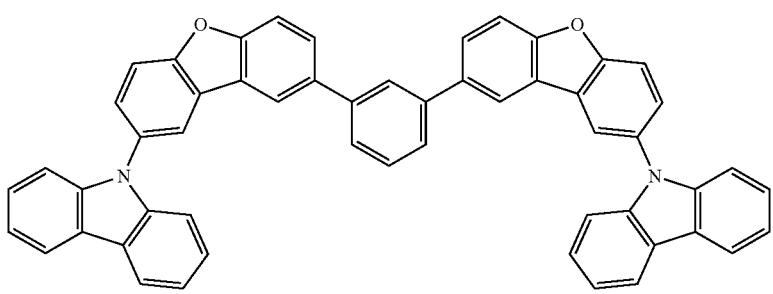
Host-30

Host-31
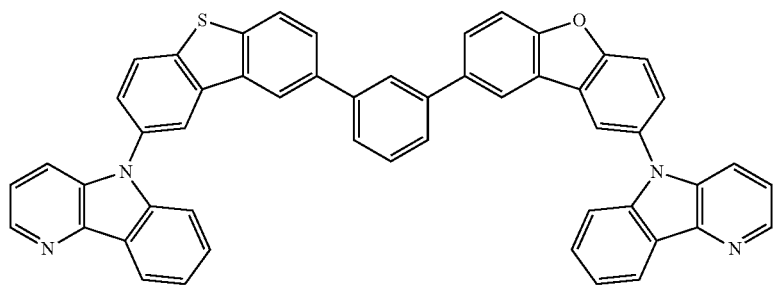
Host-32
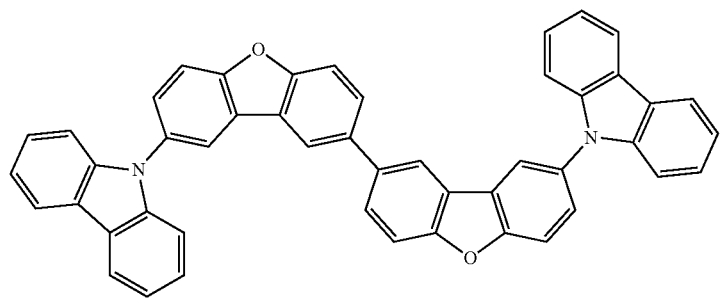
Host-33
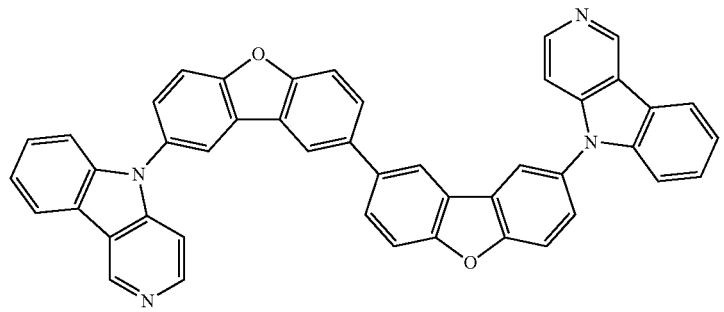
Host-34
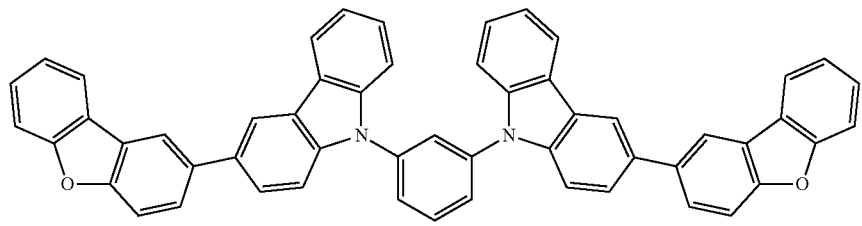
Host-35
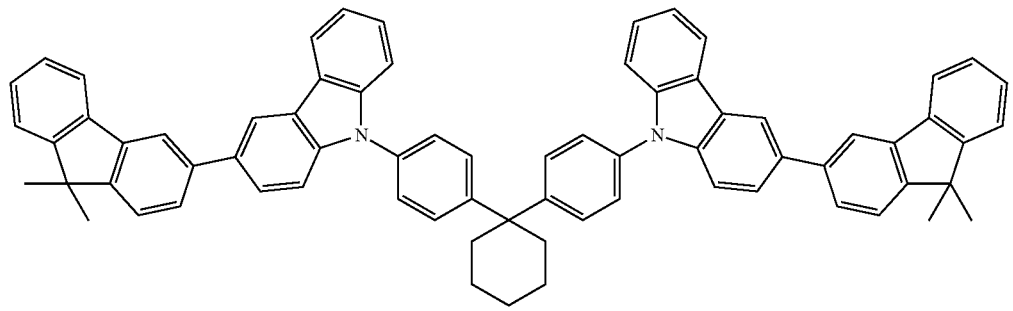

-continued
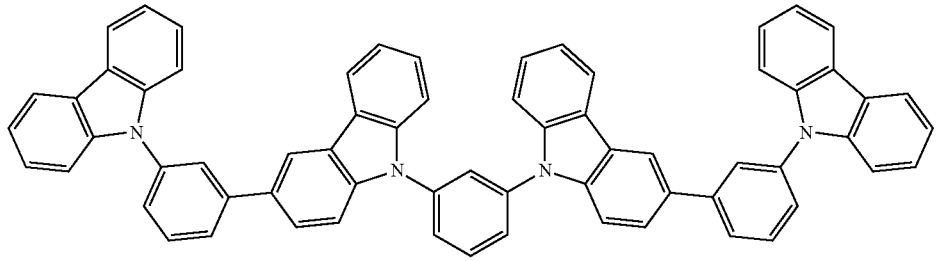
Host-36
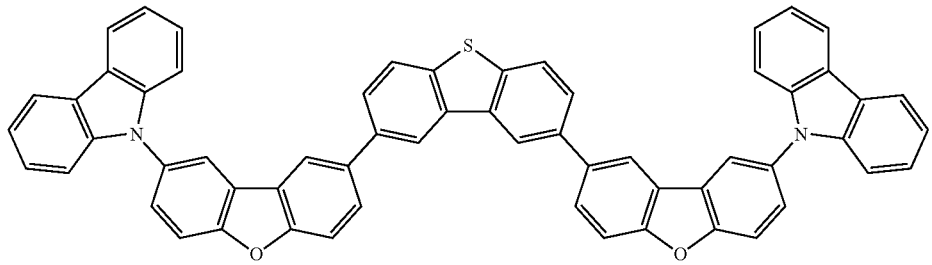
Host-37
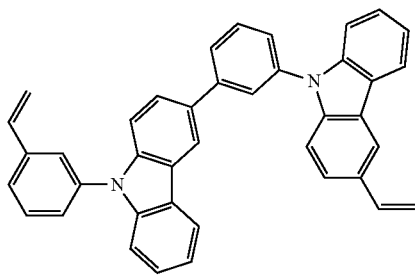
Host-38
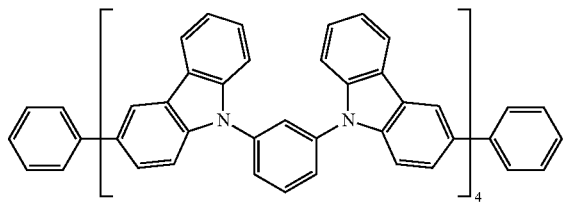
Host-39
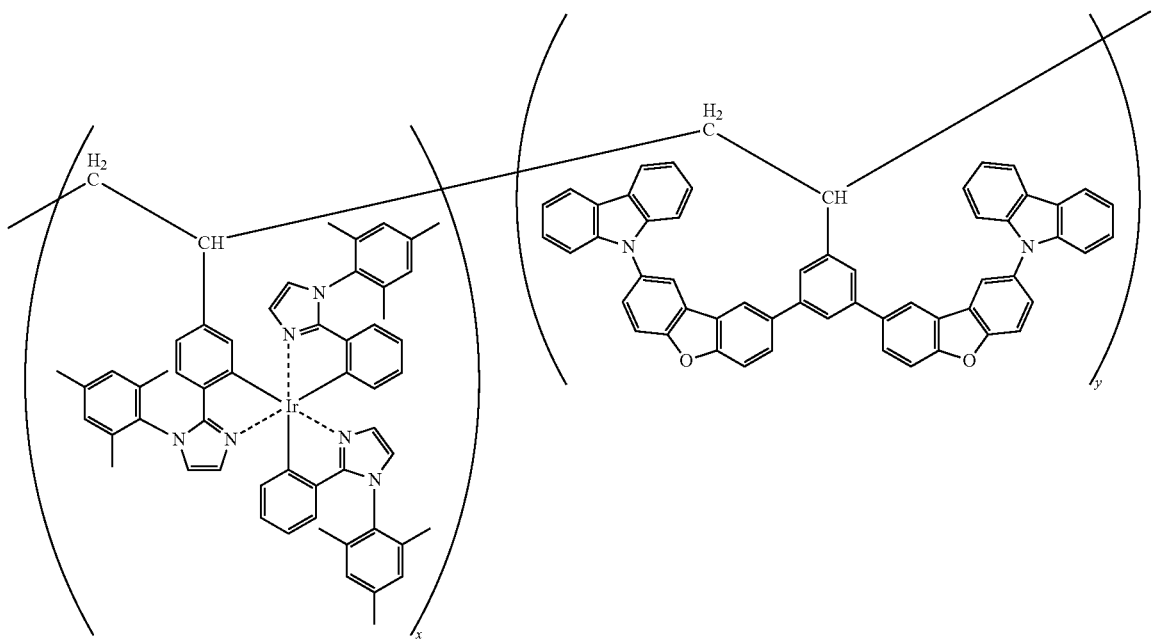
Host-40
x:y = 1:10
random co-polymer Host-41
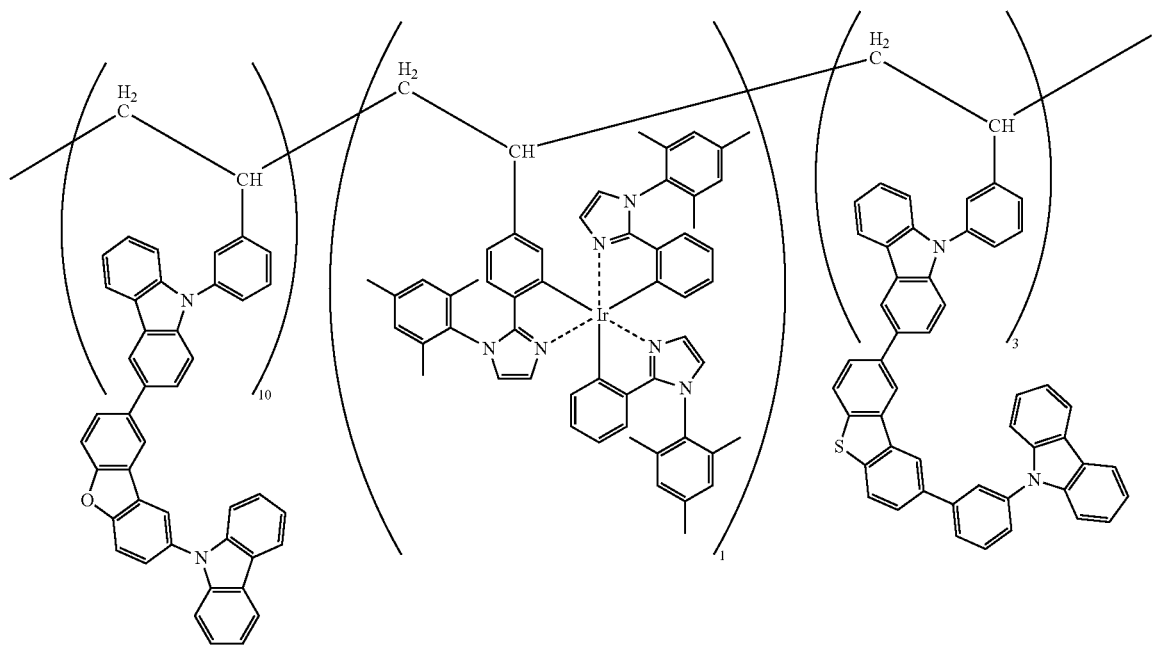
Host-42
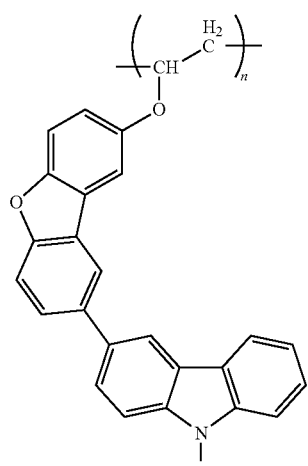

-continued
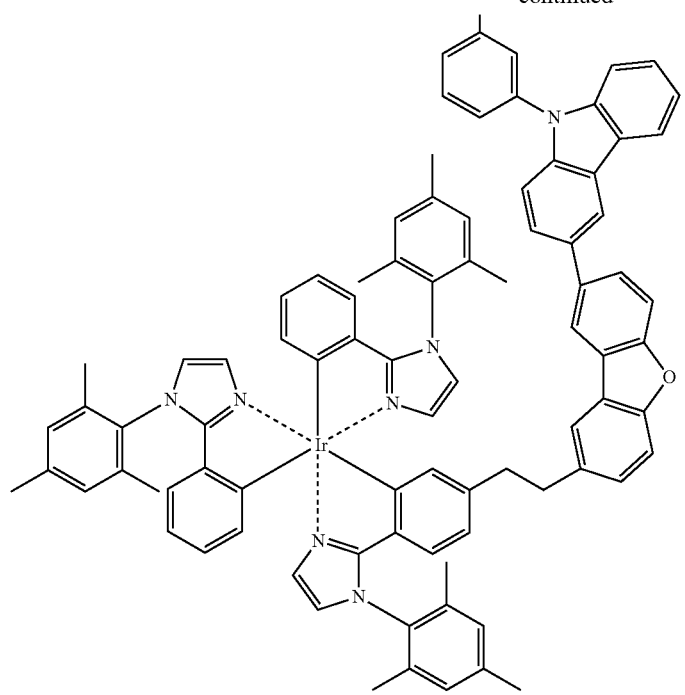
Mw(Weight Average Molecular Weight) = 40,000
Host-43
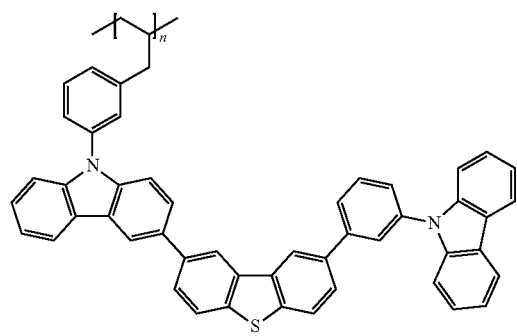
Mw(Weight Average Molecular Weight) = 100,000
Host-44
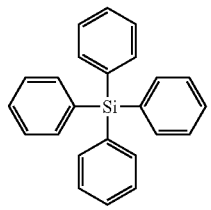
Host-45
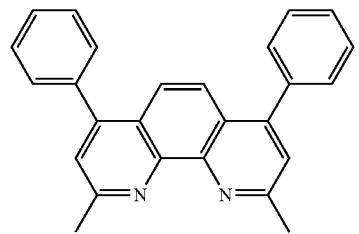
Host-46
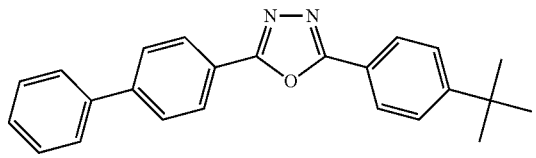

-continued
Host-47
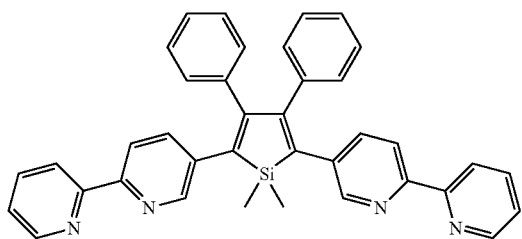
Host-48
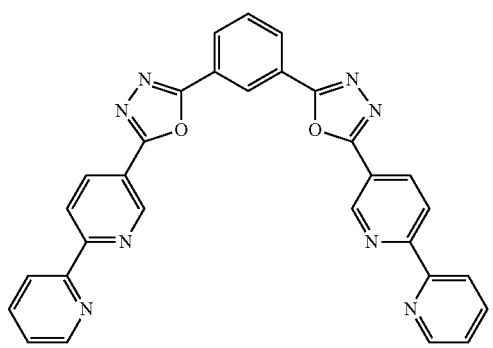
Host-49
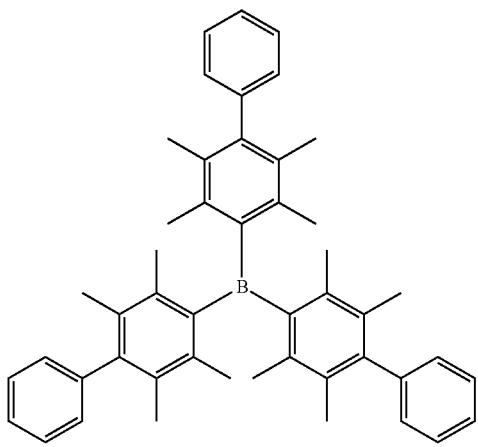
Host-50
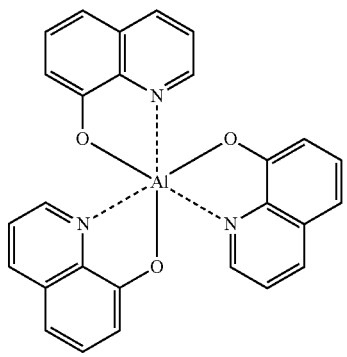
Host-51
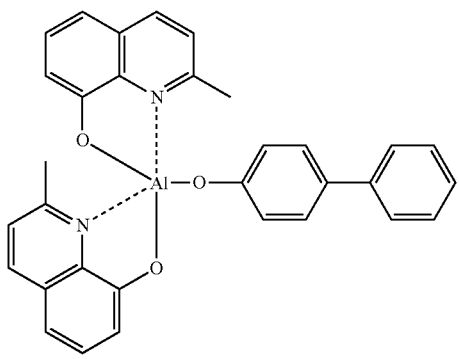
Host-52
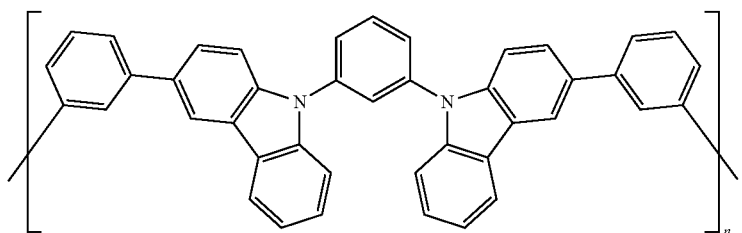
n = 100

Host-53

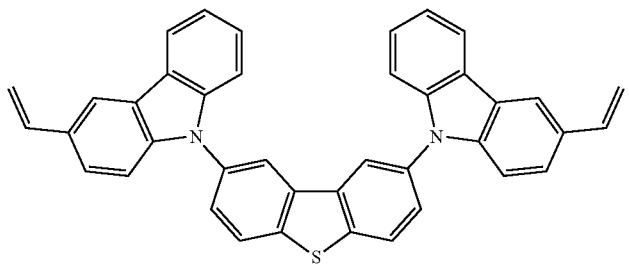

An especially preferable light emitting host in a light emitting layer of an organic El element of the present invention is a compound represented by the following Formula (6).

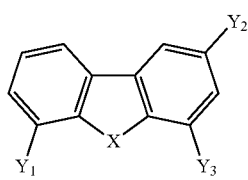

Formula (6)

In the formula, X represents O or S. $Y_1$ to $Y_3$ represent a hydrogen atom, a substituent, or a group represented by Formula (D), provided that at least one of $Y_1$ to $Y_3$ is represented, by Formula (D), and that at least one of the groups represented by Formula (D) has Ar of a carbazolyl group.

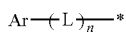

Formula (D)

In the formula, L represents a divalent linking group derived from an aromatic hydrocarbon ring or an aromatic heterocycle. n represents an integer of 0 or 1 to 3. When n is 2 or more, a plurality of Ls may be the same or different. "*" indicates a bonding portion to Formula (1). Ar represents a group represented by the following Formula (E).

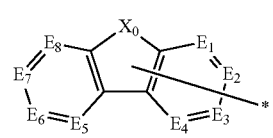

Formula (E)

In the formula, $X_0$ represents N(R), O or S. $E_1$ to $E_8$ represent $C(R_1)$ or N. R and $R_1$ represent a hydrogen atom, a substituent or a bonding portion to L. "*" indicates a bonding portion to L.

In a compound represented by Formula (6), at least two of $Y_1$ to $Y_3$ are preferably represented by Formula (D). More preferably, $Y_1$ is represented by Formula (D), and Ar in Formula (D) represents a carbazolyl group which may have a substituent. Still more preferably, $Y_1$ is represented by Formula (D), and Ar in Formula (D) represents a carbazolyl group bonded to L at an N position, provided that the carbazolyl group may have a substituent.

Further, $Y_2$ is preferably represented by Formula (D), and $Y_2$ preferably represents a hydrogen atom.

Hereafter, there are shown specific examples of a host compound represented by Formula (6) (it is also called as an emission hoist) preferably used in a light emitting layer of an organic EL element of the present invention. The present invention will not be limited to these.

1

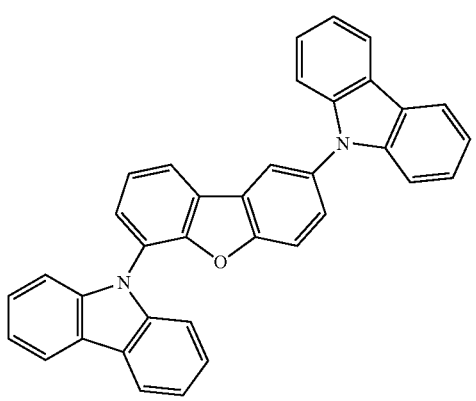

2

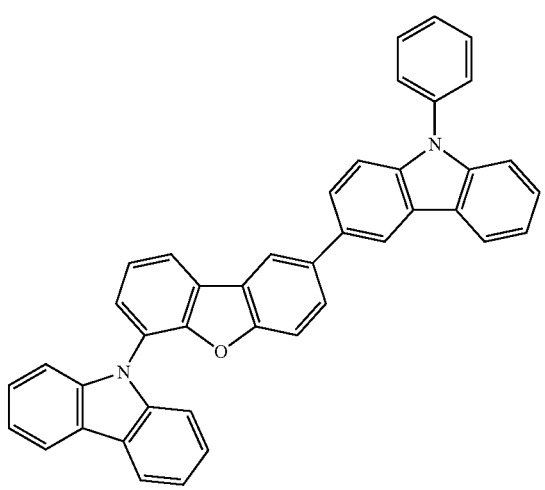

-continued
3
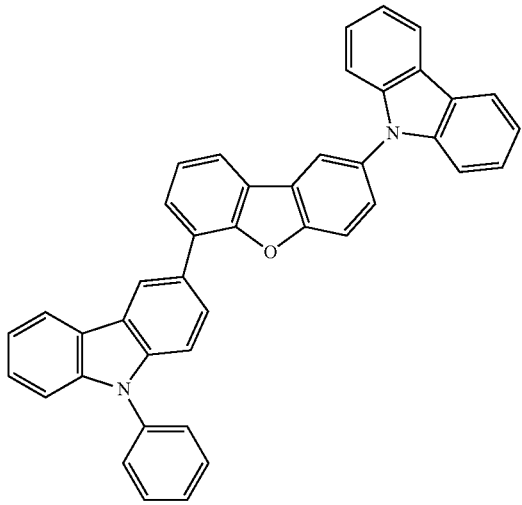
4
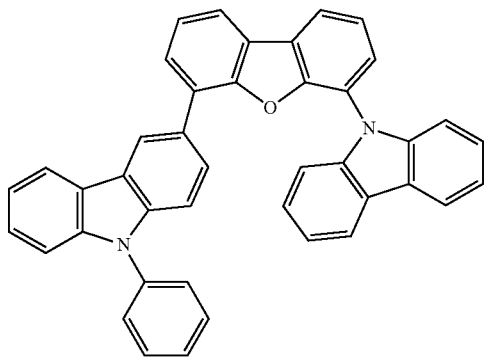
5
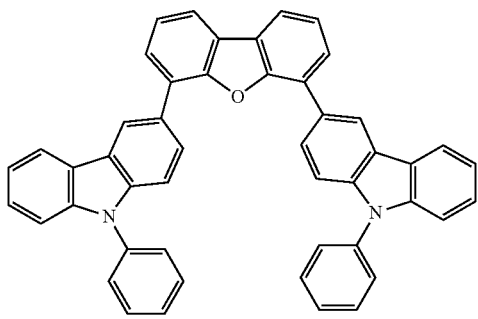
6
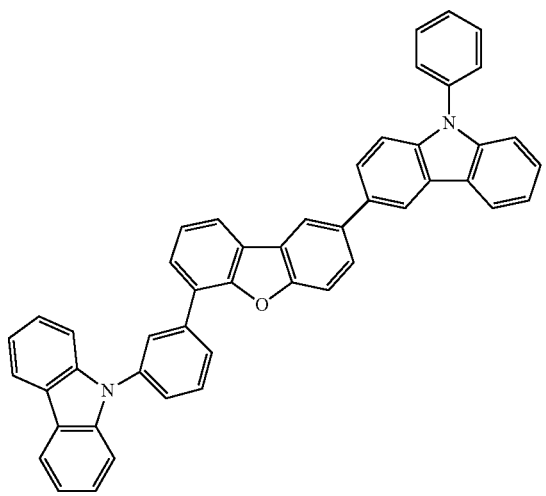
7
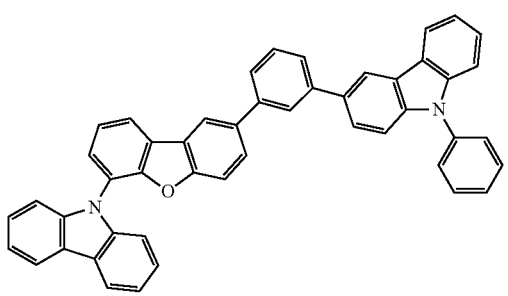
8
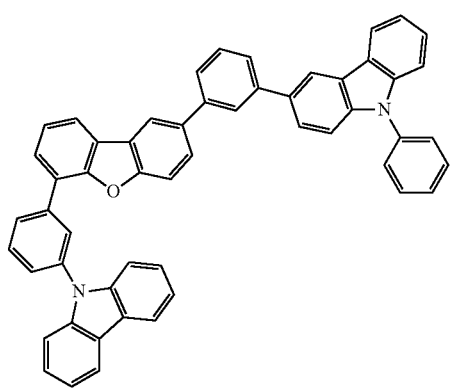

-continued
9
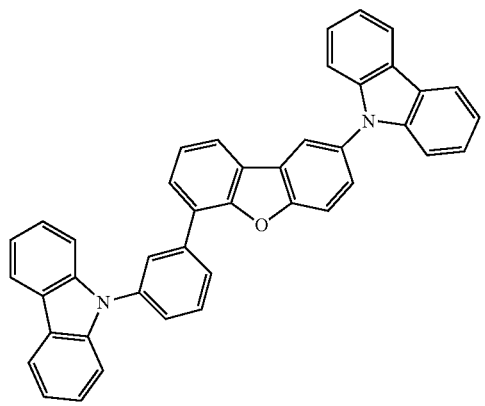
10
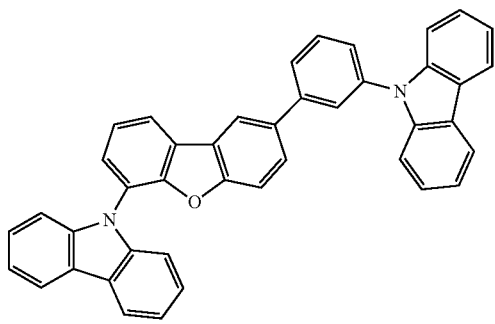
11
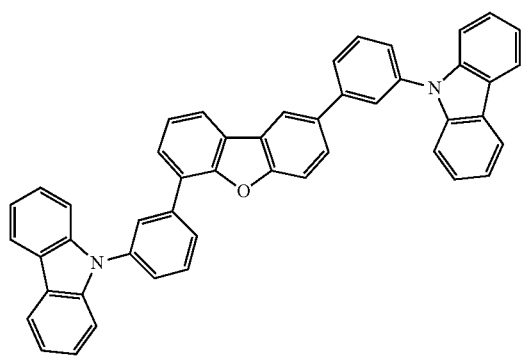
12
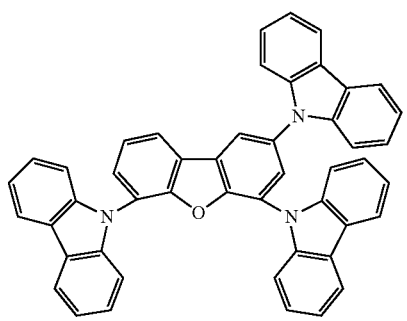
13
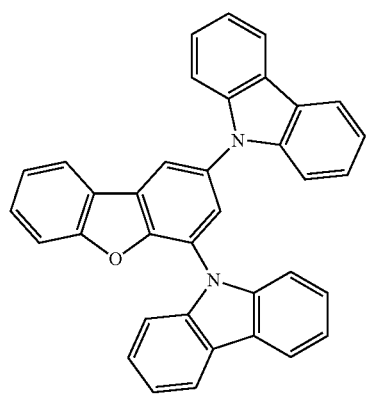
14
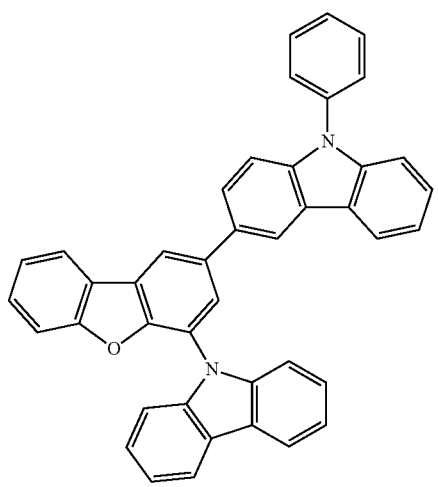

-continued
15
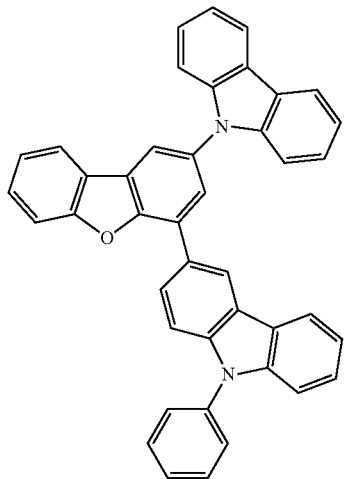
16
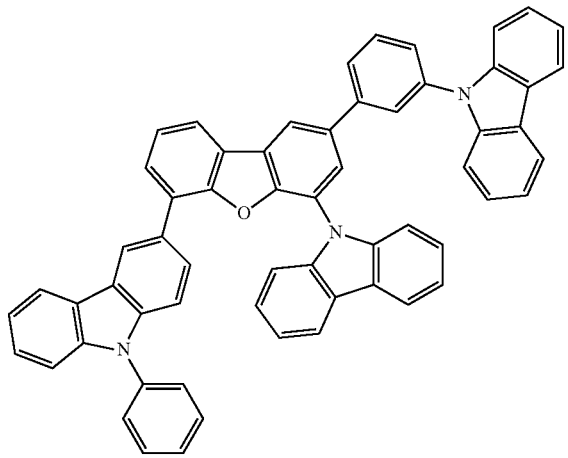
17
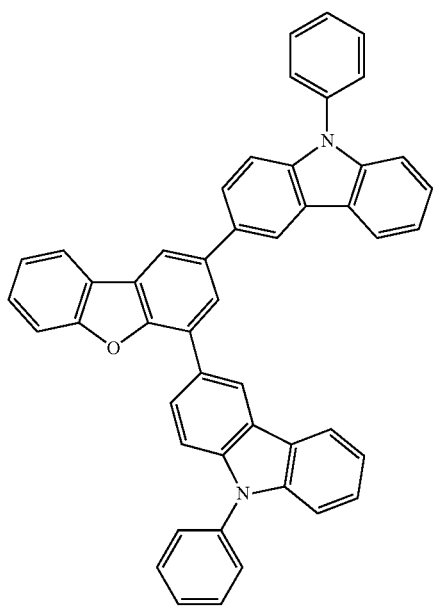
18
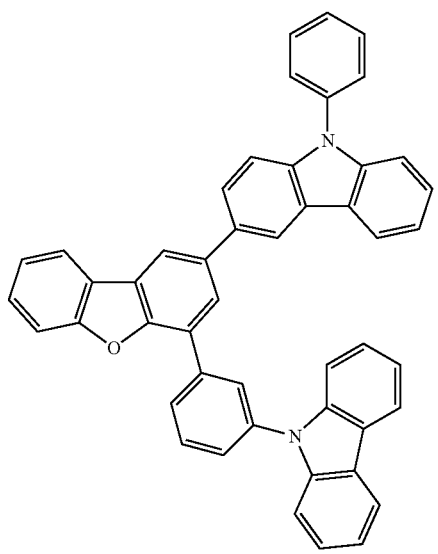
19
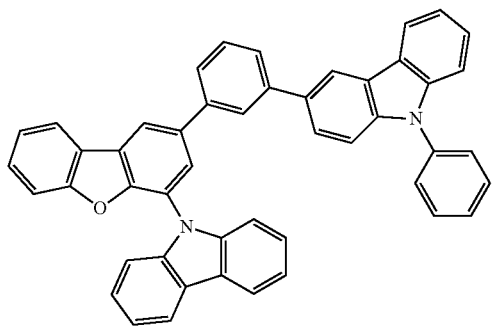
20
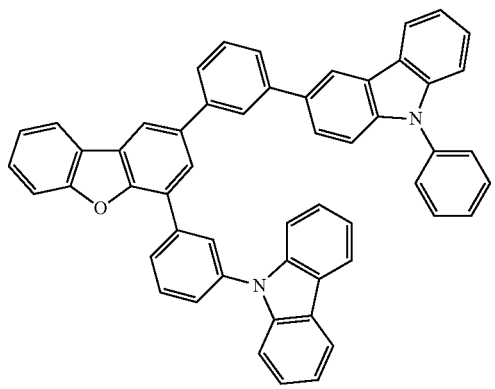

-continued
21
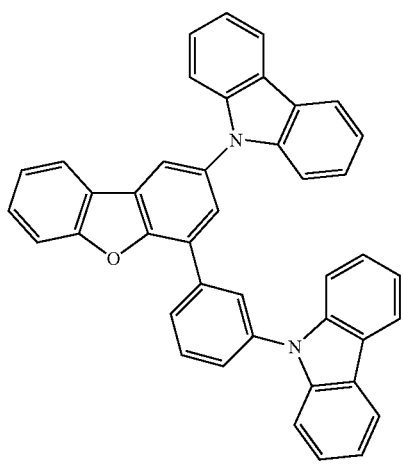
22
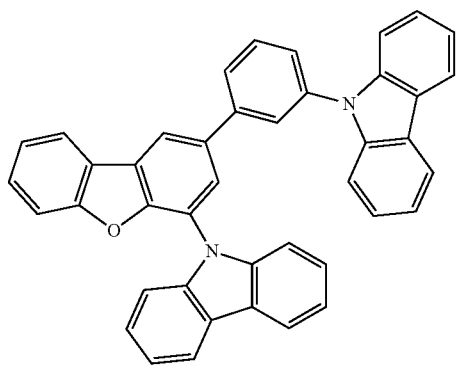
23
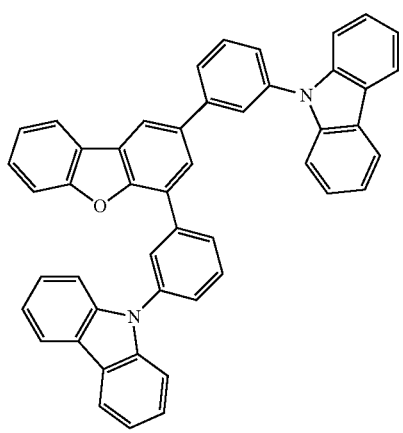
24
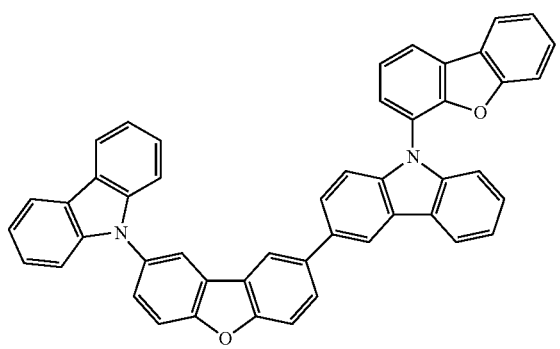
25
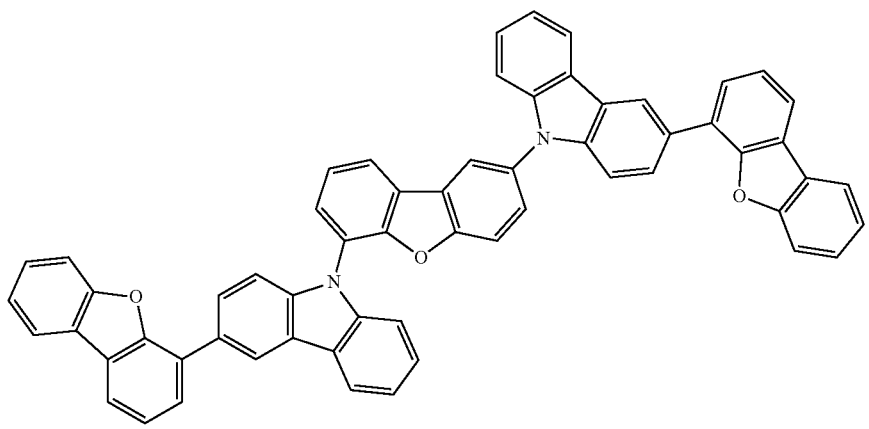

26
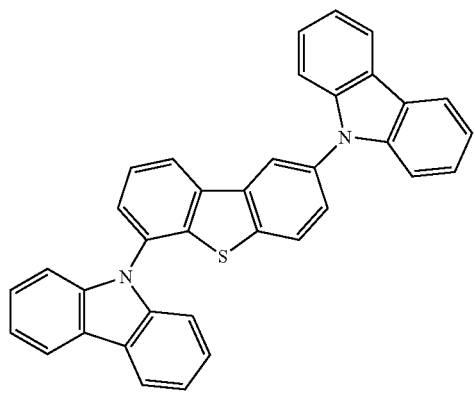
27
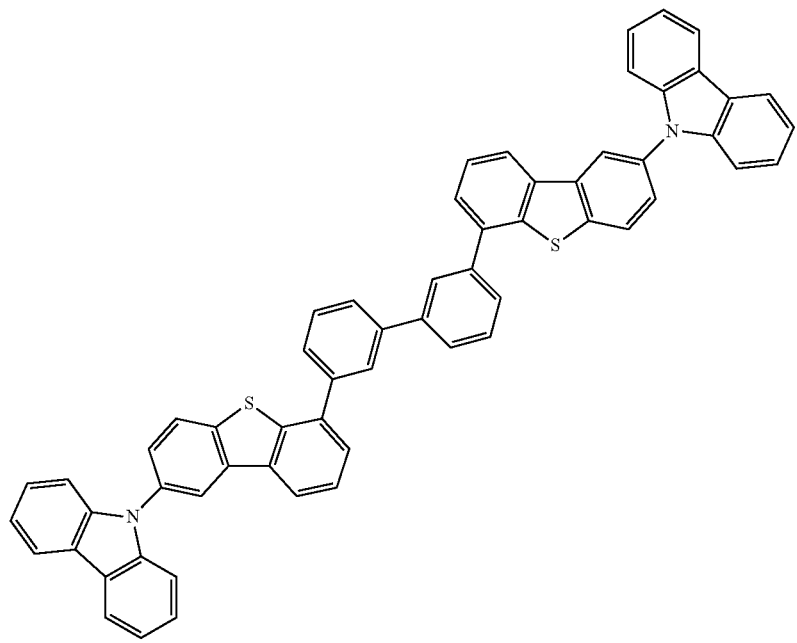
28
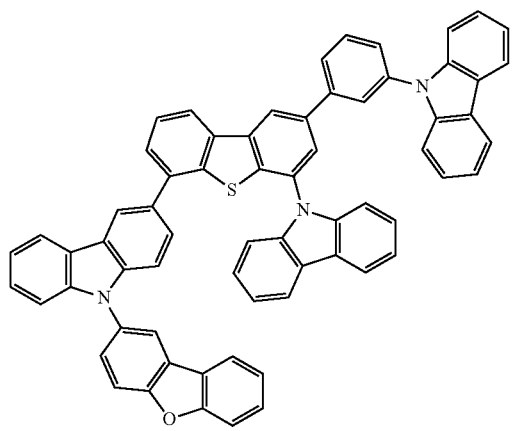
29
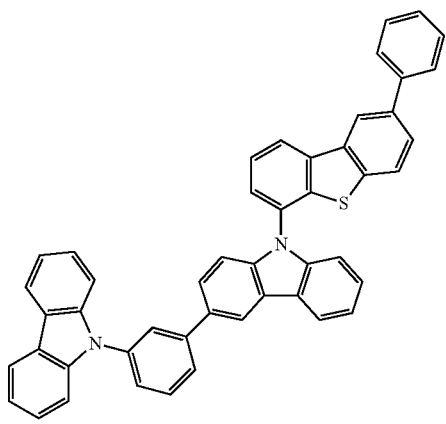

-continued
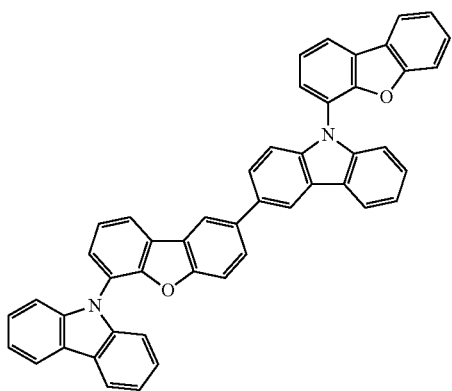
30
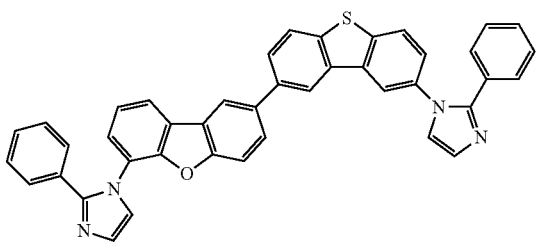
31
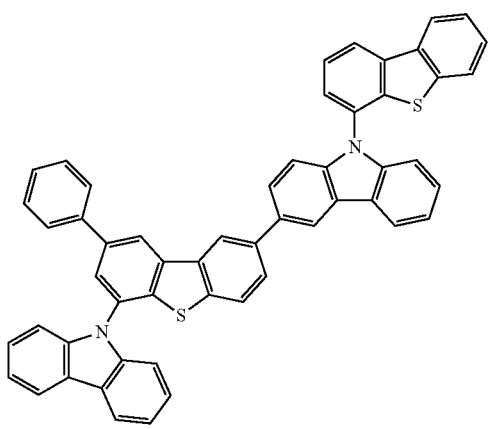
32
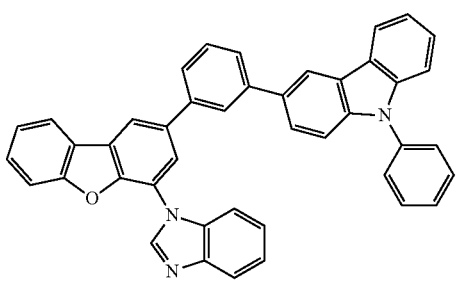
33
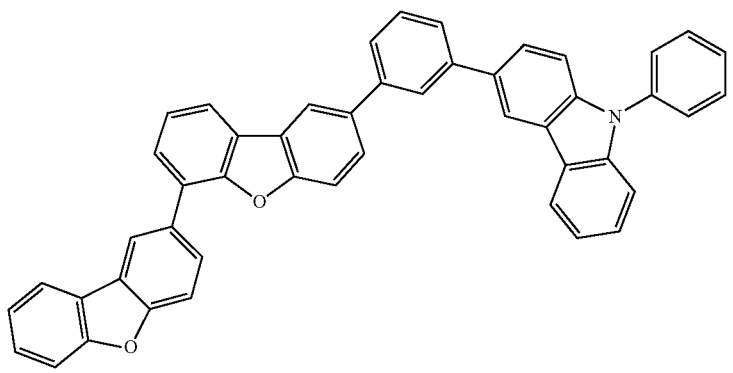
34

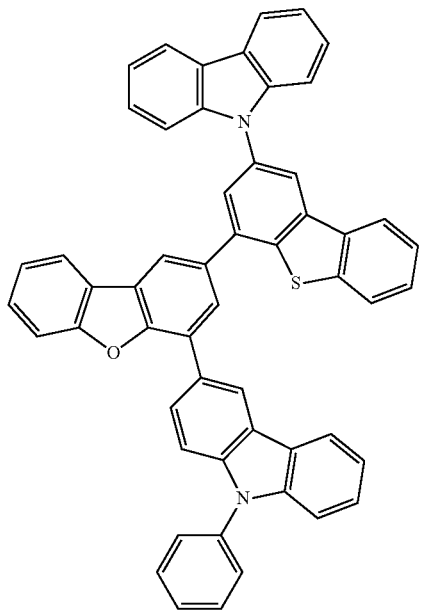
35
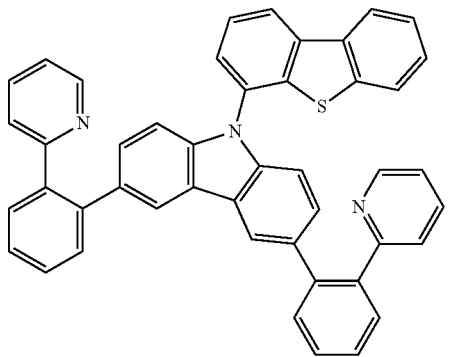
36
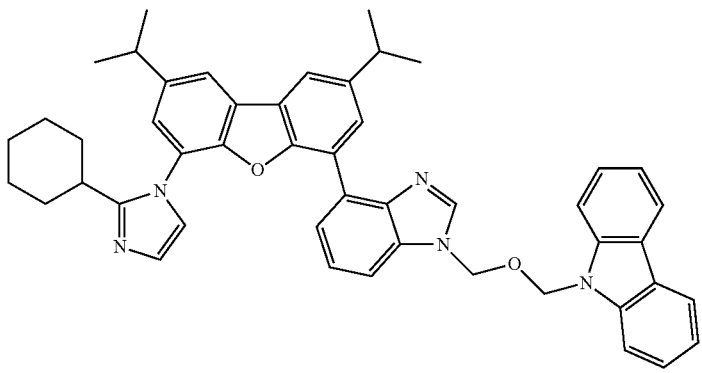
37
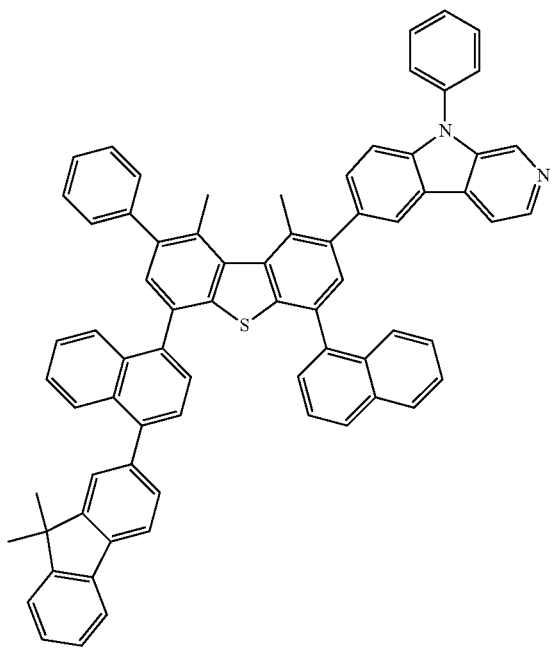
38

39
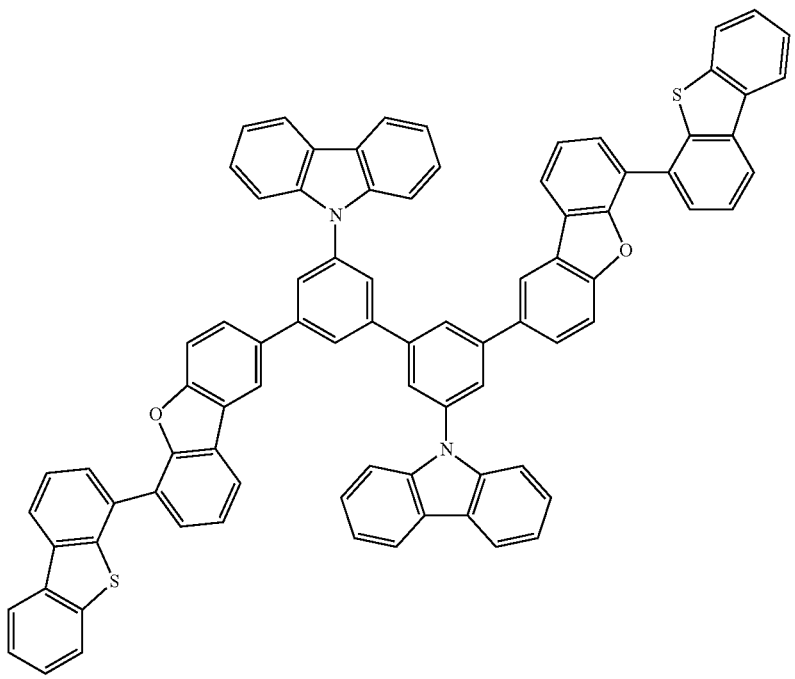
40
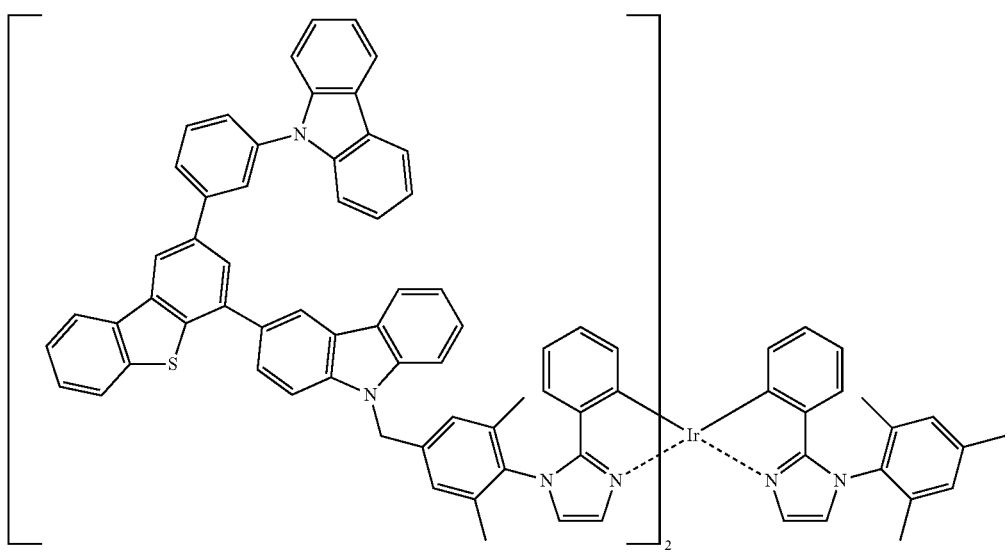

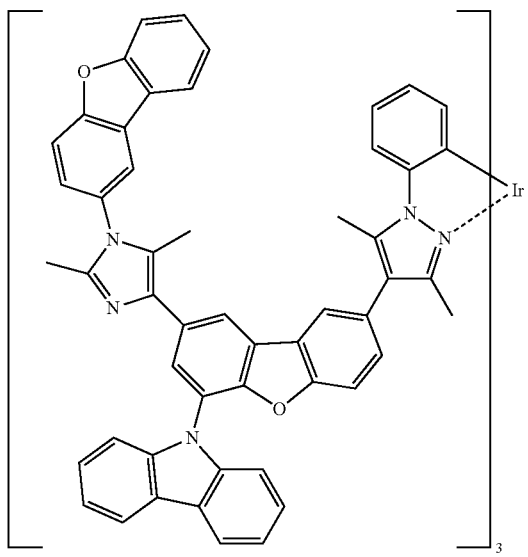
41
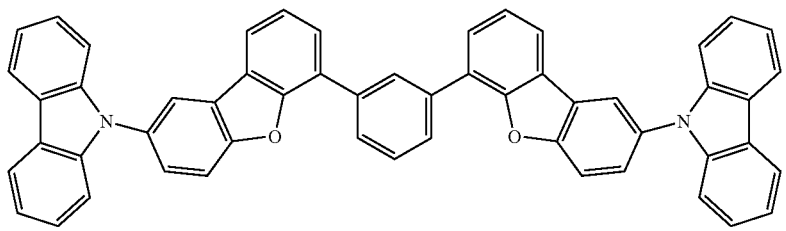
42
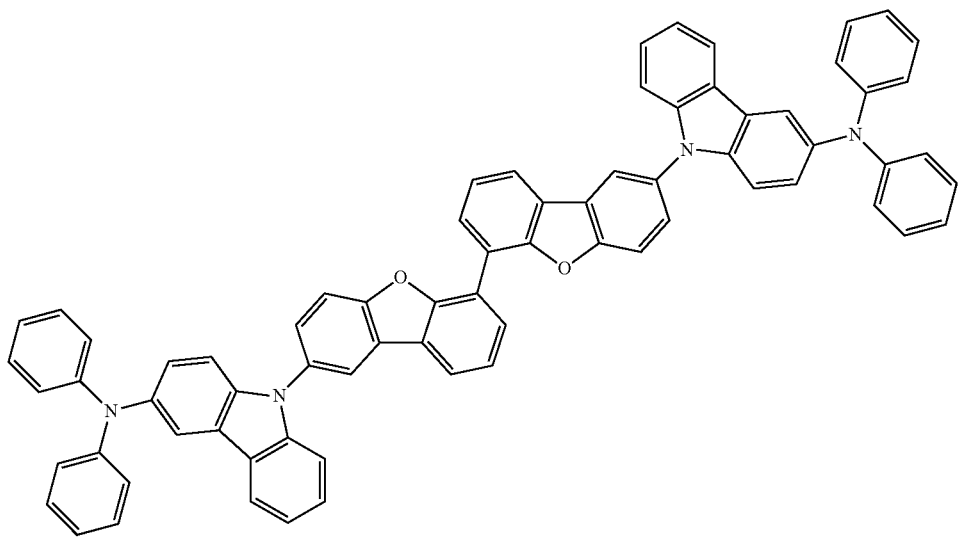
43

44
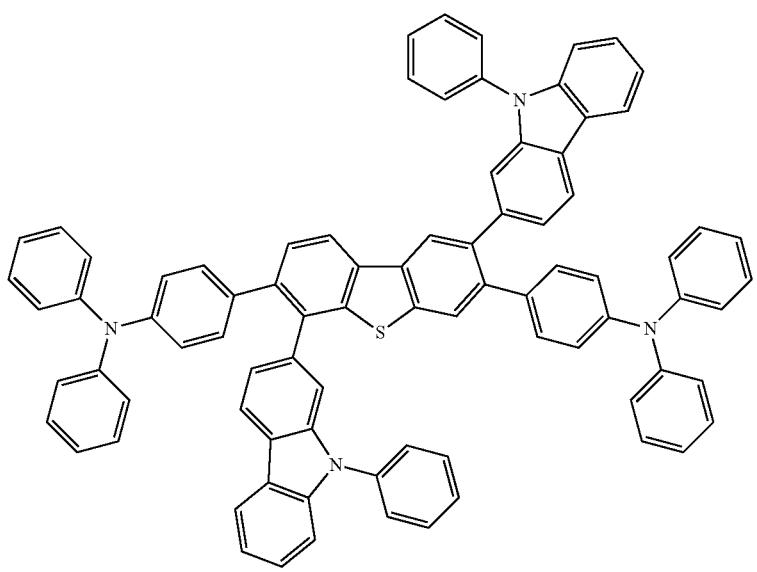
45
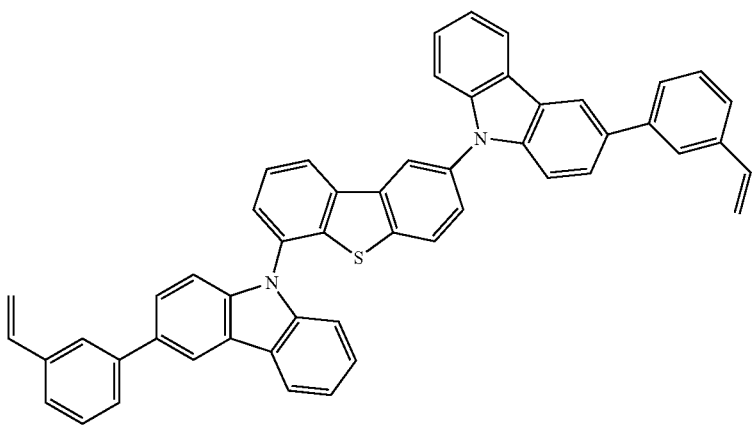
46
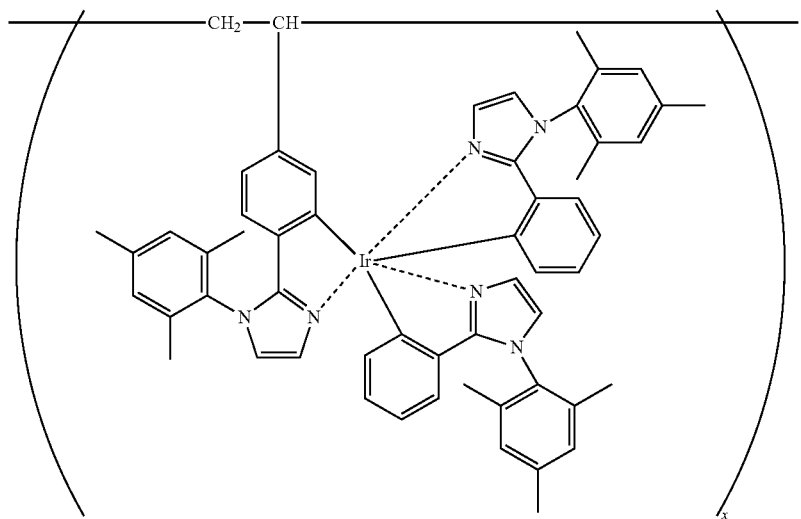

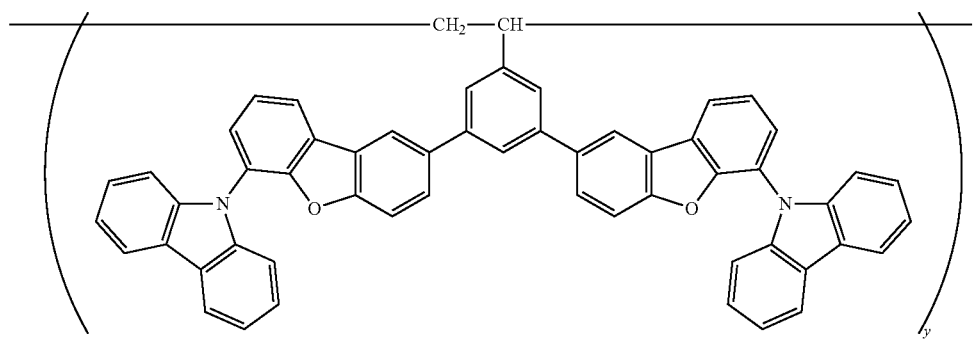
x:y = 1:10
random co-polymer
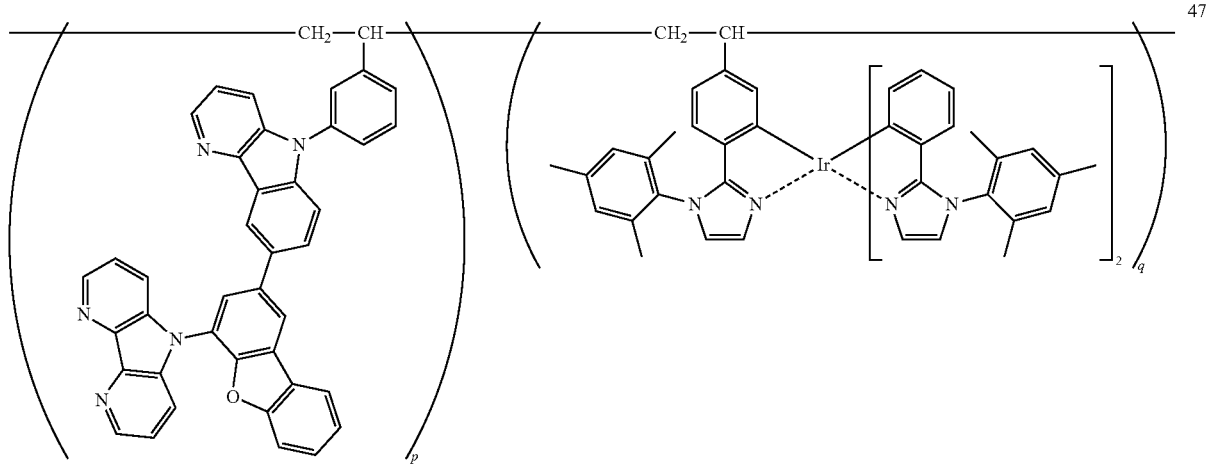
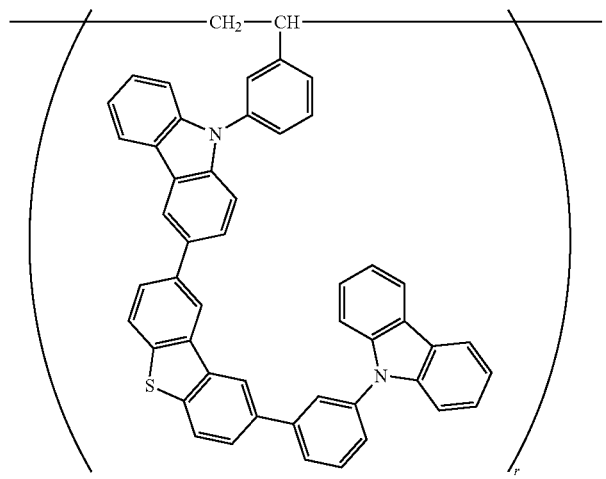

-continued
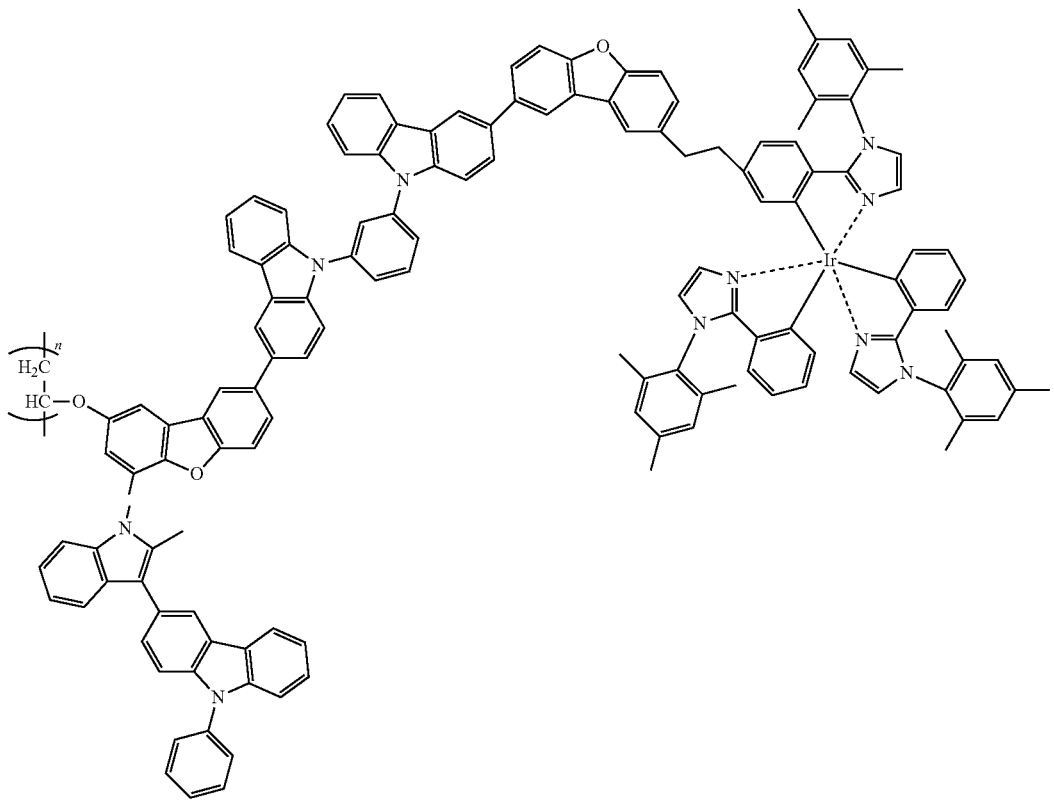
48
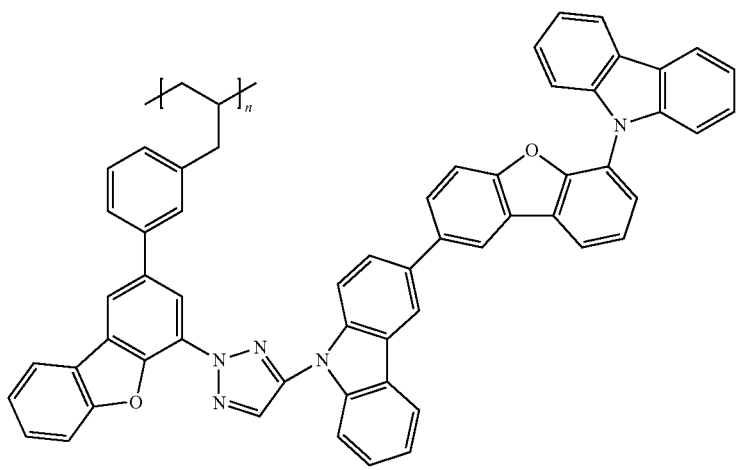
49
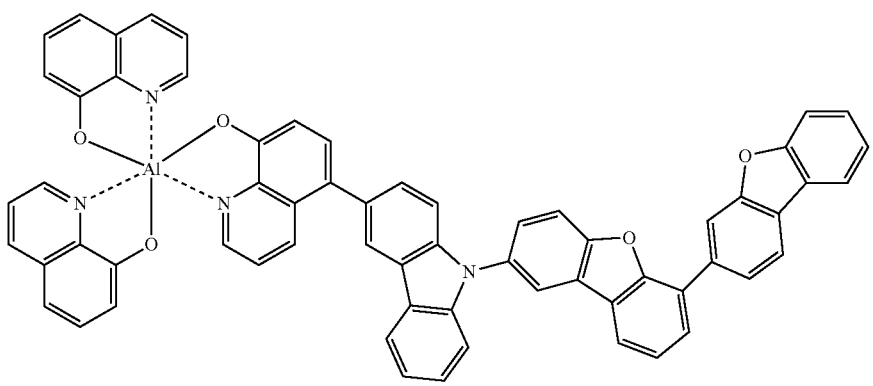
50

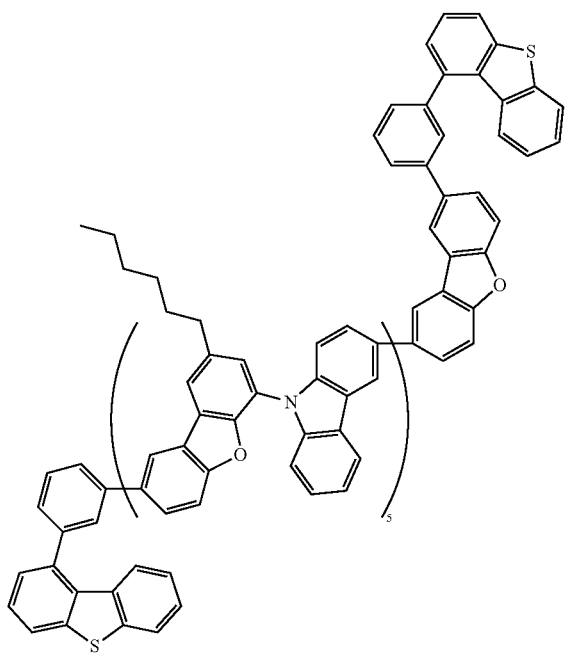
51
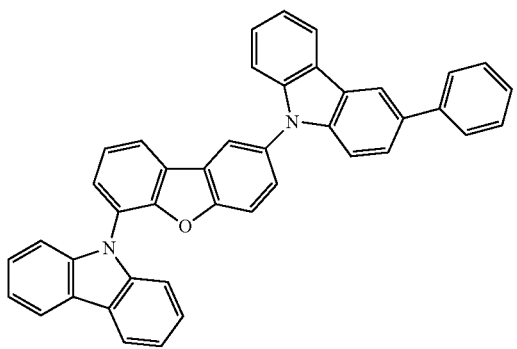
52
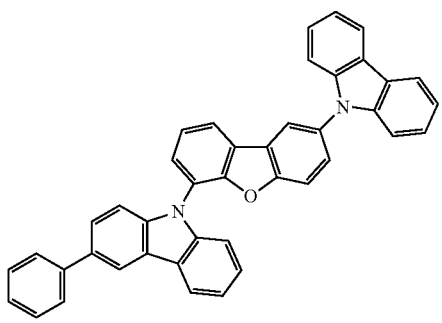
53
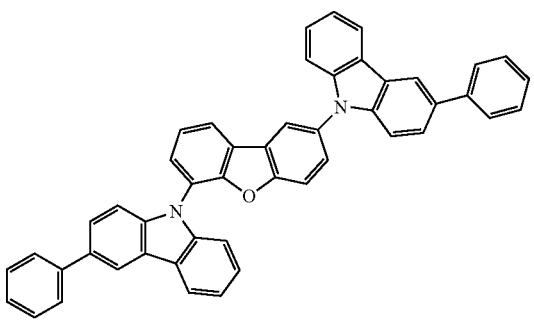
54

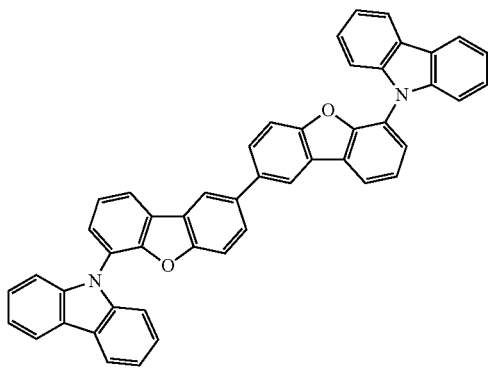

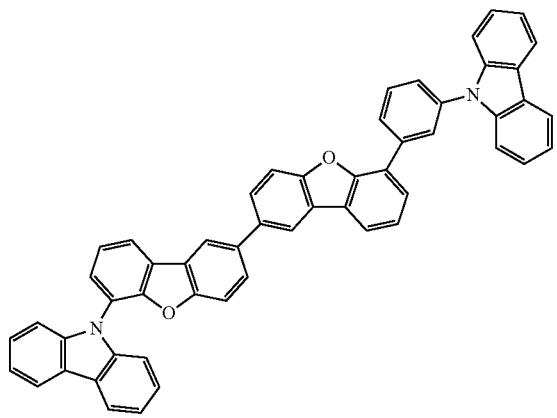

<<Hole Transport Layer>>

A hole transport layer contains a material having a function of transporting a hole, and in a broad meaning, a hole injection layer and an electron blocking layer are also included in a hole transport layer. A single layer of or plural layers of a hole transport layer may be provided.

A hole transport material is a material having any one of a property to inject or transport a hole or a barrier property to an electron, and it may he either an organic substance or an inorganic substance.

For example, listed materials are a triazole derivative, an oxadiazole derivative, an imidazole derivative, a polyarylalkane derivative, a pyrazolone derivative, a phenylenediamine derivative, an arylamine derivative, an amino substituted chalcone derivative, an oxazole derivatives, a styrylanthracene derivative, a fluorenone derivative, a hydrazone derivative, a stilbene derivative, a silazane derivative, an aniline type copolymer, or conductive polymer oligomer and specifically preferably such as thiophene oligomer.

As a hole transport material, those described above can be utilized, however, it is preferable to utilized a porphyrin compound, an aromatic tertiary amine compound and a styrylamine compound, and specifically preferably an aromatic tertiary amine compound.

Typical examples of an aromatic tertiary amine compound and a styrylamine compound include: N,N,N',N'-tetraphenyl-4,4'-diaminophenyl; N,N'-diphenyl-N,N'-bis(3-methylphenyl)-(1,1'-biphenyl)-4,4'-diamine (TDP); 2,2-bis(4-di-p-tolylaminophenyl)propane; 1,1-bis(4-di-p-tolylaminophenyl)cyclohexane; N,N,N',N'-tetra-p-tolyl 4,4'-diaminobiphenyl; 1,1-bis(4-di-p-tolylaminophenyl)-4-phenylcyclohexane; bis(4-dimethylamino-2-metyl)phenylmethane; bis(4-di-p-tolylaminophenyl)phenylmethane; N,N'-diphenyl-N,N'-di(4-methoxyphenyl)-4,440-diaminobiphenyl; N,N,N',N'-tetraphenyl-4,4'-diaminophenylether; 4,4'-bis(diphenylamino)quadriphenyl; N,N,N-tri(p-tolyl)amine; 4-(di-p-tolylamino)-4'-[4-(di-p-triamino)styryl]stilbene; 4-N,N-diphenylamino-(2-diphenylvinyl)benzene; 3-methoxy-4'-N,N-diphenylaminostilbene; and N-phenylcarbazole, in addition to those having two condensed aromatic rings in the molecule described in U.S. Pat. No. 5,061,569, such as 4,4'-bis[N-(1-naphthyl)-N-phenylamino]biphenyl(NDP), and 4,4',4"-tris[N-(3-methylphenyl)-N-phenylamino]triphenylamine (MDTDATA), in which three of triphenyl amine units are bonded in a star burst form, described in JP-A No. 4-308688.

Polymer materials, in which these materials are introduced in a polymer chain or constitute the main chain of polymer, can be also utilized.

Further, an inorganic compound such as a p type-Si and a p type-SiC can he utilized as a hole injection material and a hole transport material.

Further, it is possible to employ so-called p type hole transport materials, as described in Japanese Patent Publication Open to Public inspection (referred to as JP-A) No. 11-251067, and J. Huang et al. reference (Applied Physics Letters 80(2002), p. 139). In the present invention, since high efficiency light emitting elements are prepared, it is preferable to employ these materials.

This hole transport layer can be prepared by forming a thin layer made of trie above-described hole transport material according to a method well known in the art such as a vacuum evaporation method, a spin coating method, a cast method, an inkjet method and a LB method.

The layer thickness of a hole transport layer is not specifically limited, however, it is generally 5 nm-5 μm, and preferably 5 nm-200 nm. This positive transport layer may have a single layer structure comprised of one or not less than two types of the above described materials.

Further, it is possible to employ a hole transport layer of a higher p property which is doped with impurities. As its example, listed are those described in each of JP-A Nos. 4-297076, 2000-196140, 2001-102175, as well as in J. Appl. Phys., 95,5773 (2004).

In the present invention, it is preferable to employ a bole transport layer of such a high p property, since it is possible to produce an element of lower electric power consumption.

There are given examples of the compound preferably used for formation of the hole transport layer of the organic EL element of the present invention. However, the present invention is not limited to these.

HT-1(TPD)
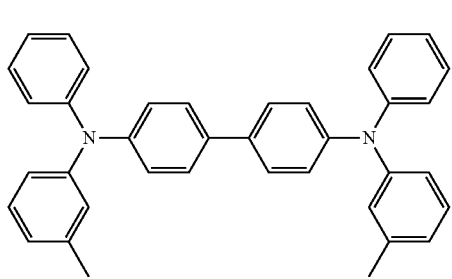
HT-2(α-NPD)
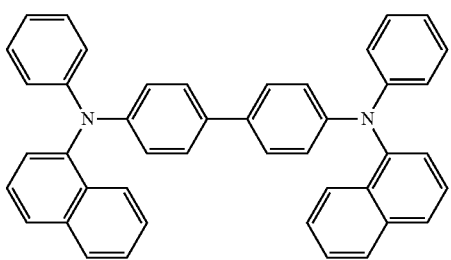
HT-3
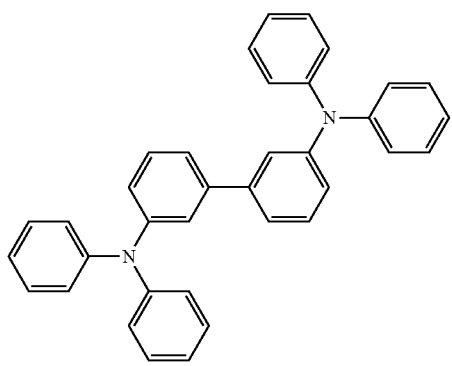
HT-4
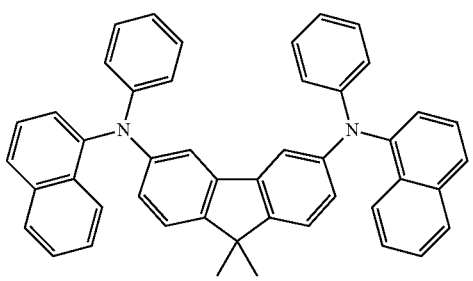
HT-5
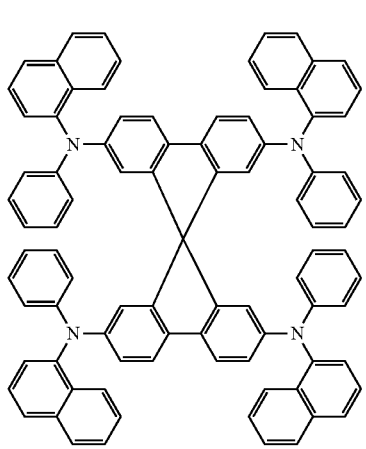
HT-6
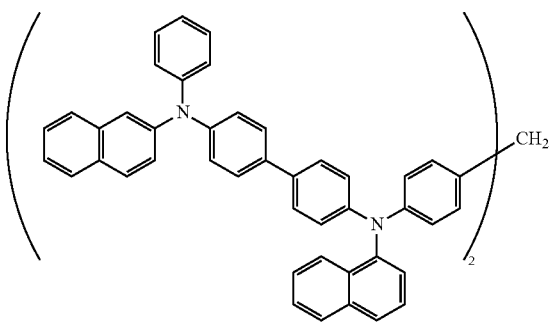
HT-7
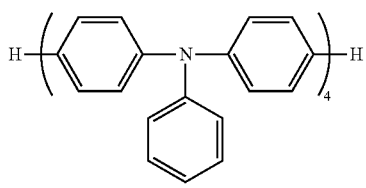
HT-8
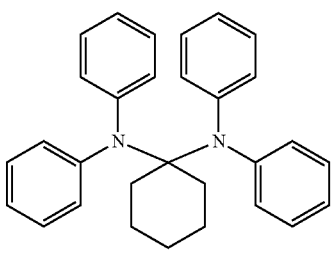

-continued
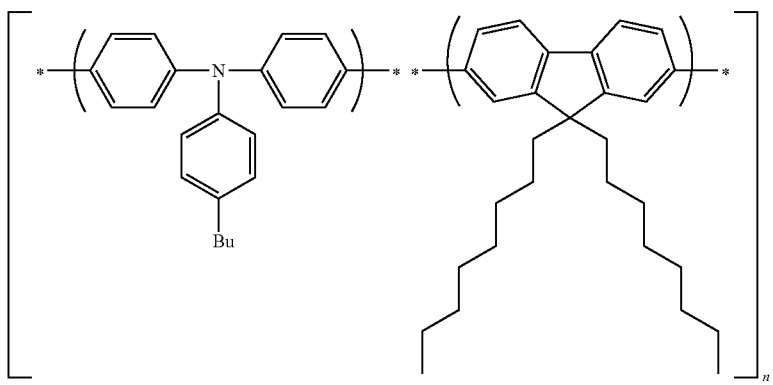
HT-9(F8-TFB)
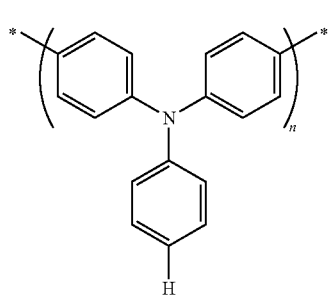
HT-10
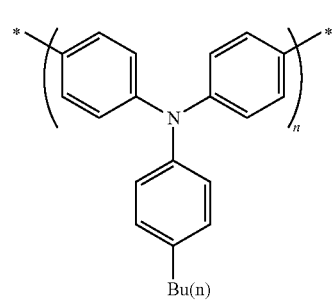
HT-11
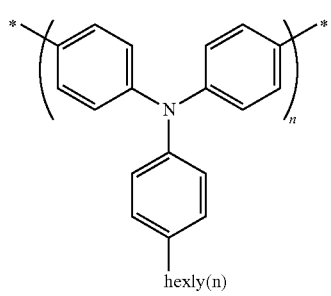
HT-12
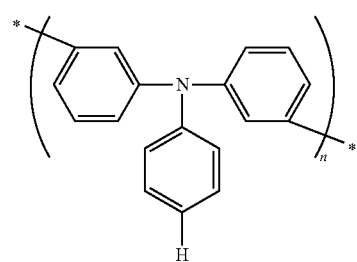
HT-13
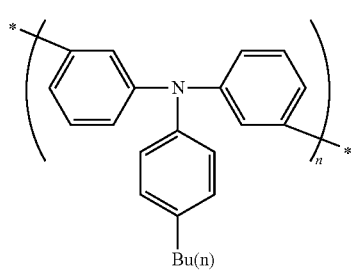
HT-14
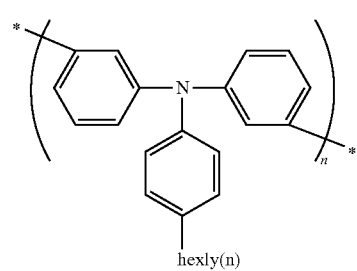
HT-15
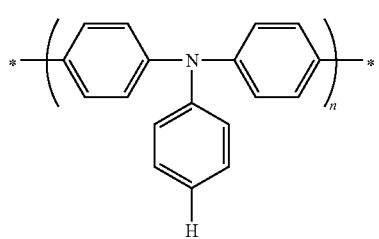
HT-16
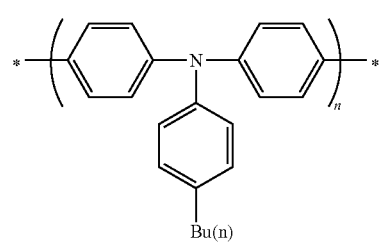
HT-17

HT-18
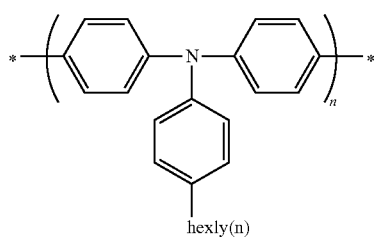

HT-19
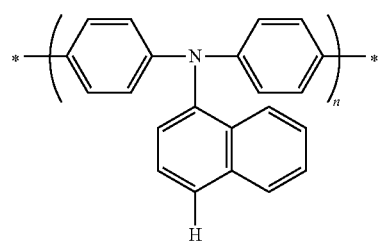

HT-20
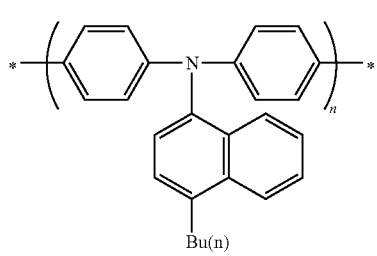

HT-21
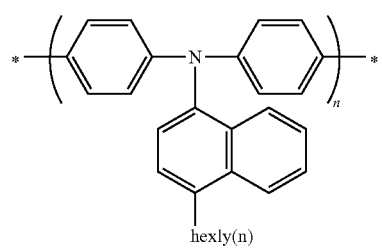

HT-22
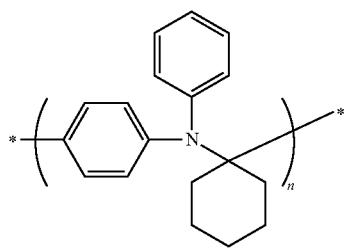

HT-23
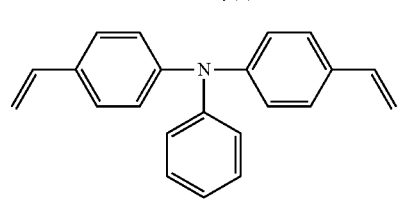

HT-24
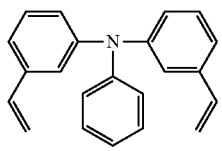

HT-25
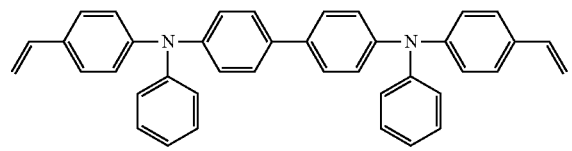

HT-26
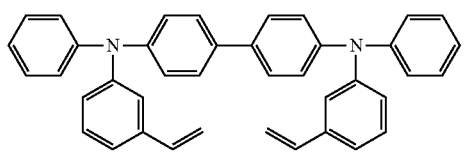

HT-27
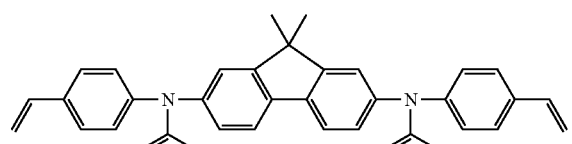

HT-28
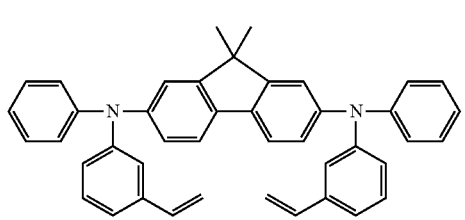

HT-29
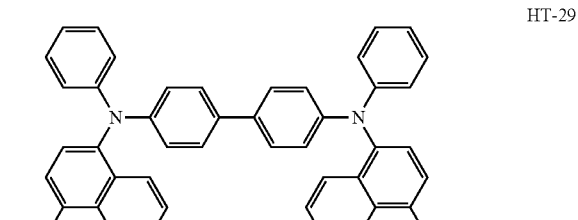

<<Blocking Layer: Hole Blocking Layer and Electron Blocking Layer>>

A blocking layer is appropriately provided in addition to the basic constitution layers composed of organic thin layers as described above. Examples are described in such as JP-A Nos. 11-204258 and 11-204359 and p. 237 of "Organic EL Elements and Industrialization Front Thereof (Nov. 30 (1998), published by N. T. S. Corp.)" is applicable to a hole blocking (hole block) layer according to the present invention.

A hole blocking layer, in a broad meaning, is provided with a function of electron transport layer, being comprised of a material having a function of transporting an electron but a very small ability of transporting a hole, and can improve the recombination probability of an electron and a hole by blocking a hole while transporting an electron.

Further, a constitution of an electron transport layer described above can be appropriately utilized as a hole blocking layer according to the present invention.

The hole blocking layer of the organic EL element of the present invention is preferably arranged adjacent to the light emitting layer.

It is preferable that the hole blocking layer incorporates a nitrogen containing compound such as: a carbazole derivative, an azacarbazole derivative (here, "an azacarbazole derivative" indicates a compound having a structure in which at least one of the carbon atoms constituting the carboline ring is replaced with one or more nitrogen atoms), or a pyridine derivative.

Further, in the present intention, in the case in which a plurality of light emitting layers which differ in a plurality of different emitted light colors, it is preferable that the light emitting layer which results in the shortest wavelength of the emitted light maximum wavelength is nearest to the anode in all light emitting layers. However, in such a case, it is preferable to additionally arrange the hole blocking layer between the aforesaid shortest wavelength, layer and the light emitting layer secondly near the anode.

Further, at least 50% by weight of the compounds incorporated in the hole blocking layer arranged in the aforesaid position preferably exhibits the ionization potential which is greater by at least 0.3 eV than that of the host compounds of the aforesaid shortest wavelength light emitting layer.

The ionization potential is defined as energy which is necessary to release electrons in the HOMO (being the highest occupied molecular orbital) to the vacuum level, and may be determined via, for example, the method described below, (1) By employing Gaussian98 (Gauaaian98, Revision A, 11. 4, M. J. Frisch, et al. Gaussian 98(Gaussian98, Revision A. 11. 4, M. J, Frisch, et al, Gaussian, Inc., Pittsburgh Pa., 2002), which is a molecular orbital calculation software, produced by Gaussian Co. in the United State of America, and by employing B3LYP/6-31G* as a key word, the value (in terms of corresponding eV unit) was computed, and it is possible to obtain the ionization potential by rouging of the second decimal point. The background, in which the resulting calculated values are effective, is that the calculated values obtained by the above method exhibit high relationship with the experimental values.

(2) It is possible to determine the ionization potential via a method in which ionization potential is directly determined employing a photoelectron spectrometry. For example, by employing a low energy electron spectrophotometer "Model AC-1", produced by Riken Keiki Co., or appropriately employ a method known as an ultraviolet light electron spectrometry.

On the other hand, the electron blocking layer, as described herein, has a function of the hole transport layer in a broad sense, and is composed of materials having markedly small, capability of electron transport, while having capability of transporting holes and enables to enhance the recombination probability of electrons and holes by inhibiting electrons, while transporting electrons.

Further, it is possible to employ the constitution of the hole transport layer, described below, as an electron blocking layer when needed. The thickness of the hole blocking layer and the electron transport layer according to the present invention is preferably 3 nm-100 nm, but is more preferably 3 nm-30 nm.

<<Injection Layer: Electron Injection Layer (cathode buffer layer) and Hole Injection Layer>>

An injection layer is appropriately provided and there are two types: an electron injection layer and a hole injection layer, which may be arranged between art anode and a light emitting layer or a hole transport layer, and between a cathode and a light emitting layer or an electron transport layer, as described above.

An injection layer is a layer which is arranged between an electrode and an organic layer to decrease an operating voltage and to improve an emission luminance, which is detailed in volume 2, chapter 2 (pp. 123-166) of "Organic EL Elements and Industrialization Front thereof (Nov. 30th 1998, published by N. T. S Corp.)", and includes a hole injection layer (an anode buffer layer) and an electron injection layer (a cathode buffer layer).

An anode buffer layer (a hole injection, layer) is also detailed in such as JP-A Nos. 9-45479, 9-260062 and 8-288069, and specific examples include: a phthalocyanine buffer layer comprising such as copper phthalocyanine; an oxide buffer layer comprising such as vanadium oxide; an amorphous carbon buffer layer; a polymer buffer layer employing conductive polymer such as polyaniline (or called as emeraldine) or polythiophene; and an orthometalated complex layer comprising such as an iridium complex. Further, an azatriphenylene derivative described in JP-A Nos. 2003-519432 and 2006-135145 can be also used as a hole injection material.

A cathode buffer layer (an election injection layer) is detailed in JP-A Nos. 6-3258871, 9-17574, and 10-74586. Examples of a cathode buffer layer (an electron injection layer) include: a metal buffer layer made of such as strontium and aluminum; an alkaline metal buffer layer made of such as lithium fluoride, sodium fluoride, or potassium fluoride; an alkaline earth metal buffer layer made of such as magnesium fluoride; and an oxide buffer layer made of such as aluminum oxide. The above-described buffer layer (injection layer) is preferably a very thin layer, and the layer thickness is preferably in the range of 0.1 nm -5 μm, although it depends on a raw material.

The material used for an anode buffer layer or for a cathode buffer layer can he used in combination with oilier material. For example, it is possible to use by mixing in a hole transport layer or in an electron transport layer.

<<Anode>>

As an anode according to an organic EL element of the present invention, those comprising metal, alloy, a conductive compound, which is provided with a large work function (4 eV or more), and a mixture thereof as an electrode substance are preferably utilized. Specific examples of such an electrode substance include a conductive transparent material such as metal like Au, CuI, indium tin oxide (ITO), $SnO_2$ and ZnO.

Further, a material such as IDIXO ($In_2O_3$-ZnO), which can prepare au amorphous and transparent electrode, may be also utilized. As for an anode, these electrode substances may be made into a thin layer by a method such as evaporation or spattering and a pattern of a desired form may be formed by means of photolithography, or in the case of requirement of pattern precision is not so severe (not less than 100 μm), a pattern may be formed through a mask of a desired form at the time of evaporation, or spattering of the above-described substance.

Alternatively, when coatable materials such as organic electrically conductive compounds are employed, it is possible to employ a wet system filming method such as a printing system or a coating system.

When emission is taken out of this anode, the transmittance is preferably set to not less than 10% and the sheet resistance as an anode is preferably a few hundreds Ω/□ or less. Further, although the layer thickness depends on a material, it is generally selected in the range of 10 nm-1,000 nm and preferably of 10 nm-200 nm.

<<Cathode>>

On the other hand, as a cathode according to the present invention, metal, alloy, a conductive compound and a mixture thereof, which have a small work function (4 eV or less), are utilized as an electrode substance.

Specific examples of such an electrode substance includes such as sodium, sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture and rare earth metal.

Among them, with respect to an electron injection property and durability against such as oxidation, preferable are: a mixture of election injecting metal with a second metal which is stable metal having a work function larger than electron injecting metal. Examples thereof are: a magnesium/silver mixture, a magnesium/aluminum mixture, a magnesium/indium mixture, an aluminium/aluminium oxide ($Al_2O_3$) mixture, a lithium/aluminum mixture and aluminum.

As for a cathode, these electrode substances may be made into a thin layer by a method such as evaporation or spattering. Further, the sheet resistance as a cathode is preferably not more than a few hundreds Ω/□ and the layer thickness is generally selected in a range of 10 nm-5 μm and preferably of 50 nm-200 nm.

Herein, to transmit produced emission, either one of an anode or a cathode of an organic EL element is preferably transparent or translucent to improve the emission, luminance.

Further, ate forming, on the cathode, the above metals at a film, thickness of 1 nm-20 nm, it is possible to prepare a transparent or translucent cathode in such a manner that electrically conductive transparent materials are prepared thereon. By applying the above, it is possible to produce an element in which both anode and cathode are transparent.

<<Support Substrate>>

A support substrate according to an organic EL element of the present invention is not specifically limited with respect to types of such as glass and plastics. The support substrate may be also called as substrate body, substrate, substrate substance, or support. They me be transparent or opaque. However, a transparent support substrate is preferable when the emitting light is taken from the side of the support substrate.

Support substrates preferably utilized includes such as glass, quartz and transparent resin film. A specifically preferable support substrate is a resin film capable of providing an organic EL element with a flexible property.

Resin films includes such as: polyesters such as polyethylene terephthalate (PET) and polyethylene naphthalate (PEN); polyethylene, polypropylene; cellulose esters or their derivatives such as cellophane, cellulose diacetate, cellulose triacetate, cellulose acetate butylate, cellulose acetate, propionate (CAP), cellulose acetate phthalate (TAC) and cellulose nitrate; polyvinylidene chloride, polyvinyl alcohol, polyethylene vinyl alcohol, syndiotactic polystyrene, polycarbonate, norbornene resin, polymethylpentene, polyether ketone, polyimide, polyether sulfone (PES), polyphenylene sulfide, polysulfones, polyetherimide, polyether ketone imide, polyamide, fluororesin, Nylon, polymethylmethacrylate, acrylic resin, polyacrylate; and cycloolefin resins such as ARTON (produced by JSR Co. Ltd.) and APEL (produce by Mitsui Chemicals, Inc.).

On the surface of a resin film, it maybe formed a film incorporating an inorganic or an organic compound or a hybrid film incorporating both compounds. Barrier films are preferred at a water vapor permeability (25±0.5° C., and relative humidity (90±2) % RH) of 0.01 g/($m^2$·24 h) or less, determined based on JIS K 7129-1992. Further, high barrier films are preferred at an oxygen permeability of $10^{-3}$ ml/($m^2$·24 h·MPa) or less, and at a water vapor permeability of $10^{-5}$ g/($m^2$·24 h) or less, determined based on JIS K 7126-1987.

As materials forming a barrier film, employed may be those which retard penetration of moisture and oxygen, which deteriorate the element. For example, it is possible to employ silicon oxide, silicon dioxide, and silicon nitride. Further, in order to improve the brittleness of the aforesaid film, it is more preferable to achieve a laminated layer structure of inorganic layers and organic layers. The laminating order of the inorganic layer and the organic layer is not particularly limited, but it is preferable that both are alternatively laminated a plurality of times.

Barrier film forming methods are not particularly limited, and examples of employable methods include a vacuum deposition method, a sputtering method, a reactive sputtering method, a molecular beam epitaxy method, a cluster ion beam method, an ion plating method, a plasma polymerization method, a plasma CVD method, a laser CVD method, a thermal CVD method, and a coating method. Of these, specifically preferred is a method employing an atmospheric pressure plasma polymerization method, described in JP-A No. 2004-68143.

Examples of opaque support substrates include metal plates such aluminum or stainless steel films, opaque resin substrates, and ceramic substrates.

The external taking out quantum efficiency of light emitted by the organic EL element of the present invention is preferably at least 1% at room temperature, but is more preferably at least 5%.

External taking out quantum efficiency (%)=(Number of photons emitted by the organic EL element to the exterior/Number of electrons fed to organic EL element)×100.

Further, even by simultaneously employing color hue improving filters such as a color filter, simultaneously employed may be color conversion filters which convert emitted light color from the organic EL element to multicolor by employing fluorescent materials. When the color conversion filters are employed, it is preferable that λmax of light emitted by the organic EL element is 480 nm or less.

<<Preparation Method of Organic EL Element>>

As one example of the preparation method of the organic EL element of the present invention, there will be described the preparation method of the organic EL element composed of: anode/hole injection layer/hole transport layer/light emitting layer/hole blocking layer/electron transport layer/cathode buffer layer (electron injection layer)/cathode.

Initially, a thin film composed of desired electrode substances, for example, anode substances is formed on an appropriate base material to reach a thickness of 1 μm or less, but preferably 10 nm-200 nm, whereby an anode is prepared.

Subsequently, on the above, formed are organic compound thin film layers including a hole injection layer, a hole transport layer, a light emitting layer, a hole blocking layer, an electron transport layer, and a cathode buffer layer, which contain organic materials.

In the organic EL element of phosphorescence luminescence of the present invention, at least a cathode and an electron transport layer located adjacent to the cathode are preferably coated and formed with a wet process.

Examples of a wet process include: a spin coating method, a cast method, a the coating method, a blade coating method, a roll coating method, an inkjet method, a printing method, a spray coating method, a curtain coating method, and a LB method. From the viewpoint of enabling to form a precise thin layer with a high productivity, a the coating method, a roll coating method, an inkjet method and a spray waving method are preferably used. These methods are suitable for applying to a roll to roll production method. It may be possible to use a different film production method for every layer.

As liquid media which are employed to dissolve or disperse organic metal complexes according to the present invention, employed may be, for example, ketones such as methyl ethyl ketone or cyclohexanone, fatty acid esters such as ethyl acetate, halogenated hydrocarbons such as dichlorobenzene, aromatic hydrocarbons such as toluene, xylene, mesitylene, and cyclohexylbenzene, aliphatic hydrocarbons such as cyclohexane, decaline, and dodecane, and organic solvents such as DMF or DMSO.

Further, with regard to dispersion methods, it is possible to achieve dispersion employing dispersion methods such as ultrasonic waves, high shearing force dispersion or media dispersion.

After forming these layers, a thin layer composed of cathode materials is formed on the above layers so that the film thickness reaches 1 µm or less, but is preferably in the range of 50 nm-200 nm, whereby a cathode is arranged, and the desired organic EL element is prepared.

Further, by reversing the preparation order, it is possible to achieve preparation in order of a cathode, a cathode buffer layer, an electron injection layer, an electron transport layer, a light emitting layer, a hole transport layer, a hole injection layer, and an anode.

When direct current voltage is applied to the multicolor display device prepared as above, the anode is employed as "+" polarity, while the cathode is employed as "−" polarity. When 2 V-40 V is applied, it is possible to observe light emission. Further, alternating current voltage may be applied. The wave form of applied alternating current voltage is not specified.

It is preferable to produce an organic EL element of the present invention with one vacuum operation, from formation of a hole injection layer to formation of a cathode without interruption. However, it may be possible to interrupt the operation and take out the intermediate product in order to apply a different film forming method. In that case, working under a dry inert gas atmosphere is preferable.

<<Sealing>>

As sealing means employed in the present invention, listed may be, for example, a method in which sealing members, electrodes, and a supporting substrate are subjected to adhesion via adhesives.

The sealing members may be arranged to cover the display region of an organic EL element, and may be an engraved plate or a flat plate. Neither transparency nor electrical insulation is limited.

Specifically listed are glass plates, polymer plate- films, metal plates, and films. Specifically, it is possible to list, as glass plates, soda-lime glass, barium-strontium containing glass, lead glass, aluminosilicate glass, borosilicate glass, barium borosilicate glass, and quartz.

Further, listed as polymer plates maybe polycarbonate, acryl, polyethylene terephthalate, polyether sulfide, and polysulfone. As a metal plate, listed are those composed of at least one metal selected from the group consisting of stainless steel, iron, copper, aluminum magnesium, nickel, zinc, chromium, titanium, molybdenum, silicon, germanium, and tantalum, or alloys thereof.

In the present invention, since it is possible to convert the element to a thin film, it is possible to preferably employ a metal film.

Further, the oxygen permeability of the polymer film is preferably $1 \times 10^{-3}$ ml/(m$^2 \cdot$24 h·MPa) or less, determined by the method based on JIS K 7126-1987, while its water vapor permeability (at 25 35 0.5° C. and relative humidity (90±2) % RH) is $1 \times 10^{-3}$ g/(m$^2 \cdot$24 h) or less, determined by the method based on JIS K 7129-1992.

Conversion of the sealing member into concave is carried out employing a sand blast process or a chemical etching process.

In practice, as adhesives, listed may be photo-curing and heat-curing types having a reactive vinyl group of acrylic acid based oligomers and methacrylic acid, as well as moisture curing types such as 2-cyanoacrylates. Further listed may be thermal and chemical curing types (mixtures of two liquids) such as epoxy based ones. Still further listed may be hot-melt type polyamides, polyesters, and polyolefins. Yet further listed may be cationically curable type ultraviolet radiation curable type epoxy resin adhesives.

In addition, since an organic EL element is occasionally deteriorated via a thermal process, those are preferred which enable adhesion and curing between room temperature and 80° C. Further, desiccating agents may be dispersed into the aforesaid, adhesives. Adhesives may be applied onto sealing portions via a commercial dispenser or printed on the same in the same manner as screen printing.

Further, it is appropriate that on the outside of the aforesaid electrode which interposes the organic layer and faces the support substrate, the aforesaid electrode and organic layer are covered, and in the form of contact with the support substrate, inorganic and organic material layers are formed as a sealing film. In this case, as materials forming the aforesaid film may be those which exhibit functions to retard penetration of moisture or oxygen which results in deterioration. For example, it is possible to employ silicon oxide, silicon dioxide, and silicon nitride.

Still further, in order to improve brittleness of the aforesaid film, it is preferable that a. laminated layer structure is formed, which is composed of these inorganic layers and layers composed of organic materials.

Methods to form these films are not particularly limited. It is possible to employ, for example, a vacuum deposition method, a sputtering method, a reactive sputtering method, a molecular beam epitaxy method, a cluster ion beam method, an ion plating method, a plasma polymerization method, an atmospheric pressure plasma polymerization method, a plasma CVD method, a thermal CVD method, and a coating method.

In a gas phase and a liquid phase, it is preferable to inject inert gases such as nitrogen or argon, and inactive liquids such as fluorinated hydrocarbon or silicone oil into the space between, the sealing member and the surface region of the organic EL element. Further, it is possible to form vacuum. Still further, it is possible to enclose hygroscopic compounds in the interior.

Examples of hygroscopic compounds include metal oxides (for example, sodium oxide, potassium oxide, calcium oxide, barium oxide, magnesium oxide, and aluminum oxide); sulfates (for example, sodium sulfate, calcium sulfate, magnesium sulfate, and cobalt sulfate); metal halides (for example, calcium chloride, magnesium chloride, cesium fluoride, tantalum fluoride, cerium bromide, magnesium bromide, barium iodide, and magnesium iodide); perchlorates (for example, barium perchlorate and magnesium perchlorate). In sulfates, metal halides, and perchlorates, suitably employed are anhydrides.

<<Protective Film and Protective Plate>>

The aforesaid sealing film on the side which nips the organic layer and faces the support substrate or on the outside of the aforesaid sealing film, a protective or a protective plate may be arranged to enhance the mechanical strength of the element. Specifically, when sealing is achieved via the aforesaid sealing film, the resulting mechanical strength is not always high enough, whereby it is preferable to arrange the protective film or the protective plate described above. Usable materials for these include glass plates, polymer plate-films, and metal plate-films which are similar to those employed for the aforesaid sealing. However, in terms of light weight and a decrease in thickness, it is preferable to employ polymer films.

<<Light Extraction>>

It is generally known that an organic EL element emits light in the interior of the layer exhibiting the refractive index (being about 1.7-2.1) which is greater than that of air, whereby only about 15% -20% of light generated in the light emitting layer is extracted.

This is due to the fact that light incident to an interface (being an interlace of a transparent substrate to air) at an angle of θ which is at least critical angle is not extracted to the exterior of the element due to the resulting total reflection, or light is totally reflected between the transparent electrode or the light emitting layer and the transparent substrate, and light is guided via the transparent electrode or the light emitting layer, whereby light escapes in the direction, of the element side surface.

Means to enhance the efficiency of the aforesaid light extraction include, for example, a method in which roughness is formed on the surface of a transparent substrate, whereby total reflection is minimized at the interface of the transparent substrate to air (U.S. Pat. No. 4,774,435), a method in which efficiency is enhanced in such a manner that a substrate results in light collection (JP-A No. 63-314795), a method in which a reflection surface is formed on the side of the element (JP-A No. 1-220394), a method in which a flat layer of a middle refractive index is introduced between the substrate and the light emitting body and an antireflection film is formed (JP-A No. 62-172691), a method in which a flat layer of a refractive index which is equal to or less than the substrate is introduced between the substrate and the light emitting body (JP-A No. 2001-202827), and a method in which a diffraction grating is formed between the substrate and any of the layers such as the transparent electrode layer or the light emitting layer (including between the substrate and the outside) (JP-A No. 11-283751).

In the present invention, it is possible to employ these methods while combined with the organic EL element of the present invention. Of these, it is possible to appropriately employ the method in which a flat layer of a refractive index which is equal to or less than the substrate is introduced between the substrate and the light emitting body and the method in which a diffraction grating is formed between the substrate and any of the layers such as the transparent electrode layer or the light emitting layer (including between the substrate and the outside).

By combining these means, the present invention enables the production of elements which exhibit higher luminance or excel in durability.

When a low refractive index medium of a thickness, which is greater than the wavelength of light, is formed between the transparent electrode and the transparent substrate, the extraction efficiency of light emitted from the transparent electrode to the exterior increases as the refractive index of the medium decreases.

As materials of the low refractive index layer, listed are, for example, aerogel, porous silica, magnesium fluoride, and fluorine based polymers. Since the refractive index of the transparent substrate is commonly about 1.5-1.7, the refractive index of the low refractive index layer is preferably approximately 1.5 or less, but is more preferably 1.35 or less.

Further, thickness of the low refractive index medium is preferably at least two times the wavelength in the medium. The reason is that, when the thickness of the low refractive index medium reaches nearly the wavelength of light so that electromagnetic waves oozed via evemescent enter into the substrate, effects of the low refractive index layer are lowered.

The method in which the interface which results in total reflection or a diffraction grating is introduced in any of the media is characterized, in that light extraction efficiency is significantly enhanced.

The above method works as follows. By utilizing properties of the diffraction grating capable of changing the light direction to the specific direction different from diffraction via so-called Bragg diffraction such as primary diffraction or secondary diffraction of the diffraction grating, of light emitted from the light entitling layer, light, which is not emitted to the exterior due to total reflection between layers, is diffracted via introduction of a diffraction grating between any layers or in a medium (in the transparent substrate and the transparent electrode) so that light is extracted to the exterior.

It is preferable that the introduced diffraction grating exhibits a two-dimensional periodic refractive, index. The reason is as follows. Since light emitted in the light emitting layer is randomly generated to all directions, in a common one-dimensional diffraction grating exhibiting a periodic refractive index distribution only in a certain direction, light which travels to the specific direction is only diffracted, whereby light extraction efficiency is not sufficiently enhanced, However, by changing the refractive index distribution to a two-dimensional one, light, which travels to all directions, is diffracted, whereby the light extraction efficiency is enhanced.

As noted above, a position to introduce a diffraction grating may be between any layers or in a medium (in a transparent substrate or a transparent electrode). However, a position near the organic light emitting layer, where light is generated, is desirous.

In this case, the cycle of the diffraction grating is preferably from about ½ to 3 times of the wavelength, of light in the medium.

The preferable arrangement of the diffraction grating is such that the arrangement is two-dimensionally repeated in the form of a square lattice, a triangular lattice, or a honeycomb lattice.

<<Light Collection Sheet>>

Via a process to arrange a structure such as a micro-lens array shape on the light extraction side of the organic EL element of the present invention or via combination with a so-called light collection sheet, light is collected in the specific direction such as the front direction with respect to the light emitting element surface, whereby it is possible to enhance luminance in the specific direction.

In an example of the micro-lens array, square pyramids to realize a side length of 30 μm and an apex angle of 90 degrees are two-dimensionally arranged on the light extraction side of the substrate. The side length, is preferably 10 µm-100 µm. When it is less than the lower limit, coloration occurs due to generation of diffraction effects, while when it exceeds the upper limit, the thickness increases undesirably.

It is possible to employ, as a light collection sheet, for example, one which is put into practical use in the LED backlight of liquid crystal display devices. It is possible to employ, as such a sheet, for example, the luminance enhancing film (BEF), produced by Sumitomo 3M Limited.

As shapes of a prism sheet employed may be, for example, Δ shaped stripes of an apex angle of 90 degrees and a pitch of 50 µm formed on a base material, a shape in which the apex angle is rounded, a shape in which the pitch is randomly changed, and other shapes.

Further, in order to control the light radiation angle from the light emitting element, simultaneously employed may be a light diffusion plate-film. For example, it is possible to employ the diffusion film (LIGHT-UP), produced by Kimoto Co., Ltd.

<<Applications>>

It is possible to employ the organic EL element of the present invention as display devices, displays, and various types of light emitting sources. Examples of light emitting sources include, but are not limited to lighting apparatuses (home lighting and car lighting), clocks, backlights for liquid crystals, sign advertisements, signals, light sources of light memory media, light sources of electrophotographic copiers, light sources of light communication processors, and light sources of light sensors. It is effectively employed especially as backlights of liquid crystal display devices and lighting sources.

If needed, the organic EL element of the present, invention may undergo patterning via a metal mask or an ink-jet printing method during film formation. When the patterning is carried out, only an electrode may undergo patterning, an electrode and a light emitting layer may undergo patterning, or all element layers may undergo patterning. During preparation of the element, it is possible to employ conventional methods.

Figure 4:
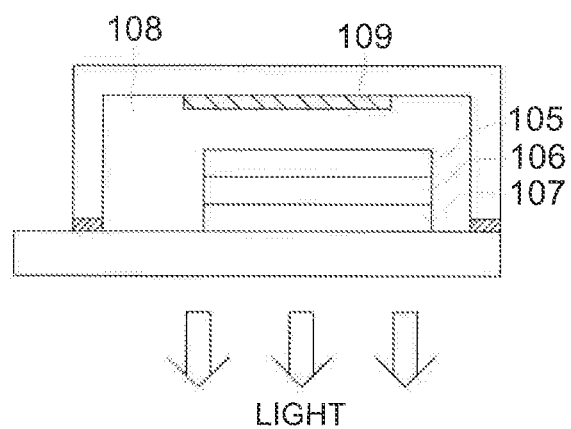
FIG. 4 is a schematic drawing of a lighting device.

Color of light emitted by the organic EL element of the present invention and compounds according to the present invention is specified as follows. In FIG. 4.16 on page 108 of "Shinpen Shikisai Kagaku Handbook (New Edition Color Science Handbook)" (edited by The Color Science Association of Japan, Tokyo Daigaku Shuppan Kai, 1985), values determined via a spectroradiometric luminance meter CS-1000 (produced by Konica Minolta Sensing Inc.) are applied to the CIE chromaticity coordinate, whereby the color is specified.

Further, when the organic EL element of the present invention is a white emission element, "white", as described herein, means that when 2-degree viewing angle front luminance is determined via the aforesaid method, chromaticity in the CIE 1931 Color Specification System at 1,000 cd/m$^2$ is within the region of X=0.33±0.07 and Y=0.33±0.1.

<<Display Device>>

A display device of the present invention will now be explained. The display device of the present invention includes the above-described organic EL element.

A display device of the present invention may be either monochromatic or multi-colored. Here explained will be a multicolor display device. In the case of a multicolor display device, a shadow mask is provided only at the time of emission layer formation, and layers can be formed, all over the surface by such as an evaporation method, a cast method, a spin coat method, an inkjet method and a printing method.

When patterning is performed only for producing a light emitting layer, the method is not specifically limited; however, preferable are an evaporation method, an inkjet method, a spin coating method and a printing method.

The constitution of the organic EL element used for a display device can be selected from the embodiments of the organic EL element as described above, in accordance with the requirement. The production method of the organic EL element was described above for one of the embodiments of the organic EL element of the present invention.

When a direct current voltage is applied on the multicolor display device thus prepared, emission can be observed by application of a voltage of approximately 2 V-40 V setting an anode to "+" polarity and a cathode to "−" polarity. Further, no current flows and no emission generate at all even when a voltage is applied with a reversed polarity.

Further, in the case of alternate current voltage being applied, emission generates only in a state of an anode being "+" and a cathode being "−". Herein, the wave shape of alternate current may be arbitrary.

A multicolor display device can be utilized as a display device, a display and various types of emission light sources. In a display device and a display, full-colored display is possible by employing three types of organic EL elements providing blue, red and green emissions.

A display device and a display include a TV, a personal computer, a mobile instrument an A V instrument, a character broadcast display and an information display in a car. Particularly, the display device and the display may be also utilized as a display to playback still images and moving images, and may adopt either a simple matrix (a passive matrix) mode or an active matrix mode when being utilized as a display device for moving image playback.

An illumination light source includes a home use illumination, a car room illumination, a backlight of a watch or a liquid crystal, a panel advertisement, a signal, a light, source of an optical memory medium, a light, source for an electrophotographic copier, a light source for an optical telecommunication processor and a light source for a photo-sensor, however, the present invention is not limited thereto.

Hereafter, one example of a display device provided with an. organic EL element of the present invention will be explained with reference to figures.

FIG. 1 is a schematic drawing to show air example of a display device constituted of an organic EL element. It is a schematic drawing of a display, which displays image information by emission of an organic EL element, such as a mobile phone.

Display 1 is constituted of display section A having plural number of pixels and control section B which performs image scanning of display section A based on image information.

Control section B, which is electrically connected to display section A, sends a scanning signal and an image data signal to plural number of pixels based on image information from the outside and pixels of each scanning line successively emit depending on the image data signal by a scanning signal to perform image scanning, whereby image information is displayed on display section A.

Figure 2:
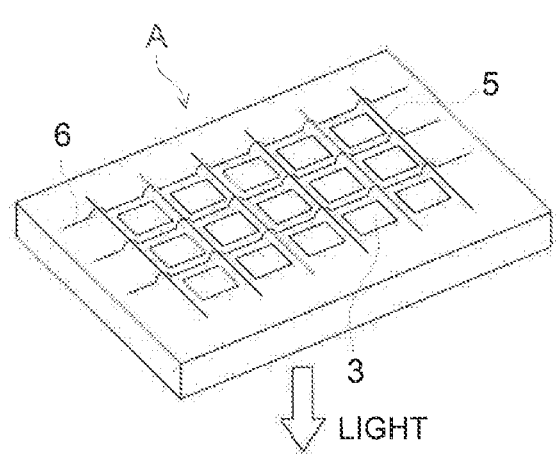
FIG. 2 is a schematic drawing of display section A.

FIG. 2 is a schematic drawing of display section A. Display section A is provided with such as a wiring part, which contains plural scanning lines 5 and data lines 6, and plural pixels 3 on a substrate. Primary part materials of display section A will be explained in the following.

In the drawing, shown is the case that light emitted by pixel 3 is taken out along the white allow (downward).

Scanning lines 5 and plural data lines 6 in a wiring part each are comprised of a conductive material, and scanning lines 5 and data lines 6 are perpendicular in a grid form and are connected to pixels 3 at the right-angled crossing points (details are not shown in the drawing).

Pixel 3 receives an image data from data line 6 when a scanning signal is applied from scanning line 5 and emits according to the received image data.

Full-color display device is possible by appropriately arranging pixels having an emission color in a red region, pixels in a green region and pixels in a blue region, side by side on the same substrate.

<<Lighting Device>>

A lighting device of the present invention will now be explained. The lighting device of the present invention includes the above-described organic EL element.

An organic EL element of the present invention can he utilized as an organic EL element provided with a resonator structure, and a utilization purpose of such an. organic EL element provided with a resonator structure includes such as a light source for an optical memory medium, a light source for an electrophotographic copier, a light source for a optical telecommunication processor and a light source, for a photosensor, however, is not limited thereto.

Further, the organic EL element may he utilized for the above-described applications by being made to perform laser emission. Further, an organic EL element of the present, invention may be utilized as one type of a lamp like an illumination and an exposure light, and may be also utilized as a display device of a projector of an image projecting type and a display device (a display) of a type to directly view still images and moving images.

An operating mode in the case of being utilized as a display device for playback of moving images may be either a simple matrix (a passive matrix) mode or an active matrix mode. In addition, a full-color display device can be prepared by utilizing at least two types of organic EL elements of the present invention which emit different emitting colors.

An organic EL element material of the present invention, can be also applied to an organic EL element to generate emission of practically white color as a lighting device. Plural emission colors are simultaneously emitted by plural number of emission materials to obtain white light by mixing colors. A combination of plural emission colors may be either the one, in which three emission maximum wavelengths of three primary colors of blue, green and red are contained, or the other, in which two emission maximum wavelengths, utilizing a relationship of complimentary colors such as blue and yellow, or blue and orange, are contained.

Further, a combination of emission materials to obtain plural number of emission colors may be either a combination comprising plural number of materials which emit phosphoresce or fluorescence, or a combination of a material which emits phosphoresce or fluorescence and a dye material which emits by light from an emission material as exiting light, however, in a white organic electroluminescence element according to the present invention, it is enough only to mix plural emission dopants in combination.

A mask is provided only at the time of forming such as an emission layer, a hole transport layer or an electron transport layer, to only simply arrange the plural emission dopants such as by separately painting through the mask, while oilier layers are commonly utilized to require no patterning such as a mask. Therefore, such as an electrode can be formed all over the plane by such as an evaporation method, a cast method, a spin coat method, an Inkjet method and a printing method, resulting in improvement of productivity.

According to this method, different from a white organic EL device in which plural colors of emission elements are arranged parallel in an alley form, an element itself is white emitting.

An emission material utilized in an emission layer is not specifically limited, and in the case of a backlight of a liquid crystal display element, any combination by arbitrary selection among platinum complexes according to the present invention or emission materials well known in the art can be utilized so as to be fitted to the wavelength range corresponding to CF (color filter) characteristics, whereby white emission can be obtained.

<<One Embodiment of Lighting Device of the Present Invention>>

It will be described one of the embodiments of a lighting device provided with an organic EL element of the present invention.

The non-light emitting surface of the organic EL element of the present invention was covered with a glass case, and a 300 μm thick glass substrate was employed as a sealing substrate. An epoxy based light curable type adhesive (LUXTRACK LC0629B produced by Toagosei Co., Ltd.) was employed in the periphery as a sealing material. The resulting one was superimposed on the aforesaid cathode to be brought into close contact with the aforesaid transparent support substrate, and curing and sealing were carried out via exposure of UV radiation onto the glass substrate side, whereby the lighting device shown in FIG. 3 and FIG. 4 was formed.

Figure 3:
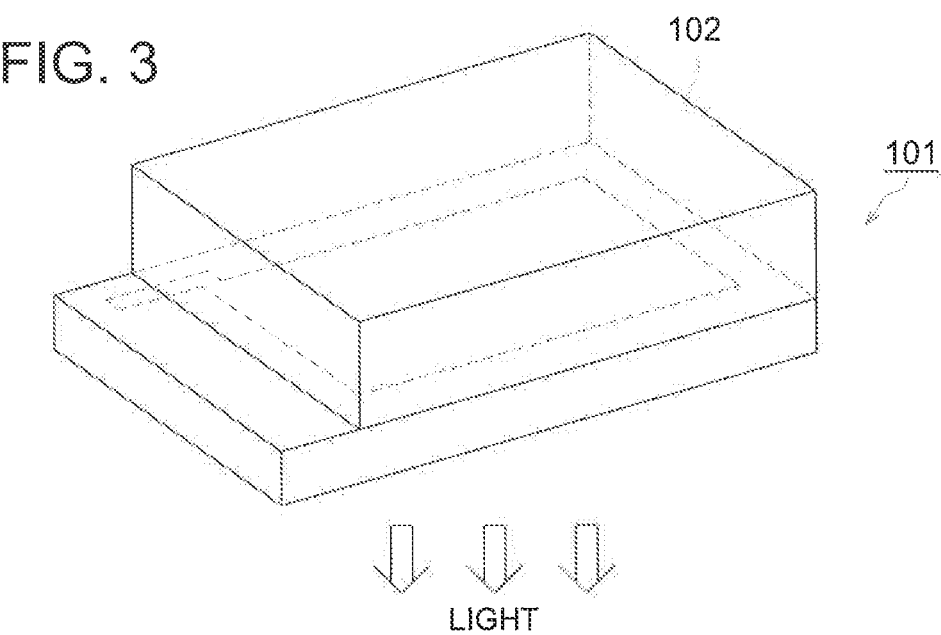
FIG. 3 is a schematic drawing of a lighting device.

FIG. 3 is a schematic view of a fighting device and Organic EL element 101 is covered with glass cover 102 (incidentally, sealing by the glass cover was carried out in a globe box under nitrogen ambience (under air ambience of high purity nitrogen gas at a purity of at least 99.999%) so that Organic EL Element 101 was not brought into contact with atmosphere.

FIG. 4 is a cross-sectional view of a lighting device, and in FIG. 4, 105 represents a cathode, 106 represents an organic EL layer, and 107 represents a glass substrate fitted with a transparent electrode. Further, the interior of glass cover 102 is filled with nitrogen gas 108 and water catching agent 109 is provided.

EXAMPLES

The present invention will now be described with reference to Examples, however the present invention is not limited thereto. The chemical structures of the compounds used in Examples are shown in the following.

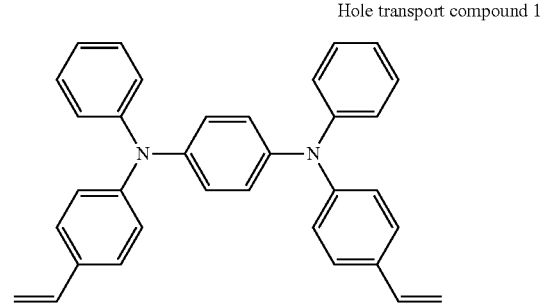

Hole transport compound 1

-continued

Hole transport compound 2

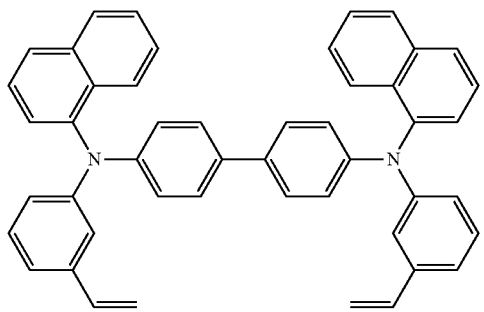

Hole transport compound 3

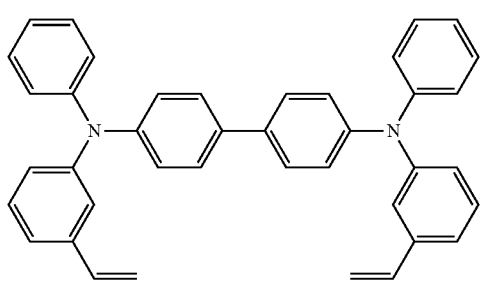

Comparative compound 1

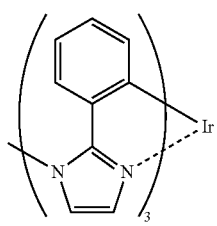

Compound described
in WO 2006046980

Comparative compound 2

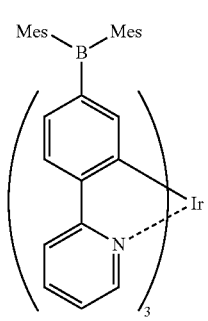

Compound described in
JP-A No. 2004-315509

Comparative compound 3

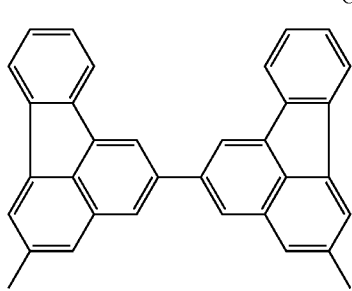

Compound described in
JP-A No. 2005-240008

Comparative compound 5

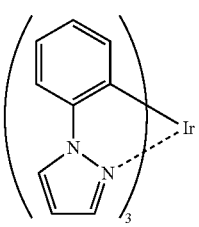

Comparative compound 6

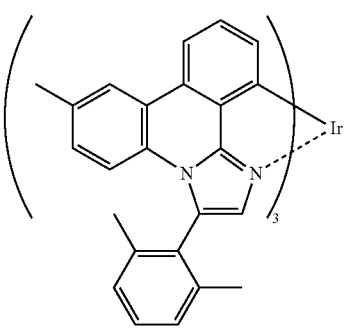

Compound described in
WO 2007095118

Comparative compound 7

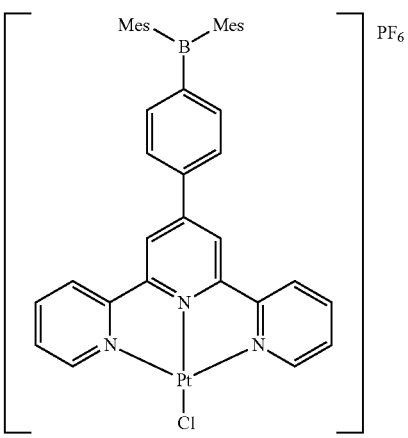

Comopund described in Inorg. Chem.,
2006, 45 (26), 10670-10677

Example 1

<<Synthesis of Example Compound 2-3>>

Example compound 2-3, which is an example compound represented by Formula (1) of me present invention, was prepared in accordance with the following Steps (1) to (3).

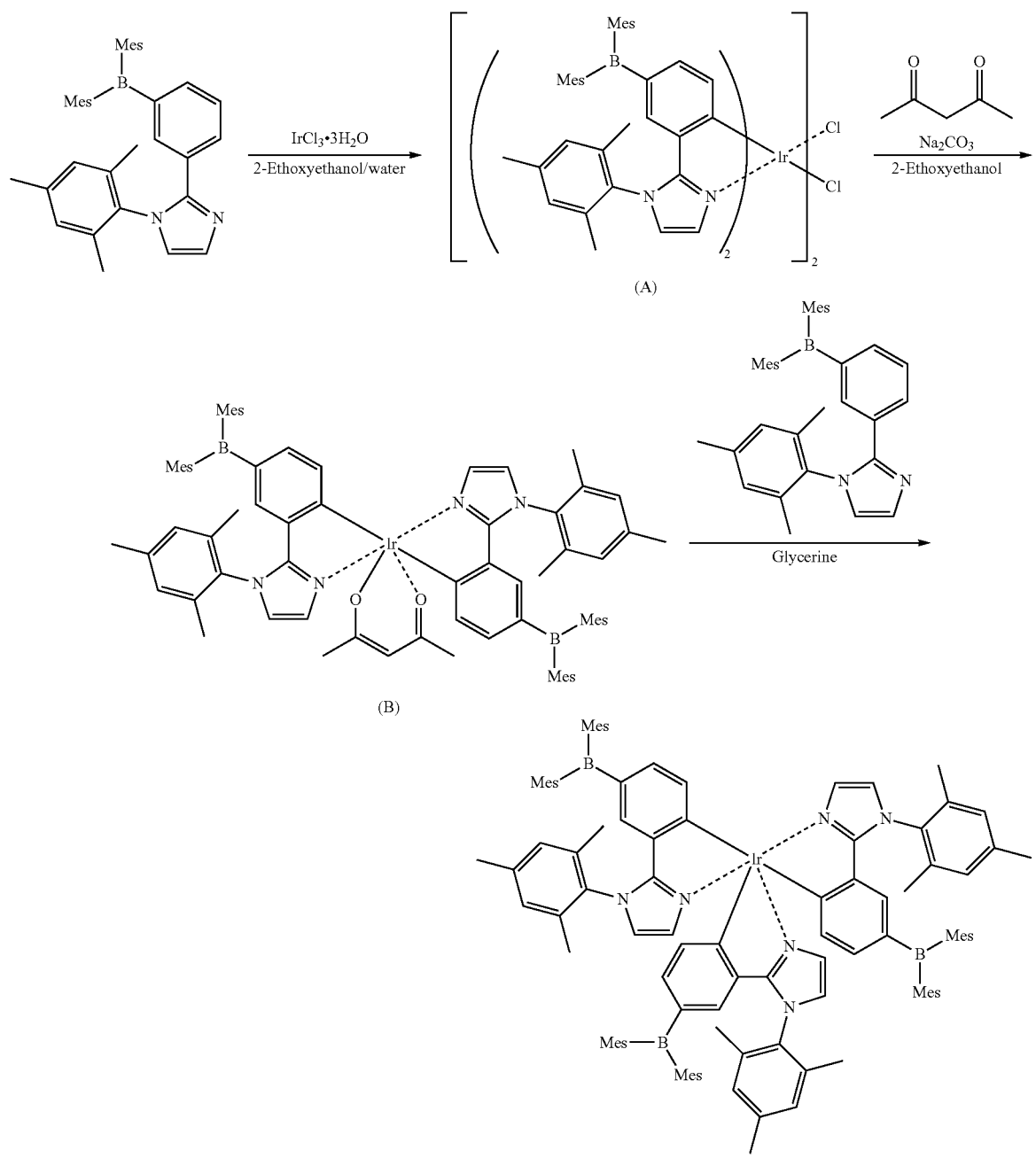

Example compound 2-3

Step (1): Preparation of Dichlorodimer (A)

Into a reaction vessel were placed 2.5 g (0.004987 mole) of 2-[3-(dimesitylboryl)phenyl]-1-mesityl-1H-imidazole, 0.69 g (0.001959 mole) of chloro iridium (III) 3 hydrates, 30 ml of 2-ethoxyethanol, and 10 ml of pure water. The mixture was heated to reflux for 36 hours while bubbling with nitrogen. After cooling the reaction solution, the obtained crystals were filtered, followed by washed with methanol, and they were dried. Thus, It way obtained 2.44 g (yield: 75.6%) of target Dichlorodimer (A).

Step (2): Preparation of Acetyl Acetonate complex (B)

Into a reaction vessel were placed 2.0 g (0.000802 mole) of Dichlorodimer (A), 0.33 g (0.003249 mole), 2.0 g of sodium carbonate, and 45 ml of 2-ethoxyethanol. The mixture was heated to reflux for 2 hours while bubbling with nitrogen. After cooling the reaction solution, the reaction solution was diluted with methanol, and the obtained crystals were filtered. The crystals were sufficiently washed with water to eliminate the residual sodium carbonate. Then, the crystals were washed with methanol and they were dried. Thus, it was obtained 1.73 g (yield: 82.5%) of target Acetyl acetonate complex (B).

Into a reaction vessel were placed 1.5 g (0.001145 mole) of Acetyl acetonate complex (B), 1.75 g (0.003434 mole of 2-[3-(dimesitylboryl)phenyl]-1-mesityl-1H-imidazole, and 45 ml of glycerine. The mixture was heated while bubbling with nitrogen to carry out the reaction with keeping an inner temperature of the vessel to 150° C. for 3 hours. After completion of the reaction, the reaction solution was cooled, and the reaction solution was diluted with methanol. The obtained crystals were filtered. The crystals were sufficiently washed with methanol, and they were dried. The product was purified with flash column chromatography to obtain 1.23 g (yield: 62.3%) of target Example compound 2-3.

The structural confirmation of the prepared. Example compound 2-3 was determined by measurements of NMR spectrum and MASS spectrum.

Example 2

<<Preparation of Organic EL element 1-1>>

An anode was prepared by making patterning to a glass substrate of 100 mm×100 mm×1.1 mm (NA45 produced by NH Techno Glass Corp.) on which a 100 nm film of ITO (indium tin oxide) was formed. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes.

The resulting transparent support substrate was fixed to the substrate holder of a commercial vacuum deposition apparatus. Separately, 200 mg of α-NPD was placed in a molybdenum resistance heating boat, 200 mg of HOST-14 as a host compound was placed in another molybdenum resistance heating boat, 200 mg of BAlq was placed in another molybdenum resistance heating boat, 100 mg of D-9 was placed in another molybdenum resistance heating boat, and 200 mg of $Alq_3$ was placed in another molybdenum resistance heating boat. The resulting boats were fitted in the vacuum deposition apparatus.

Subsequently, after reducing the pressure of the vacuum tank to $4×10^{-4}$ Pa, the aforesaid heating boat containing α-NPD was heated via application of electric current and deposition was earned out onto the transparent support substrate at a deposition rate of 0.1 nm/second, whereby it was produced a hole transport layer having a thickness of 40 nm.

Further, the aforesaid heating boats each respectively containing HOST-14 and D-9 were heated via application of electric current and co-deposition was carried out onto the aforesaid hole transport layer at a respective deposition rate of 0.2 nm/second and 0.012 nm/second, whereby it was produced a light emitting layer having a thickness of 40 nm. The temperature of the substrate at the time of deposition was room temperature.

Further, the aforesaid heating boat containing BAlq was heated via application of electric current and deposition was carried out onto the light emitting layer at a deposition rate of 0.1 nm/second, whereby it was produced a hole blocking layer having a thickness of 10 nm.

The aforesaid heating boat containing $Alq_3$ was heated via application of electric current and deposition was carried out onto the hole blocking layer at a deposition rate of 0.1 nm/second, whereby it was produced an electron transport layer having a thickness of 40 nm. The temperature of the substrate at the time of deposition was room temperature.

Subsequently, 0.5 nm thick lithium fluoride was vapor deposited, and then, 110 nm thick aluminium was vapor deposited to form a cathode, whereby Organic EL element 1-1 was prepared.

The non-light emitting surface of the prepared Organic EL element 1-1 was covered with a glass cover. A glass substrate having a thickness of 300 μm was uses as a sealing substrate. As a sealing material, an epoxy based, light curable type adhesive (LUXTRACK LC0629B produced by Toagosei Co., Ltd,) was applied to the periphery of the glass cover where the glass cover and the glass substrate prepared thereon. Organic EL element were contacted. The resulting one was superimposed on the aforesaid cathode side to be brought into close contact with the aforesaid transparent support substrate, and curing and sealing were carried out via exposure of UV radiation onto the glass substrate side, whereby the lighting device shown in FIG. 3 and FIG. 4 was formed. The organic EL element was evaluated using the lighting device.

FIG. 3 is a schematic drawing of a lighting device. Organic EL element 101 is covered with a glass cover 102 (incidentally, sealing by the glass cover was carried out in a glove box under nitrogen ambience (under an ambience of high purity nitrogen, gas at a purity of 99.999% or more) so that Organic EL element 101 was not brought into contact with atmosphere).

FIG. 4 is a cross-sectional view of a lighting device, and in FIG. 2, 105 represents a cathode, 106 represents an organic EL layer, and 107 represents a glass substrate fitted with a transparent electrode. Further, the interior of glass cover 102 is filled with nitrogen gas 108 and water catching agent 109 is provided.

<<Preparation of Organic EL elements 1-2 to 1-7>>

Organic EL elements 1-2 to 1-7 each were prepared in the same manner as preparation of Organic EL element 1-1, except that the light emitting host and the dopant material were replaced with the compounds as are listed in Table 2.

The Organic EL elements I -1 to 1 -7 thus prepared were evaluated as follows. The evaluation results are shown, in Table 2.

(Emission Lifetime)

Organic EL element was driven with a constant electric current of 2.5 $mA/cm^2$ at room temperature to continuously emit light. The time required for decease in one half of the initial luminance was determined as a half lifetime ($\tau_{1/2}$). The emission lifetime was represented as a relative value when the emission lifetime of Organic EL element 1-1 was set to be 100.

(Initial Driving Voltage)

It was measured an initial driving voltage when Organic EL element was driven with a constant electric current to achieve air initial luminance of 1,000 $cd/m^2$. The initial driving voltage was represented as a relative value when the initial driving voltage of Organic EL element 1-1 was set to be 100.

(Dark Spot)

Organic EL element was driven to continuously emit light with a constant electric current of 2.5 $mA/cm^2$ at room temperature. The light emitting surface was evaluated with visual inspection.

Visual inspection was done by arbitrarily selected 10 persons to each Organic EL element after being driven to continuously emit light for 10 hours. The appearance of dark spots in each Organic EL element was evaluated according to the following rankings.

C: Number of persons who confirmed dark spot is 5 or more.

B: Number of persons who conferred dark spot is 1 to 4.

A: Number of persons who confirmed dark spot is 0.

TABLE 2

| Element No. | Dopant | Host | Lifetime | Initial driving voltage | Dark spot | Remarks |
|---|---|---|---|---|---|---|
| 1-1 | D-9 | HOST-14 | 100 | 100 | C | Comparison |
| 1-2 | Comparative compound 2 | HOST-14 | 254 | 97 | B | Comparison |

181

TABLE 2-continued

| Element No. | Dopant | Host | Life-time | Initial driving voltage | Dark spot | Remarks |
|---|---|---|---|---|---|---|
| 1-3 | 1-2 | HOST-14 | 495 | 89 | A | Invention |
| 1-4 | 1-14 | HOST-25 | 369 | 82 | A | Invention |
| 1-5 | 1-23 | HOST-35 | 336 | 83 | A | Invention |
| 1-6 | 1-27 | HOST-35 | 423 | 91 | A | Invention |
| 1-7 | 1-39 | HOST-25 | 358 | 86 | A | Invention |

From the results in Table 2, it is evident that Organic EL elements of the present invention have a longer lifetime compared with a comparative element. Further, these inventive elements exhibited low initial driving voltage and decreased production of dark spot.

In preparation of Element 1-3, when an element was prepared by further co-depositing α-NPD with a deposition rate of 0.06 nm/second during the formation of a light emitting layer. It was found that this element exhibited an external taking out quantum efficiency (the measuring method is shown below) 1.4 times higher man that of Element 1-1. This improvement is supposed to be produced by largely increased hole transport property caused by interaction between α-NPD and light emitting dopant 2-3.

Example 3

<<Preparation of Organic EL element 2-1>>

An anode was prepared by making patterning to a glass substrate of 100 mm×100 mm×1.1 mm (NA45 produced by NH Techno Glass Corp.) on which a 100 nm film of ITO (indium tin oxide) was formed. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes.

On the transparent support substrate thus prepared was applied a 70% solution of poly(3,4-ethylenedioxythiophene)-polystyrene sulfonate (PEDOT/PSS, Baytron P AI4083 made by Bayer AG.) diluted with water by using a spin coating method at 3,000 rpm for 30 seconds to form a film and then it was dried at 200° C. for one hour. A hole transport layer having a thickness of 20 nm was prepared.

The aforesaid substrate was transferred under an atmosphere of nitrogen, and a solution containing 3 mg of hole transport compound 1 and 40 mg of hole transport compound 2 dissolved in 10 ml of toluene was applied on the aforesaid hole transport layer by using a spin coating method at 1,500 rpm for 30 seconds to form a film. The film was irradiated with UV rays for 180 seconds so as to achieve photopolymerization and cross-linking. A $2^{nd}$ hole transport layer leaving a thickness of 20 nm was thus prepared.

One the $2^{nd}$ hole transport layer was applied a solution containing 100 mg of HOST-9 and 10 mg of Comparative compound 1 dissolved in 10 ml of toluene by using a spin coating method at 600 rpm for 30 seconds to form a film. The film was subjected to vacuum drying at 60° C. for one hour to obtain a light emitting layer having a thickness of 70 nm.

Next, one the light emitting layer was applied a solution containing 50 mg of ET-40 dissolved in 10 ml of hexafluoroisopropanol (HFIP) by using a spin coating method at 1,000 rpm for 30 seconds to form a film. The film was subjected to vacuum drying at 60° C. for one hour to obtain an electron transport layer having a thickness of 30 nm.

Subsequently, this substrate was fixed to the substrate holder of the vacuum deposition apparatus, and the pressure of the vacuum tank was reduced to $4\times10^{-4}$ Pa. Then, 0.4 nm thick potassium fluoride was vapor deposited to form a cathode buffer layer, and then, 110 nm thick aluminum was vapor deposited to form a cathode, whereby Organic EL element 2-1 was prepared, <<Preparation of Organic EL Elements 2-2 to 2-8>>

Organic EL elements 2-2 to 2-8 each were prepared in the same manner as preparation of Organic EL element 2-1, except that HOST-9, Comparative compound 1 and ET-40 were replaced with the compounds as are listed in Table 3.

<<Evaluation of Organic EL elements 2-1 to 2-8>>

In order to evaluate the obtained organic EL elements 2-1 to 2-8, they were sealed in the same manner as sealing of Organic EL elements 1-1 to 1-7 in Example 2. The organic EL elements were evaluated after forming the lighting devices as lustrated in FIG. 3 and FIG. 4.

Then, the following evaluations were carried out.

(Emission Lifetime)

Emission lifetime was evaluated in the same manner as done in Example 2. The emission lifetime was represented as a relative value when the emission lifetime of Organic EL element 2-1 was set to be 100.

(Electric Power Efficiency)

By using a spectroradiometric luminance meter CS-1000 (produced by Konica Minolta Sensing Inc.), a front luminance and an angle dependence of the luminance for a center portion of each Organic EL element were measured. An electric power efficiency at a front luminance of 1,000 cd/m$^2$ was determined.

The electric power efficiency was represented by a relative value when the electric power efficiency of Organic EL element 3-1 was set to be 100.

TABLE 3

| Element No. | Dopant | Host | Electon transport compound | Life-time | Electric power efficiency | Remarks |
|---|---|---|---|---|---|---|
| 2-1 | Comparative compound 1 | HOST-9 | ET-40 | 100 | 100 | Comparison |
| 2-2 | Comparative compound 6 | HOST-9 | ET-40 | 122 | 85 | Comparison |
| 2-3 | 2-3 | HOST-9 | ET-40 | 135 | 160 | Invention |
| 2-4 | 2-5 | HOST-25 | ET-11 | 131 | 141 | Invention |
| 2-5 | 2-18 | HOST-35 | ET-40 | 140 | 148 | Invention |
| 2-6 | 2-19 | HOST-36 | ET-15 | 152 | 121 | Invention |
| 2-7 | 2-23 | HOST-14 | ET-11 | 138 | 158 | Invention |
| 2-8 | 2-38 | HOST-25 | ET-15 | 137 | 112 | Invention |

From the results in Table 3, it is evident that Organic EL elements of the present invention have a longer emission lifetime and high electric power efficiency compared with comparative elements.

Example 4

<<Preparation of Organic EL element 3-1>>

An anode was prepared by making patterning to a glass substrate of 100 mm×100 mm×1.1 mm (NA45 produced by NH Techno Glass Corp.) en which a 100 nm film of ITO (indium tin oxide) was formed. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes.

On the transparent support substrate thus prepared was applied a 70% solution of poly(3,4-ethylenedioxythiphene-polystyrene sulfonate (PEDOT/PSS, Baytron P AI 4083 made by Bayer AG.) diluted with water by using a spin coating method at 3,000 rpm for 30 seconds to form a film and then it was dried at 200° C. for one hour. A hole transport layer having a thickness of 20 nm was prepared.

The aforesaid substrate was transferred under an atmosphere of nitrogen, and a solution containing 50 mg of ADS254B (made by American Dye Source, Inc.,) dissolved in 10 ml of toluene was applied on the aforesaid hole transport layer by using a spin coating method at 2,500 rpm for 30 seconds to form a film. The film was subjected to vacuum drying at 60° C. for one hour to obtain a $2^{nd}$ hole transport layer.

One file $2^{nd}$ hole transport layer was applied a solution containing 100 mg of HOST-30 and 12 mg of Comparative compound 2 dissolved in 10 ml of butyl acetate which was left at room temperature (23 to 25° C.) for 24 hours. This solution, was applied by using a spin coating method at 3,000 rpm for 30 seconds to form a film. The film was subjected to vacuum drying at 60° C. for one hour to obtain a light emitting layer having a thickness of 50 nm.

Next, one the light emitting layer was applied a solution containing 50 mg of ET-10 dissolved in 10 ml of hexafluoroisopropanol (HFIP) by using a spin coating method at 1,500 rpm for 30 seconds to form a film. The film was subjected to vacuum drying at 60° C. for one hour to obtain an electron transport layer having a thickness of 20 nm.

Subsequently, this substrate was fixed to the substrate holder of the vacuum deposition apparatus, and the pressure of the vacuum tank was reduced to $4\times10^{-4}$ Pa Then 0.4 nm thick potassium fluoride was vapor deposited to form a cathode buffer layer, and then, 110 nm thick aluminum was vapor deposited to form a cathode, whereby Organic EL element 3-1 was prepared.

<<Preparation of Organic EL elements 3-2 to 3-7>>

Organic EL elements 3-2 to 3-7 each were prepared in the same manner as preparation of Organic EL element 3-1, except that Comparative dopant 2 was replaced with the compounds as are listed in Table 4.

<<Evaluation of Organic EL Elements 3-1 to 3-7>>

In order to evaluate the obtained organic EL elements 3-1 to 3-7, they were sealed in the same manner as sealing of Organic EL elements 1-1 to 1-7 in Example 2. The organic EL elements were evaluated after forming the lighting devices as lustrated in FIG. 3 and FIG. 4.

Then, the following evaluations were carried out.

External Taking Out Quantum Efficiency

Each organic EL element was allowed to emit light with a constant electric current of 2.5 mA/cm$^2$ at room temperature (at about 23 to 25° C). The external taking out quantum efficiency (η) was determined by measuring the luminance (L) (cd/m$^2$) measured immediately after starting to emit light.

Here, the measurement of luminance was done with a spectroradiometric luminance meter CS-1000 (produced by Konica Minolta Sensing Inc.). The external quantum efficiency was represented by a relative value when the external quantum efficiency of Organic EL element 2-1 was set to be 100.

(Emission Lifetime)

Emission lifetime was evaluated in the same manner as done in Example 2. The emission lifetime was represented as a relative value when the emission lifetime of Organic EL element 3-1 was set to be 100.

The obtained results are shown in Table 4.

TABLE 4

| Element No. | Dopant | Host | Lifetime | External quantum efficiency | Remarks |
|---|---|---|---|---|---|
| 3-1 | Comparative compound 2 | HOST-30 | 100 | 100 | Comparison |
| 3-2 | Comparative compound 3 | HOST-30 | 318 | 58 | Comparison |
| 3-3 | 3-2 | HOST-30 | 165 | 135 | Invention |
| 3-4 | 3-18 | HOST-30 | 148 | 142 | Invention |
| 3-5 | 3-22 | HOST-30 | 169 | 133 | Invention |
| 3-6 | 3-29 | HOST-30 | 162 | 138 | Invention |
| 3-7 | 3-39 | HOST-30 | 142 | 149 | Invention |

From the results in Table 4, it is evident that Organic El elements of the present invention have high external taking out quantum efficiency and longer emission lifetime compared with comparative elements.

Example 5

<<Preparation of Organic EL Element 4-1>>

An anode was prepared by making patterning to a glass substrate of 100 mm×100 mm×1.1 mm (NA45 produced by NH Techno Glass Corp.) on which a 100 nm film ITO (indium tin oxide) was formed. Thereafter, the above transparent support substrate provided with the ITO transparent electrode was subjected to ultrasonic washing with isopropyl alcohol, followed, by drying with desiccated nitrogen gas, and was subjected to UV ozone washing for 5 minutes.

The resulting transparent support substrate was fixed to the substrate holder of a commercial vacuum deposition apparatus. Separately, 200 mg of α-NPD was placed in a molybdenum resistance heating boat, 200 mg of Host compound 1 was placed in another molybdenum resistance heating boat, 200 mg of ET-11 was placed in another molybdenum resistance heating boat, and 100 mg of Comparative compound 1 was placed in another molybdenum resistance hearing boat. The resulting boats were fitted in the vacuum deposition apparatus.

Subsequently, after reducing the pressure of the vacuum tank to $4\times10^{-4}$ Pa, the aforesaid heating boat containing α-NPD was heated via application of electric current and deposition was carried out onto the transparent support substrate at a deposition rate of 0.1 nm/second, whereby it was produced a hole transport layer having a thickness of 40 nm.

Further, the aforesaid heating boats each respectively containing Host compound 1 and Comparative compound 1 were heated via application of electric current and co-deposition was carried out onto the aforesaid hole transport layer at a respective deposition rate of 0.2 nm/second and 0.012 nm/second, whereby it was produced a light emitting layer having a thickness of 40 nm. The temperature of the substrate at the time of deposition was room temperature.

Further, the aforesaid heating boat containing ET-11 was heated via application of electric current and deposition was carried out onto the light emitting layer at a deposition rate of 0.1 nm/second, whereby it was produced a hole blocking layer also served as an electron transport layer having a thickness of 40 nm. The temperature of the substrate at the time of deposition was room temperature.

Subsequently, 2.0 nm thick lithium fluoride was vapor deposited and then, 110 nm thick aluminium was vapor deposited to form a cathode, whereby Organic EL element 4-1 was prepared.

<<Preparation of Organic EL Elements 4-2 to 4-7>>

Organic EL elements 4-2 to 4-7 each were prepared in the same manner as preparation of Organic EL element 4-1, except that Comparative compound 1 used as a dopant and Host compound 1 were replaced with the compounds as are listed in Table 5.

<<Evaluation of Organic EL Elements 4-1 to 4-7>>

In order to evaluate the obtained organic EL elements 4-1 to 4-7, they were sealed in the same manner as sealing of Organic EL elements in Example 2. The organic EL elements were evaluated after forming the lighting devices as lustrated in FIG. 3 and FIG. 4.

Then, the following evaluations were carried out.
(External Taking Out Quantum Efficiency)

The external taking out quantum efficiency (η) was determined in the same manner as done in Example 4.

The external taking out quantum efficiency was represented by a relative value when the external taking out quantum efficiency of Organic EL element 4-1 was set to be 100.
(Driving Voltage Increasing Ratio)

Each Organic EL element was driven with a constant electric current of 2.5 mA/cm$^2$ at room temperature (about 23° C. to 25° C). and the driving voltage (the initial driving voltage) was measured. Then, the driving voltage of each Organic EL element after continued driving for 500 hours was measured (the voltage after 500 hour driving). Driving voltage increasing ratio was determined according to the following scheme.

Driving voltage increasing ratio of each element=(Voltage after 500 hour driving)/(Initial driving voltage)×100

The obtained evaluation results are shown in Table 5.

TABLE 5

| Element No. | Dopant | Host | External quantum efficiency | Voltage increasing ratio | Remarks |
| --- | --- | --- | --- | --- | --- |
| 4-1 | Comparative compound 1 | 1 | 100 | 135 | Comparison |
| 4-2 | Comparative compound 5 | 1 | 12 | 142 | Comparison |
| 4-3 | 4-1 | 7 | 135 | 121 | Invention |
| 4-4 | 4-14 | 19 | 122 | 114 | Invention |
| 4-5 | 4-19 | 35 | 138 | 118 | Invention |
| 4-6 | 4-23 | 54 | 136 | 115 | Invention |
| 4-7 | 4-35 | 1 | 151 | 108 | Invention |

From the results in Table 5, it is evident that Organic El elements of the present invention have high external taking out quantum efficiency and smaller driving voltage increasing ratio compared with comparative elements.

Example 6

<<Preparation of Full-Color Display Device>>
(Preparation of Blue Emission Element)

Organic EL element 4-3 in Example 5 was utilized as a blue emission element.
(Preparation of Green Emission Element)

A green emission element was prepared in the same manner as preparation of Organic EL element 4-1 in Example 5 except that Comparative compound 1 was substituted by D-1. This was used as a green emission element.
(Preparation of Red Emission Element)

A red emission element was prepared in the same manner as preparation of Organic EL element 4-1 in Example 5 except that Comparative compound 1 was substituted by D-10. This was used as a red emission element.

Each, of red, green and blue emission organic EL elements prepared above was arranged parallel on the same substrate to prepare an active matrix mode full-color having a form as described in FIG. 1. Only display section A of the prepared display device is schematically shown in FIG. 2.

That is, a wiring section containing plural lines of scanning line 5 and data line 6, and plural pixels 3 (such as a pixel having an emission color of a red region, a pixel of a green region and a pixel of a blue region) arranged parallel are provided on the same substrate, and scanning lines 5 and data, lines 6 in a wiring section, which are comprised of a conductive material, respectively, cross each other at a right angle in a grid, form to be connected to pixels 3 at the right-angled crossing points (details being not shown in the drawing).

The aforesaid plural pixels 3 each are operated in an active matrix mode, in which an organic EL element, a switching transistor and an operating transistor are provided corresponding to each emission color, and receive an image data signal from date line 6 when a scanning signal is applied from scanning line 5 to emit based on the received image data. Each red, green and blue pixel was appropriately arranged parallel in this manner, whereby a full-color display device was prepared.

It has been proved that a full-color moving image display device exhibiting a high luminance, a high durability and a highly visibility can be achieved by operating said full-color display.

Example 7

<<Preparation of White Emitting Element and White Lighting Device>>

A transparent electrode substrate of Example 2 was subjected to patterning of an electrode having an area of 20 mm ×20 mm, and α-NPD was deposited thereon at a layer thickness of 25 nm as a hole injection transport layer in a similar manner to Example 2. Further, the aforesaid heating boat charged with HOST-25, boat containing Example compound 2-5 and boat containing D-6 each were independently supplied with an electric current to deposit an emission layer having a layer thickness of 30 nm, while adjusting the evaporation rates of HOST-25 as an emission host, Example compound 2-5 and D-6 as emission dopants to be 100:5:0.6.

Successively, BAlq was deposited to a thickness of 10 nm to provide a hole blocking layer. Further, Alq$_3$ was deposited to a thickness of 40 nm to provide an electron transport layer.

Next, similar to Example 2, a mask with square holes having a shape nearly the same as a transparent electrode made of stainless steel was arranged on an electron injection, layer, and 0.5 nm of lithium fluoride as a cathode buffer layer and 150 nm of aluminum as a cathode were deposited to form a film.

This element was equipped with a sealed can, which had a similar structure and was prepared in a similar method to Example 1, to prepare a flat lamp shown in FIG. 3 and FIG. 4. When an electric current was applied to this flat lamp, a substantially white light was obtained, and it was proved that this flat lamp can be used as a lighting device.

Example 8

<<Preparation of White Emission Organic EL Element>>

An. anode was prepared by making patterning to a glass substrate of 100 mm×100 mm×1.1 mm (NA45 produced by NH Techno Glass Corp,) on which a 100 nm film of ITO (indium tin oxide) was formed. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes.

On the transparent support substrate thus prepared was applied a 70% solution of poly(3,4-ethylenedioxythiphene)-polystyrene sulfonate (PEDOT/PSS, Baytron P AI 4083 made by Bayer AG.) diluted with water by using a spin coating method at 3,000 rpm for 30 seconds to form a film and then it was dried at 200° C. for one hour. A $1^{st}$ hole transport layer having a thickness of 30 nm was prepared.

The aforesaid substrate was transferred under an atmosphere of nitrogen, and a solution containing 50 mg of ADS254B (made by American Dye Source, Inc.) dissolved in 10 ml of toluene was applied on the aforesaid hole transport layer by using a spin coating method at 2,500 rpm for 30 seconds to form a film. The film was subjected to vacuum drying at 60° C. for one hour to obtain a $2^{nd}$ hole transport layer.

Subsequently, it was applied a solution containing 100 mg of Host compound 1 and 0.5 mg of D-6, 16 mg of Example compound 5-3 dissolved in 10 ml of butyl acetate by using a spin coating method at 1,000 rpm for 30 seconds to form a film. The film was subjected to vacuum drying at 60° C. for one hour to obtain a light emitting layer.

Further, it was applied a solution containing 25 mg of ET-10 dissolved in 5 ml of hexafluoroisopropanol (HFIP) by using a spin coating method at 2,000 rpm for 30 seconds to form a film. The film was subjected to vacuum drying at 60° C. for one hour to obtain a $1^{st}$ electron transport layer having a thickness of 20 nm.

Subsequently, this substrate was fixed to the substrate holder of the vacuum deposition apparatus. Then, 200 mg of ET-7 was placed in a molybdenum resistance heating boat and it was also set in the vacuum deposition apparatus.

After reducing the pressure of the vacuum tank to $4 \times 10^{-4}$ Pa, the aforesaid heating boat containing ET-7 was heated via application of electric current and deposition was carried out onto the aforesaid electron transport layer at a deposition rate of 0.1 nm/second, whereby it was further produced a $2^{nd}$ electron transport layer having a thickness of 20 nm. The temperature of tine substrate at the time of deposition was room temperature.

Subsequently, 0.5 nm thick lithium fluoride was vapor deposited, and then, 110 nm thick aluminium was vapor deposited to form a cathode, whereby organic EL element was prepared.

This element was equipped with a seeded can, which had a similar structure and was prepared in a similar method to Example 1, to prepare a flat lamp shown in FIG. 3 and FIG. 4. When an electric current was applied to this flat lamp, a substantially white light was obtained, and it was proved that this flat lamp am be used as a lighting device.

Example 9

<<Preparation of Organic EL Element 8-1>>

Organic EL element 8-1 was prepared in the same manner as preparation of Organic EL element 3-1 in Example 4, except that Comparative compound 2 was replaced with Comparative compound 7.

<<Preparation of Organic EL Elements 8-2 to 8-5>>

Organic EL elements 8-2 to 8-5 each were prepared in the same manner as preparation of Organic EL element 3-1, except that Comparative compound 2 was respectively replaced with Examples compounds 1-38, 2-25, 3-17 and 4-8 which are Pt complexes.

The prepared Organic EL elements 8-1 to 8-5 were subjected to the same evaluation as done in Example 3. It was observed that Organic EL elements 8-2 to 8-5 of the present invention exhibited a longer emission lifetime than Organic EL element 8-1 used as a comparison.

From these results, it was demonstrated that the present invention is a technology which can be applicable to a Pt complex.

Example 10

<<Preparation of Organic EL element 9-1>>

The compounds (HOST-9 and Comparative compound 1) used in the light emitting layer of Organic EL element 2-1 in Example 3 were replaced with HOST-38 and Comparative compound 4-11. After forming a film by using a spin coating method as done in Example 3, UV light was irradiated for 60 seconds to make a polymer having a network of host and dopant.

After the aforesaid step, the same steps were performed including sealing as preparation of Organic EL element 2-1. Thus Organic EL element 9-1 was prepared.

<<Preparation of Organic EL Elements 9-2 to 9-5>>

Organic EL elements 9-2 to 9-5 each were prepared in the same manner as preparation of Organic EL element 9-1, except that the dopant was respectively replaced with Example compounds 1-12, 2-8, 2-13 and 3-13.

It was found that the prepared Organic EL elements 9-1 to 9-5 exhibited highly uniform emission and extremely little generation of dark spots.

Example 11

<<Preparation of Organic EL Elements 10-1 to 10-3>>

Organic EL elements 10-1 to 10-3 each were prepared in the same manner as preparation of Organic EL element 1-1 of Example 2, except that Comparative compound 2 was respectively replaced with Example compounds 5-1, 5-5, and 5-7 which are carbene complexes.

It was found that the prepared Organic EL elements 10-1 to 10-3 each exhibited intensive emission. Organic EL elements prepared with a carbene complex were proved to be excellent in element property.

DESCRIPTION OF SYMBOLS

1: Display

3: Pixel

5: Scanning Line

6: Data Line

A: Display Section

B: Control Diction

101: Organic EL Element

102: Glass Cover

105: Cathode

106: Organic EL Layer

107: Glass Substrate having a Transparent Electrode

108: Nitrogen Gas

109: Water Catching Agent

The invention claimed is:
1. An organic electroluminescence material being a compound represented by Formula (1),

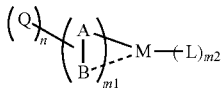

Formula (1)

wherein A and B each represent a 6-membered aromatic hydrocarbon group, or a 5- or 6-membered aromatic heterocyclic group, provided that at least one of A and B represents a 5-membered aromatic heterocyclic group; Q represents a substituent having a vacant orbital which is capable of accepting a π electron from A or B; M represents a transition metal element belonging to groups 8 to 10 in the periodic table; L represents a ligand which is capable of coordinating with M; m1 is an integer of 1 to 3; m2 is an integer of 0 to 2; and n is an integer of 1 to 4, and wherein the substituent Q represents one selected from the group consisting of Q-1, Q-2 and Q-3,

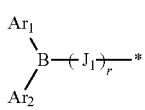

Q-1

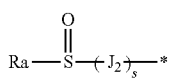

Q-2

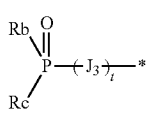

Q-3 wherein $Ar_1$ and $Ar_2$ each respectively represent an aromatic hydrocarbon ring group or an aromatic heterocyclic group, provided that $Ar_1$ and $Ar_2$ may be joined to form an aromatic ring; Ra, Rb and Rc each represent an alkyl group, a cycloalkyl group, an aromatic hydrocarbon ring group or an aromatic heterocyclic group; $J_1$, $J_2$ and $J_3$ each represent an arylene group or a heteroarylene group; and r, s and t each represent an integer of 0 or 1.

2. The organic electroluminescence material of claim 1 wherein the compound represented by Formula (1) is further represented by Formula (2), Formula (3), Formula (4), or Formula (5),

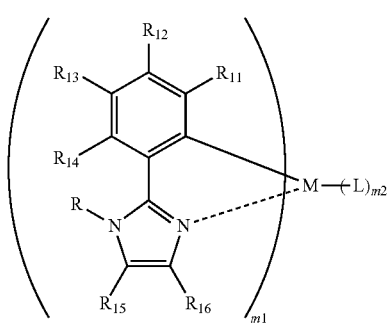

Formula (2)

wherein R represents an alkyl group, a cycloalkyl, an aromatic hydrocarbon group, or an aromatic heterocyclic group; $R_{11}$ to $R_{16}$ each represent a hydrogen atom or a substituent, provided that at least one of $R_{11}$ to $R_{16}$ represents the substituent Q having a vacant orbital which is capable of accepting a π electron from a bonded ring; M represents a transition metal element belonging to groups 8 to 10 in the periodic table; L represents a ligand which is capable of coordinating with M; m1 is an integer of 1 to 3; and m2 is an integer of 0 to 2,

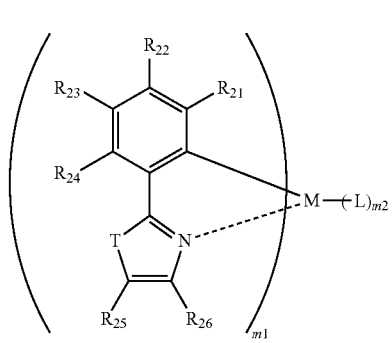

Formula (3)

wherein T represents an oxygen atom or a sulfur atom; $R_{21}$ to $R_{26}$ each represent a hydrogen atom or a substituent, provided that at least one of $R_{21}$ to $R_{26}$ represents the substituent Q having a vacant orbital which is capable of accepting a π electron from a bonded ring; M represents a transition metal element belonging to groups 8 to 10 in the periodic table; L represents a ligand which is capable of coordinating with M; m1 is an integer of 1 to 3; and m2 is an integer of 0 to 2,

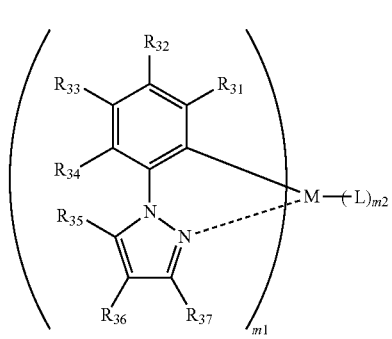

Formula (4)

wherein $R_{31}$ to $R_{37}$ each represent a hydrogen atom or a substituent, provided that at least one of $R_{31}$ to $R_{37}$ represents the substituent Q having a vacant orbital which is capable of accepting a π electron from a bonded ring; M represents a transition metal element belonging to groups 8 to 10 in the periodic table; L represents a ligand which is capable of coordinating with M; m1 is an integer of 1 to 3; and m2 is an integer of 0 to 2, Formula (5)

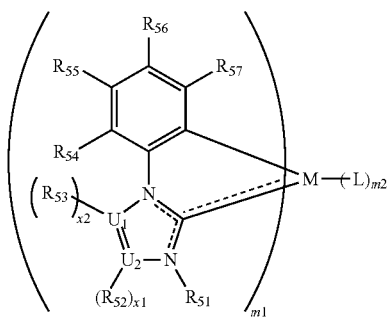

wherein $R_{51}$ to $R_{57}$ each represent a hydrogen atom or a substituent, provided that at least one of $R_{51}$ to $R_{57}$ represents the substituent Q having a vacant orbital which is capable of accepting an electron from a bonded ring; $U_1$ and $U_2$ each represent a carbon atom or a nitrogen atom; M represents a transition metal element belonging to groups 8 to 10 in the periodic table; L represents a ligand which is capable of coordinating with M; m1 is an integer of 1 to 3; m2 is an integer of 0 to 2; and x1 and x2 each represent an integer of 0 or 1.

3. The organic electroluminescence material of claim 2, wherein $R_{13}$ in the compound represented by Formula (2), $R_{23}$ in the compound represented by Formula (3), $R_{33}$ in the compound represented by Formula (4), and $R_{55}$ in the compound represented by Formula (5) each represents the substituent Q.

4. The organic electroluminescence material of claim 1, wherein the substituent Q represents one selected from the group consisting of Q-1-1 to Q-1-10,

Q-1-1

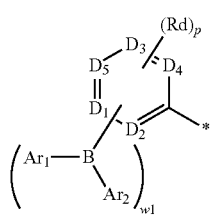

Q-1-2

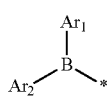

Q-1-3

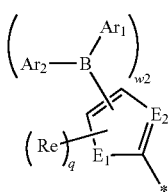

Q-1-4

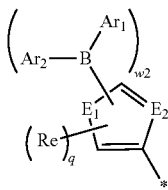

Q-1-5

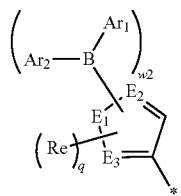

Q-1-6

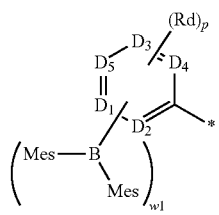

Q-1-7

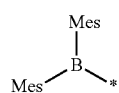

Q-1-8

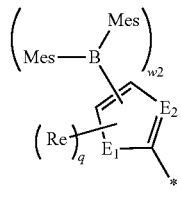

Q-1-9

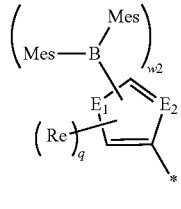

Q-1-10

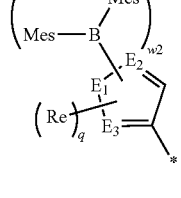

wherein $Ar_1$ and $Ar_2$ each respectively represent an aromatic hydrocarbon ring group or an aromatic heterocyclic group, provided that $Ar_1$ and $Ar_2$ may be joined to form an aromatic ring; $D_1$ to $D_5$ each represent a carbon atom or a nitrogen atom; Rd and Re each represent an alkyl group, a cycloalkyl group, an aromatic hydrocarbon ring group or an aromatic heterocyclic group; p represents an integer of 0 to 4, and q represents an integer of 0 to 2; $E_1$ represents O, S or N-Rf, provided that Rf represents an alkyl group, a cycloalkyl group, an aromatic hydrocarbon ring group or an aromatic heterocyclic group; $E_2$ and $E_3$ each represent a carbon atom or a nitrogen atom; Mes represents a mesityl group; $W_1$ represents an integer of 1 to 5; and W2 represents an integer of 1 to 3.

5. The organic electroluminescence material of claim 2, wherein, in the compound represented by Formula (2), in the compound represented by Formula (3), in the compound represented by Formula (4), or in the compound represented by Formula (5), M represents a platinum atom or an iridium atom.

6. An organic electroluminescence element comprising at least one light emitting layer sandwiched between an anode and a cathode, wherein the light emitting layer contains at least one compound represented by Formula (1) of claim 1.

7. The organic electroluminescence element of claim 6, wherein the compound represented by Formula (1) is further represented by Formula (2), Formula (3), Formula (4), or Formula (5),

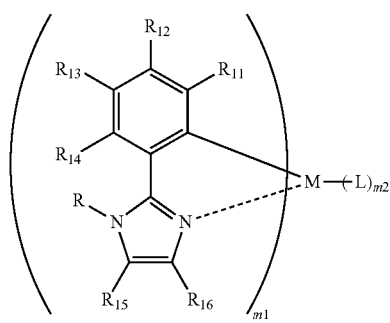

Formula (2)

wherein R represents an alkyl group, a cycloalkyl, an aromatic hydrocarbon group, or an aromatic heterocyclic group; $R_{11}$ to $R_{16}$ each represent a hydrogen atom or a substituent, provided that at least one of $R_{11}$ to $R_{16}$ represents the substituent Q having a vacant orbital which is capable of accepting a π electron from a bonded ring; M represents a transition metal element belonging to groups 8 to 10 in the periodic table; L represents a ligand which is capable of coordinating with M; m1 is an integer of 1 to 3; and m2 is an integer of 0 to 2,

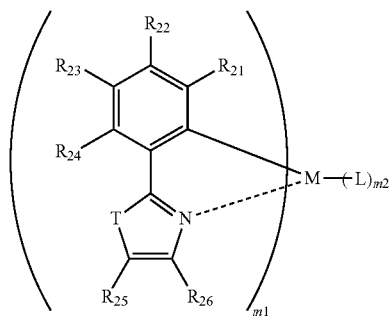

Formula (3)

wherein T represents an oxygen atom or a sulfur atom; $R_{21}$ to $R_{26}$ each represent a hydrogen atom or a substituent, provided that at least one of $R_{21}$ to $R_{26}$ represents the substituent Q having a vacant orbital which is capable of accepting a π electron from a bonded ring; M represents a transition metal element belonging to groups 8 to 10 in the periodic table; L represents a ligand which is capable of coordinating with M; m1 is an integer of 1 to 3; and m2 is an integer of 0 to 2,

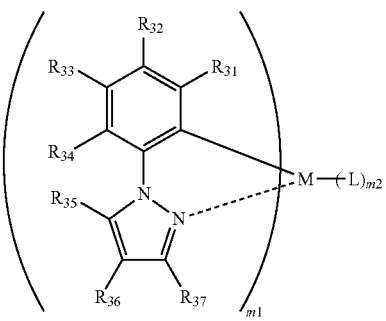

Formula (4)

wherein $R_{31}$ to $R_{37}$ each represent a hydrogen atom or a substituent, provided that at least one of $R_{31}$ to $R_{37}$ represents the substituent Q having a vacant orbital which is capable of accepting a π electron from a bonded ring; M represents a transition metal element belonging to groups 8 to 10 in the periodic table; L represents a ligand which is capable of coordinating with M; m1 is an integer of 1 to 3; and m2 is an integer of 0 to 2,

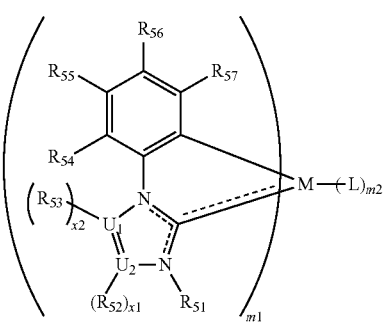

Formula (5)

wherein $R_{51}$ to $R_{57}$ each represent a hydrogen atom or a substituent, provided that at least one of $R_{51}$ to $R_{57}$ represents the substituent Q having a vacant orbital which is capable of accepting a n electron from a bonded ring; $U_1$ and $U_2$ each represent a carbon atom or a nitrogen atom; M represents a transition metal element belonging to groups 8 to 10 in the periodic table; L represents a ligand which is capable of coordinating with M; m1 is an integer of 1 to 3; m2 is an integer of 0 to 2; and x1 and x2 each represent an integer of 0 or 1.

8. The organic electroluminescence element of claim 7, wherein $R_{13}$ in the compound represented by Formula (2), $R_{23}$ in the compound represented by Formula (3), $R_{33}$ in the compound represented by Formula (4), and $R_{55}$ in the compound represented by Formula (5) each represents the substituent Q.

9. The organic electroluminescence element of claim 7, wherein, in the compound represented by Formula (2), in the compound represented by Formula (3), in the compound represented by Formula (4), or in the compound represented by Formula (5), the substituent Q is a substituent containing an element belonging to group 13 in the periodic table, a sulfur atom or a phosphor atom.

10. The organic electroluminescence element of claim 9, wherein the substituent Q is one selected from the group consisting of the partial structures of Q-1, Q-2 and Q-3,

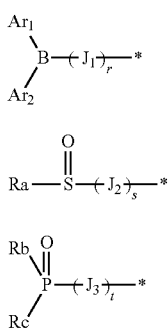

Q-1

Q-2

Q-3 wherein Ar₁ and Ar₂ each respectively represent an aromatic hydrocarbon ring group or an aromatic heterocyclic group, provided that Ar₁ and Ar₂ may be joined to form an aromatic ring;

Ra, Rb and Rc each represent an alkyl group, a cycloalkyl group, an aromatic hydrocarbon ring group or an aromatic heterocyclic group; $J_1$, $J_2$ and $J_3$ each represent an arylene group or a heteroarylene group; and r, s and t each represent an integer of 0 or 1.

11. The organic electroluminescence element of claim 10, wherein the substituent Q is one selected from the group consisting of the partial structures Q-1-1 to Q-1-10,

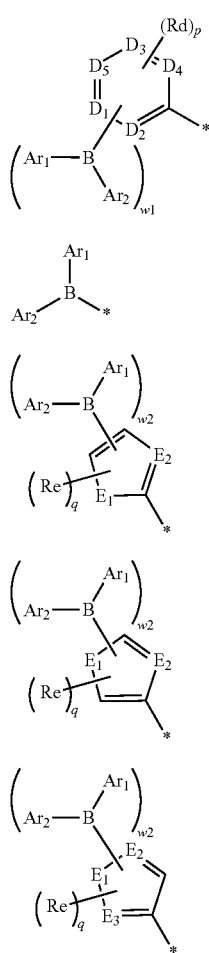

Q-1-1

Q-1-2

Q-1-3

Q-1-4

Q-1-5

Q-1-6

Q-1-7

Q-1-8

Q-1-9

Q-1-10 wherein Ar₁ and Ar₂ each respectively represent an aromatic hydrocarbon ring group or an aromatic heterocyclic group, provided that Ar₁ and Ar₂ may be joined to form an aromatic ring; $D_1$ to $D_5$ each represent a carbon atom or a nitrogen atom; Rd and Re each represent an alkyl group, a cycloalkyl group, an aromatic hydrocarbon ring group or an aromatic heterocyclic group; p represents an integer of 0 to 4, and q represents an integer of 0 to 2; $E_1$ represents O, S or N-Rf, provided that Rf represents an alkyl group, a cycloalkyl group, an aromatic hydrocarbon ring group or an aromatic heterocyclic group; $E_2$ and $E_3$ each represent a carbon atom or a nitrogen atom; Mes represents a mesityl group; W1 represents an integer of 1 to 5; and W2 represents an integer of 1 to 3.

12. The organic electroluminescence element of claim 7, wherein, in the compound represented by Formula (2), in the compound represented by Formula (3), in the compound represented by Formula (4), or in the compound represented by Formula (5), M represents a platinum atom or an iridium atom.

13. The organic electroluminescence element of any one of claim 7,
comprising an organic layer containing at least one compound represented by Formula (2), Formula (3), Formula (4), or Formula (5); and the aforesaid organic layer is formed with a wet process.

14. A display device comprising the organic electroluminescence element of claim 6.

15. A lighting device comprising the organic electroluminescence element of claim 6.

16. The organic electroluminescence material of claim 1, wherein in the compound represented by Formula (1), M represents a platinum atom or an iridium atom.

17. The organic electroluminescence material of claim 6, wherein in the compound represented by Formula (1), M represents a platinum atom or an iridium atom.

18. The organic electroluminescence material of claim 6, wherein an organic layer containing at least one compound represented by Formula (1); and the aforesaid organic layer is formed with a wet process.

\* \* \* \* \*